(12) United States Patent
Mototsu et al.

(10) Patent No.: US 7,964,142 B2
(45) Date of Patent: Jun. 21, 2011

(54) SAMPLE ANALYZER

(75) Inventors: Kazunori Mototsu, Kobe (JP); Seido Biwa, Kobe (JP)

(73) Assignee: Sysmex Corporation, Hyogo (JP)

( * ) Notice: Subject to any disclaimer, the term of this patent is extended or adjusted under 35 U.S.C. 154(b) by 1225 days.

(21) Appl. No.: 10/874,575

(22) Filed: Jun. 24, 2004

(65) Prior Publication Data

US 2005/0024644 A1 Feb. 3, 2005

(30) Foreign Application Priority Data

Jun. 26, 2003 (JP) ................................. 2003-182821

(51) Int. Cl.
*G01N 33/00* (2006.01)
*G01N 33/48* (2006.01)
*G01N 33/50* (2006.01)

(52) U.S. Cl. ........ 422/68.1; 422/73; 422/81; 422/82.01; 356/436; 356/440; 356/441; 436/52; 436/73; 324/71.4; 324/71.1; 73/61.71; 73/864.21; 73/864.81

(58) Field of Classification Search ........................ None
See application file for complete search history.

(56) References Cited

U.S. PATENT DOCUMENTS

| 4,929,426 | A  | * | 5/1990  | Bodai et al. ..................... 422/63 |
| 4,977,517 | A  | * | 12/1990 | Gibbs et al. ..................... 702/51 |
| 5,228,350 | A  |   | 7/1993  | Karpf et al. |
| 5,681,529 | A  |   | 10/1997 | Taguchi et al. |
| 6,387,328 | B1 | * | 5/2002  | Berndtsson ..................... 422/73 |
| 6,389,912 | B1 | * | 5/2002  | Wood ........................... 73/865.5 |
| 2002/0172617 | A1 |   | 11/2002 | Biwa et al. |
| 2003/0041652 | A1 | * | 3/2003  | Spaid et al. .................. 73/54.05 |
| 2005/0118061 | A1 | * | 6/2005  | Mototsu ....................... 422/68.1 |
| 2005/0201901 | A1 | * | 9/2005  | Grossman et al. ........... 422/100 |
| 2005/0214928 | A1 | * | 9/2005  | Larsen et al. .............. 435/287.1 |
| 2006/0150385 | A1 | * | 7/2006  | Gilligan et al. ............ 29/407.08 |
| 2007/0003434 | A1 | * | 1/2007  | Padmanabhan et al. ........ 422/57 |
| 2007/0166195 | A1 | * | 7/2007  | Padmanabhan et al. ..... 422/68.1 |

FOREIGN PATENT DOCUMENTS

| WO | WO-89/04474    | 5/1989 |
| WO | WO-99/01742    | 1/1999 |
| WO | WO 01/11338 A1 | 2/2001 |

* cited by examiner

*Primary Examiner* — P. Kathryn Wright
(74) *Attorney, Agent, or Firm* — Birch, Stewart, Kolasch & Birch, LLP

(57) ABSTRACT

A sample analyzer includes a loading section in which a measuring unit is removably set, the measuring unit being adapted to receive a sample; and a control section which analyzes a signal acquired from the sample received in the measuring unit set in the loading section to provide a result of analysis of the sample; wherein the control section judges whether or not the measuring unit is properly set in the loading section.

5 Claims, 67 Drawing Sheets

US 7,964,142 B2

SAMPLE ANALYZER

CROSS-REFERENCE TO RELATED APPLICATIONS

This application is related to Japanese patent application No. 2003-182821 filed on Jun. 26, 2003, whose priority is claimed under 35 USC §119, the disclosure of which is incorporated by reference in its entirety.

BACKGROUND OF THE INVENTION

1. Field of the Invention

The present invention relates to a sample analyzer, to which a measuring unit is detachably connected.

2. Description of the Related Art

The followings are prior-art devices related to the present invention.

(1) A biological fluid analyzing device for analyzing biological fluid constituents by measuring optical characteristics of a biological fluid sample, the device having a sample receiving port and a pump connection port, and comprising at least one sample treatment chamber, an optical measurement chamber and, optionally, a waste liquid reservoir provided between the sample receiving port and the pump connection port and communicating with one another through flow channels (see, for example, U.S. Pat. No. 5,681,529).

(2) A disposable measuring element comprising: a measurement channel with at least one optical or electrochemical sensor incorporated therein; a first port provided in association with one of opposite ends of the measurement channel for connection to an analyzer; a second port provided in association with the other end of the measurement channel for connection to a sample-taking part; and a common sealing element provided for the first and second ports and having first, second and third positions; wherein the opposite ends of the measurement channel are closed when the sealing element is at the first position; wherein the one end of the measurement channel is connected to the first port and the other end of the measurement channel is connected to a collection tank provided in the measuring element for collecting a liquid drained from the measurement channel when the sealing element is at the second position; wherein the one end of the measurement channel is connected to a buffer tank provided in the measuring element and the other end of the measurement channel is connected to the second port when the sealing element is at the third position (see, for example, U.S. Pat. No. 5,228,350).

In the prior art, the measurement unit (the biological fluid analyzing device or the measuring element) is connected to a sample analyzer, so that only the measurement unit is contaminated with the sample. Therefore, the sample analyzer is kept clean without contamination.

However, if the prior art sample analyzer fails to detect a signal from the sample after the sample is introduced therein, the sample is uselessly consumed. Particularly where the sample is a blood sample or the like taken from a baby or an infant, the amount of the sample is very small. Therefore, the useless consumption of the sample should be avoided.

SUMMARY OF THE INVENTION

The scope of the present invention is defined solely by the appended claims, and is not affected to any degree by the statements within this summary.

According to one aspect of the present invention, there is provided a sample analyzer which can minimize the amount of a sample to be wasted and improve the efficiency of analysis.

According to another aspect of the present invention, there is provided a sample analyzer, which comprises: a loading section in which a measuring unit is removably set, the measuring unit being adapted to receive a sample; and a control section which analyzes a signal acquired from the sample received in the measuring unit set in the loading section to provide a result of analysis of the sample; wherein the control section judges whether or not the measuring unit is properly set in the loading section.

According to another aspect of the present invention, there is provided a sample analyzer, which comprises: a loading section in which a measuring unit is removably set, the measuring unit being adapted to receive a sample; and a control section which analyzes a signal acquired from the sample received in the measuring unit set in the loading section to provide a result of analysis of the sample; wherein the control section judges whether or not the measurement unit is defective.

According to further another aspect of the present invention, there is provided a sample analyzer, which comprises: a loading section in which a measuring unit is removably set, the measuring unit being adapted to receive a sample; a control section which analyzes a signal acquired from the sample received in the measuring unit set in the loading section to provide a result of analysis of the sample; and a transport mechanism for transporting the sample received in the measuring unit; wherein the control section judges whether or not the transport mechanism is defective.

DETAILED DESCRIPTION OF THE INVENTION

Figure 1:
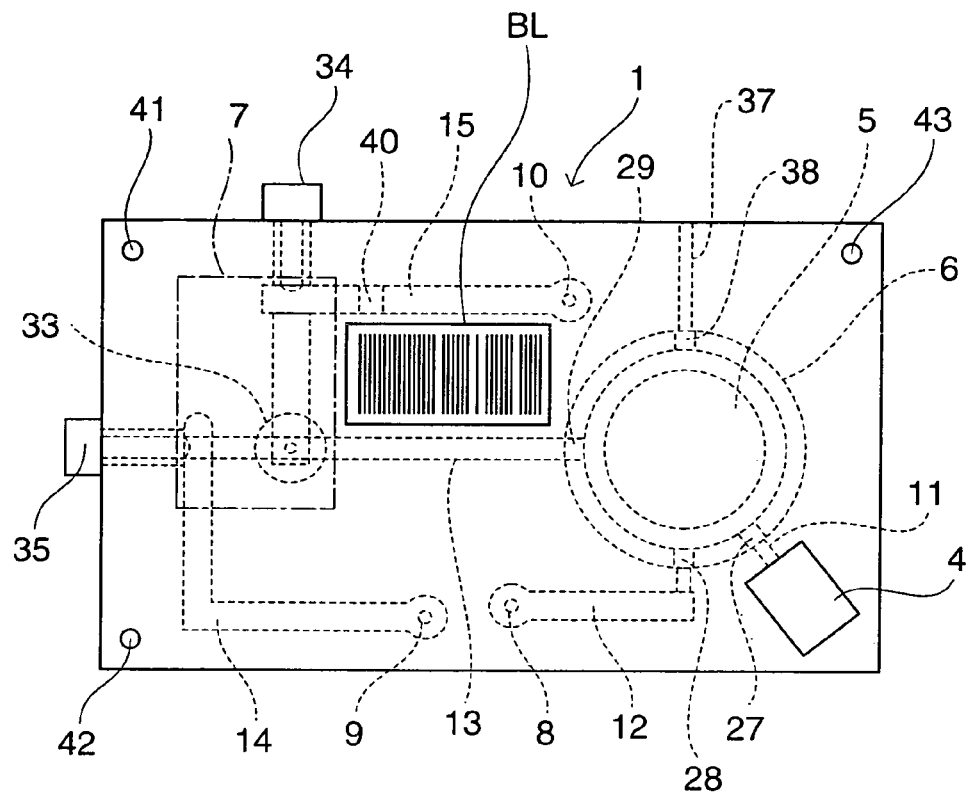
FIG. 1 is a top plan view of a first measuring unit for use in a blood analyzer according to the present embodiment.

A sample analyzer according to the present embodiment comprises: a loading section in which a measuring unit is removably set, the measuring unit being adapted to receive and retain a sample; a control section which analyzes a signal acquired from the sample retained in the measuring unit set in the loading section to provide a result of analysis of the sample; and a transport mechanism for transporting the sample retained in the measuring unit; wherein the control section judges whether or not the measuring unit is properly set in the loading section, whether or not the measuring unit is defective, and/or whether or not the transport mechanism is defective.

In the sample analyzer, different types of measuring units are preferably employed as the measuring unit according to the number and types of measurement items. For example, the sample analyzer employs a first measuring unit for measurement of a first measurement item, and a second measuring unit for measurement of a second measurement item.

In this case, the first measuring unit preferably comprises a metering section for metering a sample, a channel communicating with the metering section, a first measuring chamber provided in the channel for measuring the first measurement item for analysis of the metered sample, and a pressure introduction port communicating with the channel for introducing a pressure into the channel to transport the sample from the metering section to the first measuring chamber. The second measuring unit preferably comprises a metering section for metering the sample, a channel communicating with the metering section, a second measuring chamber provided in the channel for measuring the second measurement item for analysis of the metered sample, and a pressure introduction port communicating with the second measuring chamber for introducing a pressure into the channel to transport the sample from the metering section to the second measuring chamber.

The loading section preferably comprises a unit accommodating section in which the first measuring unit and the second measuring unit are selectively removably set. The transport mechanism preferably comprises a metering section driving source which drives the metering section, and a pump which supplies the pressure to the pressure introduction port. The control section preferably comprises a first computing section which acquires a first analysis signal from the sample retained in the first measuring chamber and analyzes the first analysis signal, a second computing section which acquires a second analysis signal from the sample retained in the second measuring chamber and analyzes the second analysis signal, an operation controlling section, and an output section which outputs an analysis result acquired from at least one of the first and second computing sections.

The first measuring chamber may be an electrical characteristic measuring chamber for measuring an electrical characteristic of the sample, and the second measuring chamber may be an optical characteristic measuring chamber for measuring an optical characteristic of the sample. In this case, the first computing section detects and analyzes the electrical characteristic, and the second computing section detects and analyzes the optical characteristic.

The sample is preferably a blood sample.

The metering section is preferably a rotary valve, which comprises a sample metering section and a channel opening/closing section, and is rotative to actuate the sample metering section and the channel opening/closing section.

The measuring unit may be adapted to measure a plurality of measurement items, and comprise a metering section for metering the sample, a channel communicating with the metering section, a measuring chamber provided in the channel and adapted to retain the metered sample, and a pressure introduction port communicating with the channel for introducing a pressure into the channel to transport the sample from the metering section to the measuring chamber, wherein the measuring chamber comprises an electrical characteristic measuring chamber for measuring an electrical characteristic of the sample and an optical characteristic measuring chamber for measuring an optical characteristic of the sample.

The metering section driving source may be, for example, a stepping motor. The pump for supplying the pressure to the pressure introduction port may be an electric syringe pump or a Perister pump.

The first and second computing sections and the operation controlling section may be constituted by a microprocessor including a CPU, a ROM and a RAM. The output section may comprise a display device such as a CRT or an LCD, and/or a printer such as a thermo-sensitive printer, a laser printer or an ink jet printer.

The metering section may be, for example, a valve. The valve may be a rotary valve, which comprises a sample metering section and a channel opening/closing section, and is rotative to actuate the sample metering section and the channel opening/closing section.

The first analysis signal acquired by the first computing section is, for example, a change in impedance between two electrodes provided in the first measuring chamber. Examples of the analysis result provided by the first computing section include the sizes and numbers of red blood cells, white blood cells, platelets, and toner particles.

The second analysis signal acquired by the second computing section is, for example, the intensity of transmitted light, scattered light or fluorescent light resulting from illumination of the optical characteristic measuring chamber, or the intensity of light emitted from the sample retained in the second measuring chamber. Examples of the analysis result provided by the second computing section include a hemoglobin amount, a blood coagulation period, the activity level of an enzyme such as ALP or peroxidase, the amount of bilirubin, and CRP.

Examples of the measuring units include a measuring unit capable of measuring the sizes and number of white blood cells alone, a measuring unit capable of measuring the sizes and number of white blood cells and the hemoglobin amount, and a measuring unit capable of measuring the hemoglobin amount alone.

With reference to the attached drawings, the present embodiment will hereinafter be described in detail. A blood analyzing system according to this embodiment is adapted to analyze a blood sample to obtain at least one of white blood cell data and a hemoglobin amount. However, it should be understood that the invention be not limited to the embodiment. In the attached drawings, like components will be denoted by like reference characters.

Figure 2:
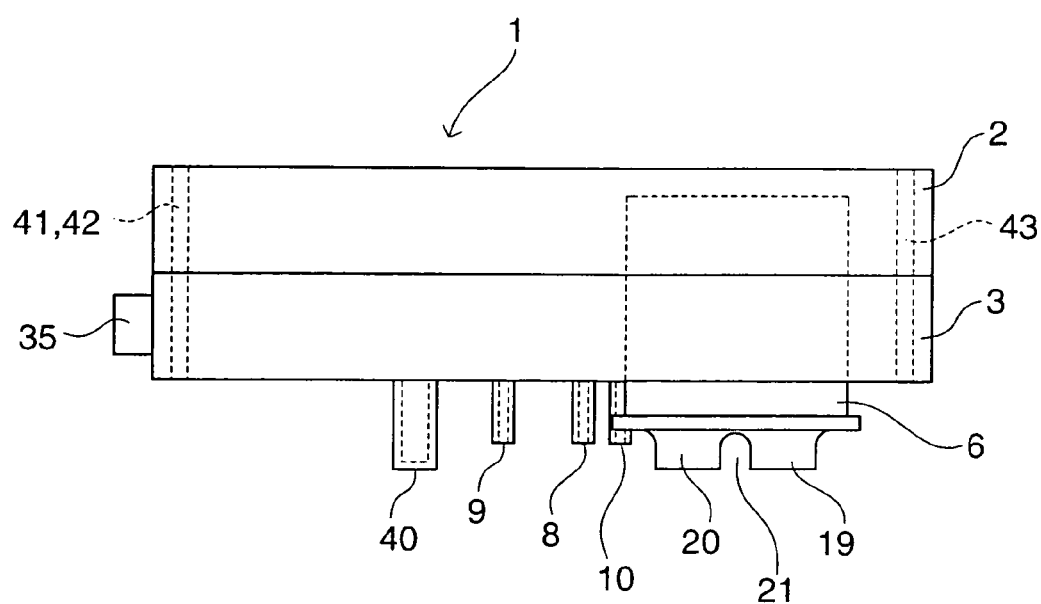
FIG. 2 is a front view of the first measuring unit.
Figure 3:
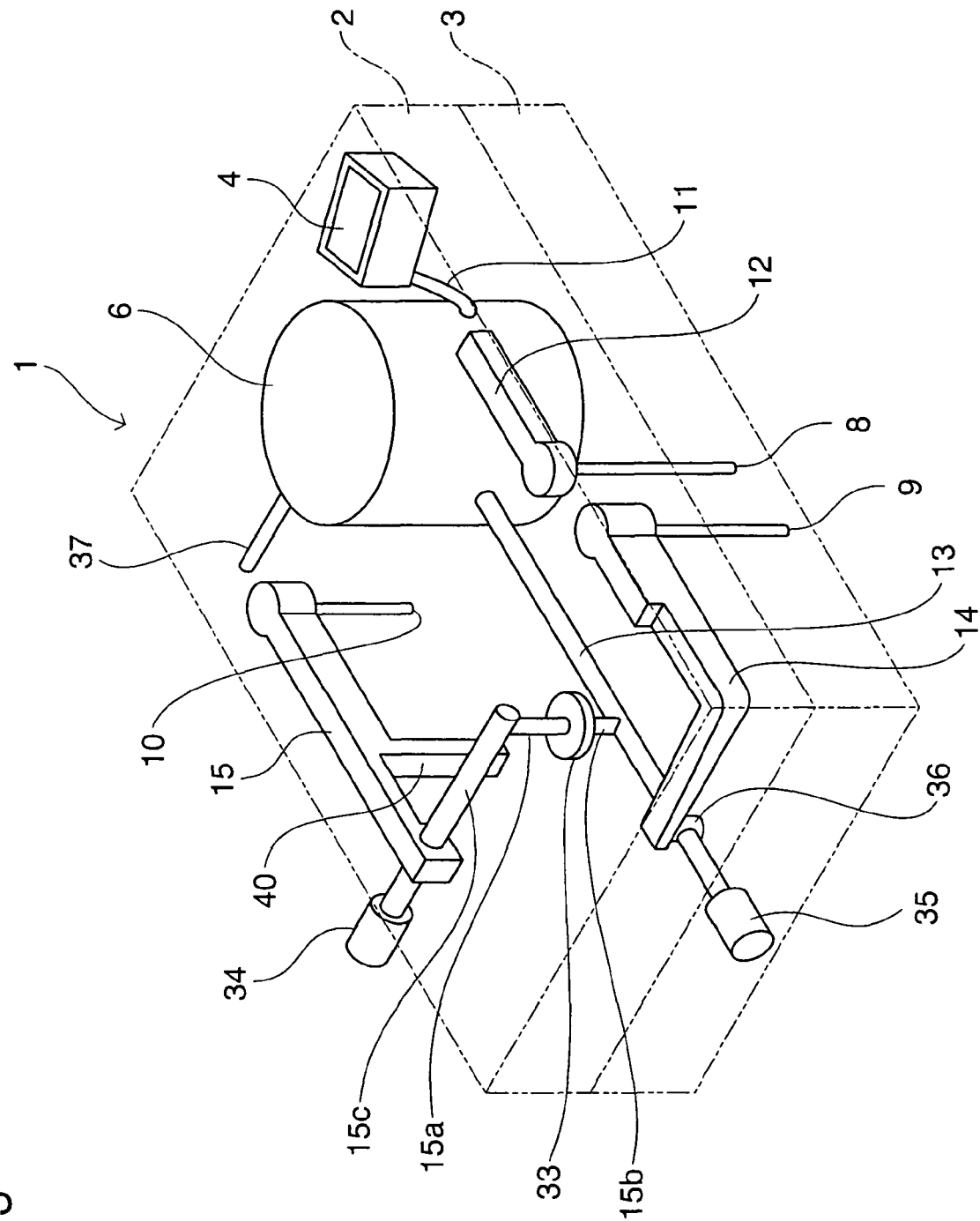
FIG. 3 is a perspective view illustrating the internal construction of the first measuring unit.

A. Measuring Unit
A-1. First Measuring Unit
A-1-1. Construction of First Measuring Unit FIGS. 1 and 2 are a top plan view and a front view, respectively, of a first measuring unit for use in a blood analyzer according to the present embodiment for measurement of white blood cells and hemoglobin. FIG. 3 is a perspective view illustrating the internal construction of the first measuring unit.

As shown in FIGS. 1 to 3, the first measuring unit (hereinafter referred to simply as "first unit") 1 includes an upper plate 2 and a lower plate 3. A bar code label BL for identification of the first unit 1 is applied on an upper surface of the upper plate 2. The first unit 1 includes: a sample receiving section 4 having a volume of 200 µL for receiving a sample; a rotary valve 6 including a diluent container 5 incorporated therein, and having a sample metering function and a flow path switching function; an electrical resistance measuring chamber 7; and first, second and third pump connection ports (pressure introduction port) 8, 9, 10. Further, the first unit 1 includes positioning through-holes 41, 42, 43 for properly positioning the first unit 1 with respect to the blood analyzer to be described later.

The sample receiving section 4 has a sample injection port provided on the top thereof, and the bottom thereof is connected to the rotary valve 6 via a channel 11. The pump connection port 8 is connected to the rotary valve 6 via a channel 12. The electrical resistance measuring chamber 7 is connected to the rotary valve 6 via a channel 13, to the pump connection port 9 via a channel 14, and to the pump connection port 10 via a channel 15. A transparent absorbance measuring chamber 40 is provided in the midst of the channel 15 as projecting from a lower surface of the first unit 1 as shown in FIG. 2. The pump connection ports 8, 9, 10 each have a pipe projecting from the lower surface of the first unit 1 (FIG. 2). A vent hole 37 is provided for opening the rotary valve 6 to the atmosphere (FIG. 1).

As will be detailed later, the channels 11, 12 constitute a metering channel for introducing the sample into a sample metering section. The channel 13 constitutes a measuring channel for introducing a diluted sample from the diluent container 5 into the electrical resistance measuring chamber 7. Further, the channels 13, 14 constitute an agitation channel for agitating a mixture of the metered sample and a diluent for preparation of the diluted sample. The channel 15 allows the electrical resistance measuring chamber 7, the absorbance measuring chamber 40 and the pump connection port 10 to communicate with each other, and constitutes a retention channel for retaining the diluted sample introduced therein after measurement.

Figure 55:
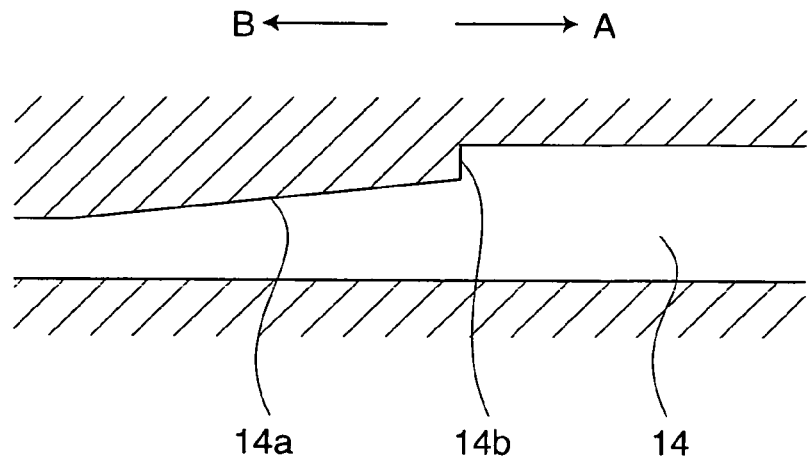
FIG. 55 is a sectional view illustrating a major portion of a channel provided in each of the first to third measuring units.

As shown in FIGS. 3 and 55, the channel 14 has a slant interior portion 14a and a stepped interior portion 14b, so that the sectional area thereof becomes greater toward the pump connection port 9. With this arrangement, bubbles generated when the mixture of the metered sample and the diluent is moved back and forth in arrow directions A and B for agitation thereof are prevented from flowing back to the diluent container 5 (i.e., in the arrow direction B). Thus, the bubbles are prevented from being contained in the diluted sample.

Figure 56:
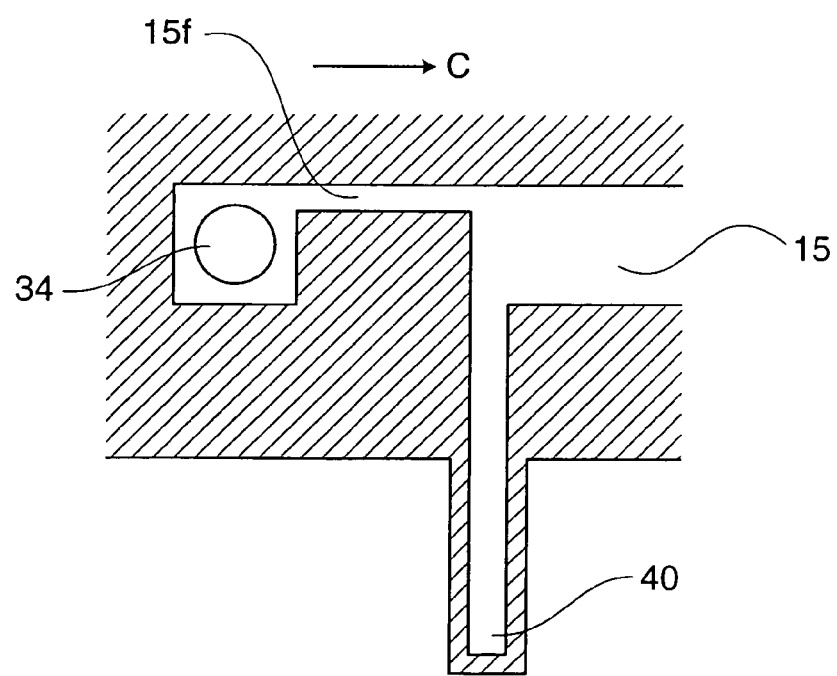
FIG. 56 is a sectional view illustrating a major portion of the channel in each of the first and third measuring units.
Figure 57:
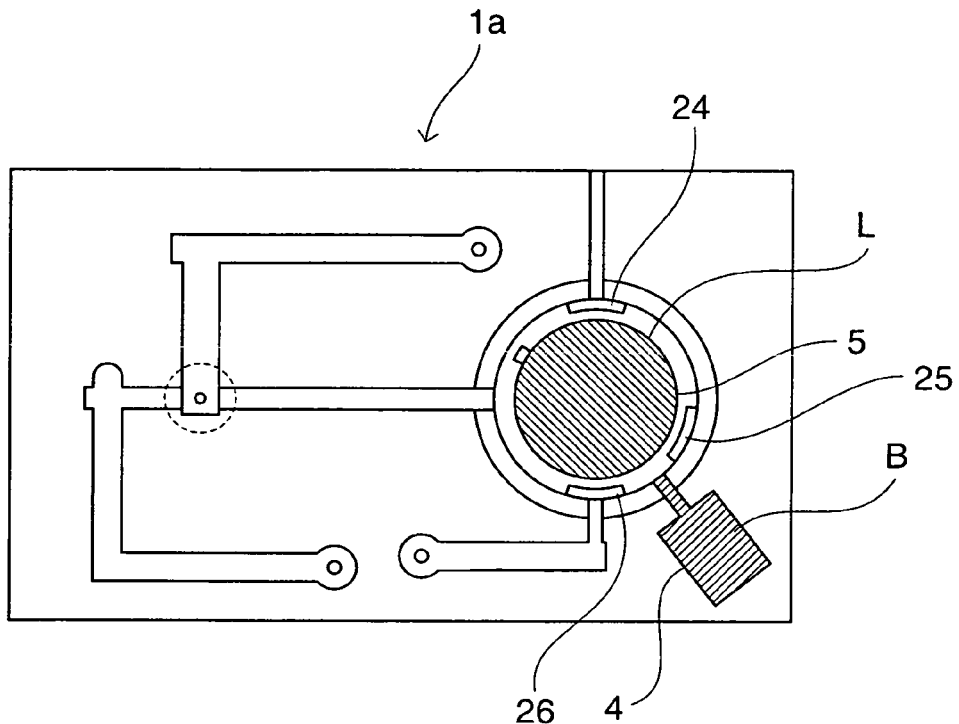
FIGS. 57 to 70 are diagrams for explaining the movement of a sample and a diluent in the second measuring unit.

As shown in FIGS. 3 and 56, the channel 15 has a portion 15f having a sufficiently smaller sectional area than an internal channel 15c provided in the electrical resistance measuring chamber 7. With this arrangement, bubbles generated in the vicinity of an electrode (to be described later) of the electrical resistance measuring chamber 7 when a flow rate in the channel 15 is increased are sucked together with the diluted sample in an arrow direction C, so that the electrical resistance measuring chamber 7 is not influenced by the bubbles during the measurement.

A-1-2. Construction of Rotary Valve

Figure 4:
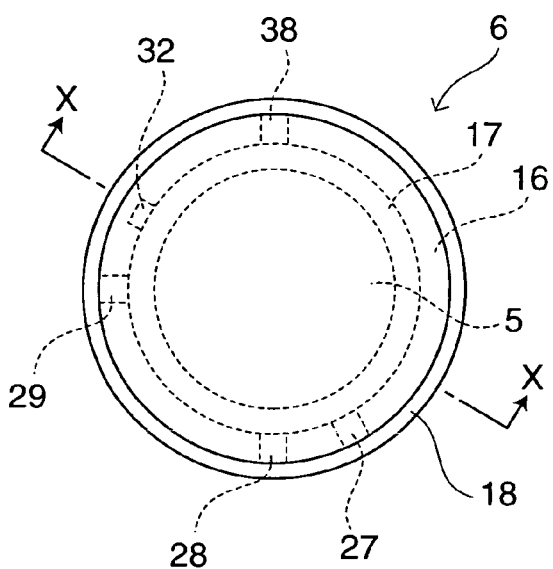
FIG. 4 is a top plan view of a rotary valve provided in each of the first to third measuring units.
Figure 5:
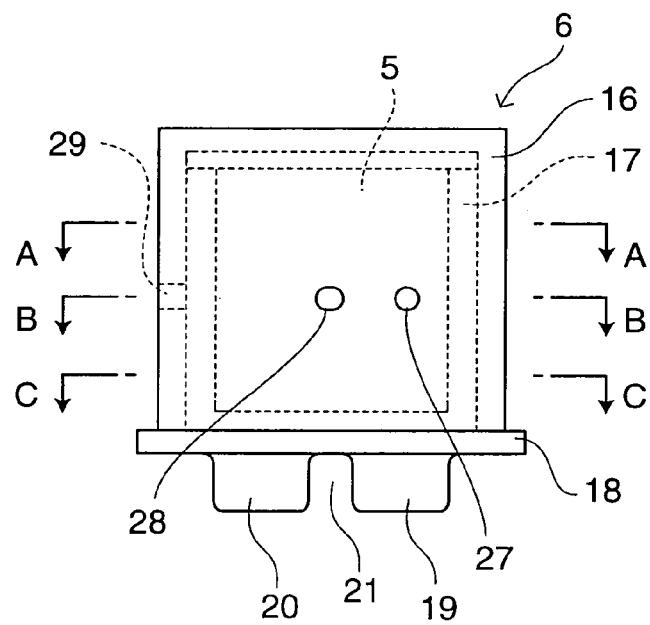
FIG. 5 is a front view of the rotary valve.
Figure 6:
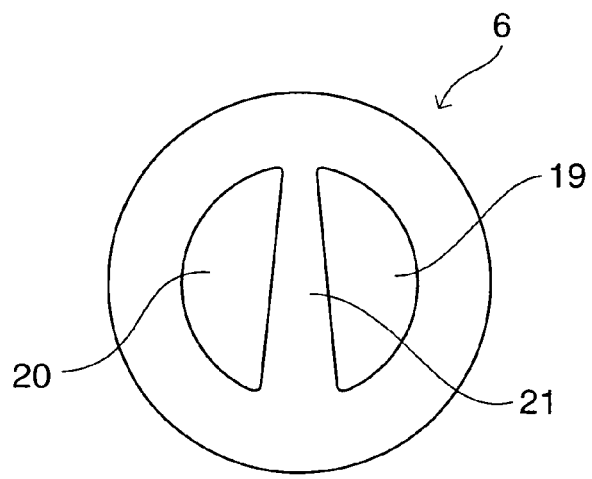
FIG. 6 is a bottom view of the rotary valve.

FIGS. 4, 5 and 6 are a top plan view, a front view and a bottom view, respectively, of the rotary valve 6. As shown in FIGS. 4 to 6, the rotary valve 6 includes an outer cylinder 16 having an open bottom, and an inner cylinder 17 having a closed bottom and inserted in the outer cylinder 16 from the open bottom of the outer cylinder 16. The inner cylinder 17 has an open top, and a flange 18 provided at the bottom thereof.

Two projections 19, 20 project downward from the flange 18 to define a groove 21 having non-parallel edges therebetween. The projections 19, 20 constitute a connector to be connected to a valve driving source to be described later. When the inner cylinder 17 is rotated about an axis thereof, an outer circumferential surface of the inner cylinder 17 is slidable in contact with an inner circumferential surface of the outer cylinder 16. Although the groove 21 has the non-parallel edges in this embodiment, the groove 21 may have parallel edges.

Figure 7:
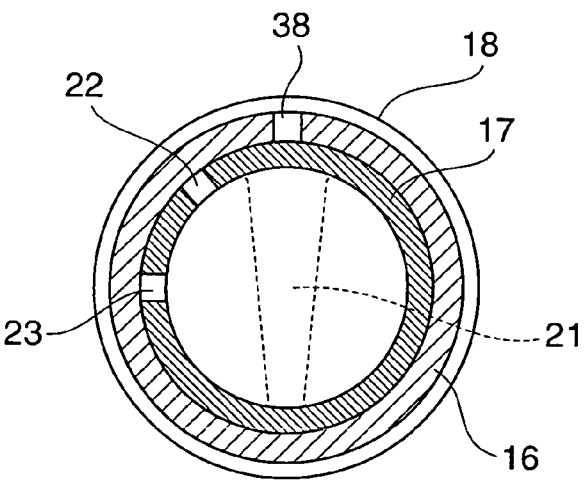
FIG. 7 is a sectional view of the rotary valve as seen in an arrow direction A-A in FIG. 5.
Figure 8:
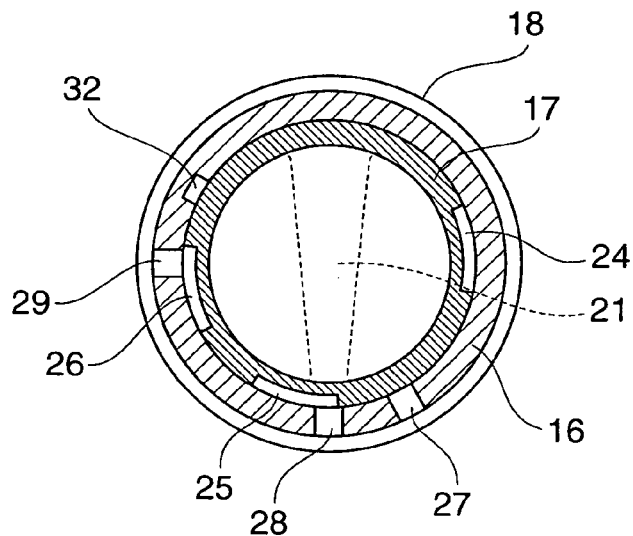
FIG. 8 is a sectional view of the rotary valve as seen in an arrow direction B-B in FIG. 5.
Figure 9:
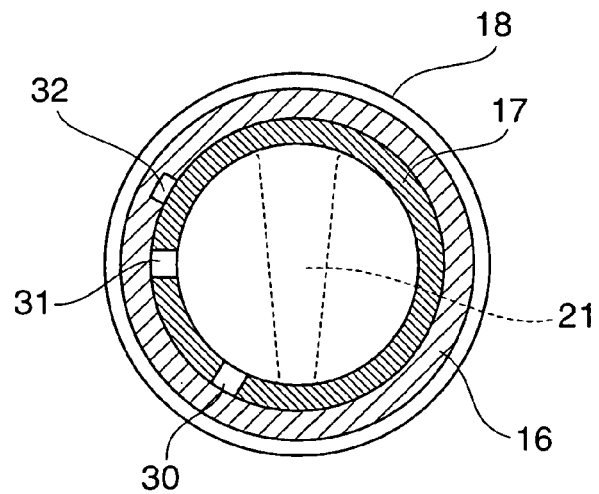
FIG. 9 is a sectional view of the rotary valve as seen in an arrow direction C-C in FIG. 5.
Figure 10:
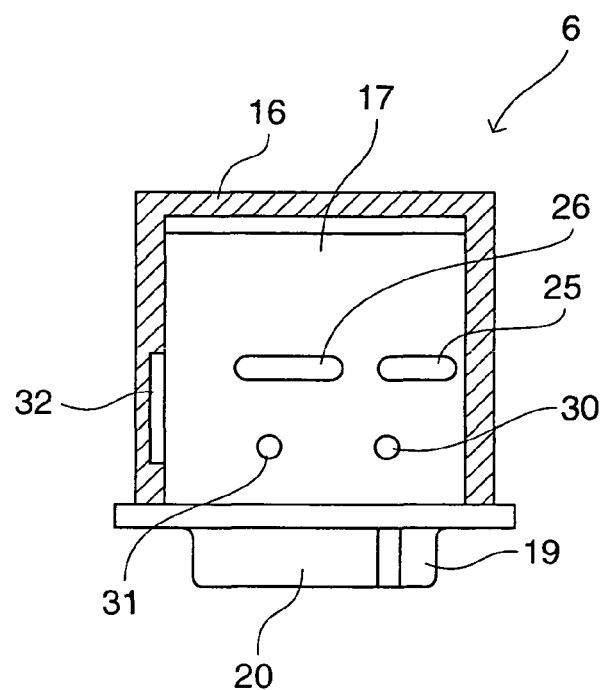
FIG. 10 is a sectional view of the rotary valve as seen in an arrow direction X-X in FIG. 4.

FIGS. 7, 8 and 9 are sectional views of the rotary valve 6 as seen in arrow directions A-A, B-B and C-C, respectively, in FIG. 5. FIG. 10 is a sectional view of the rotary valve 6 as seen in an arrow direction X-X in FIG. 4. As shown in FIG. 7, the inner cylinder 17 has two through-holes 22, 23 formed in an upper portion thereof for opening and closing the vent hole 37, and the outer cylinder 16 has a through-hole 38 communicating with the vent hole 37.

As shown in FIG. 8, the inner cylinder 17 has three elongated lateral grooves 24, 25, 26 formed in circumferentially aligned relation in a middle portion of the outer circumferential surface thereof, and the outer cylinder 16 has three through-holes 27, 28 and 29 communicating with the channels 11, 12 and 13, respectively.

As will be described later, the lateral groove 25 serves as the sample metering section, and the lateral grooves 24, 26 serve as channel opening/closing grooves.

As shown in FIG. 9, the inner cylinder 17 has two through-holes 30, 31 formed in a lower portion thereof for channel opening and closing. As shown in FIGS. 8 to 10, the outer cylinder 16 further has an elongated vertical groove 32 formed in the inner circumferential surface thereof as extending axially from a middle portion to a lower portion thereof.

A-1-3. Construction of Electrical Resistance Measuring Chamber

As shown in FIGS. 1 and 3, the electrical resistance measuring chamber 7 includes a disk pellet (separation plate) 33 provided between vertical portions 15*a* and 15*b* of the internal channel 15*c* thereof, an electrode 34 provided in a junction between the channels 15 and 15*c* with a distal end thereof exposed to the inside of the channel junction, and an electrode 35 provided in a junction 36 between the channels 13 and 14 with a distal end thereof exposed to the inside of the channel junction.

Figure 11:
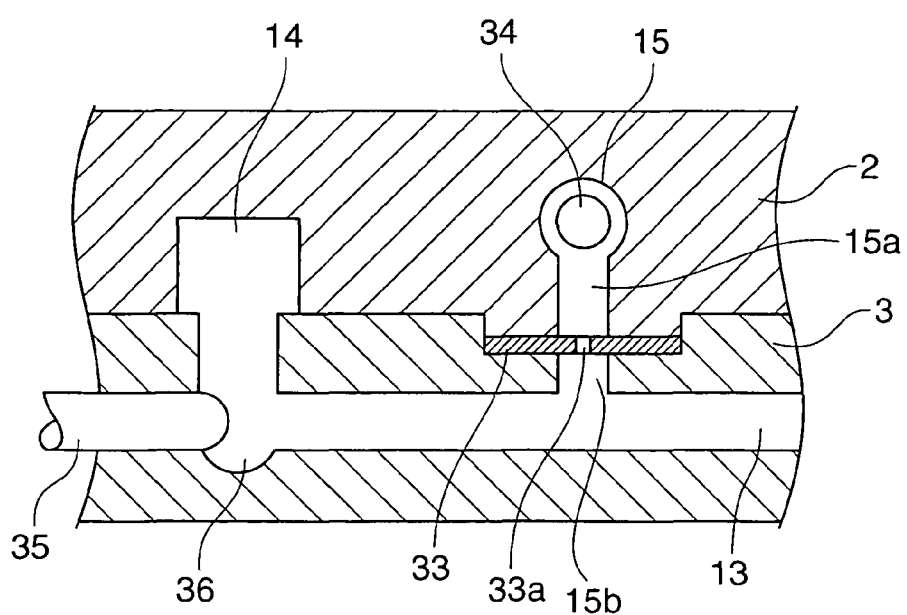
FIG. 11 is a sectional view illustrating a major portion of an electrical resistance measuring section provided in each of the first and second measuring units.

FIG. 11 is a sectional view illustrating a major portion of the electrical resistance measuring chamber 7. The pellet 33 is fitted in a round recess formed in the lower plate 3 coaxially with the vertical portion 15*b* and pressed by a round projection provided on the upper plate 2 coaxially with the vertical portion 15*a*.

The pellet 33 has a minute through-hole (orifice) 33*a* formed in the center thereof, so that the electrical resistance of an electrolytic solution passing through the minute throughhole 33*a* is measured by the electrodes 34, 35. The pellet 33 is formed of a polyetherimide sheet having a thickness of 125 μm. The minute through-hole 33*a* is formed in the sheet as having a diameter of 100 μm by an excimer laser.

A-2. Second Measuring Unit

A-2-1. Construction of Second Measuring Unit

Figure 12:
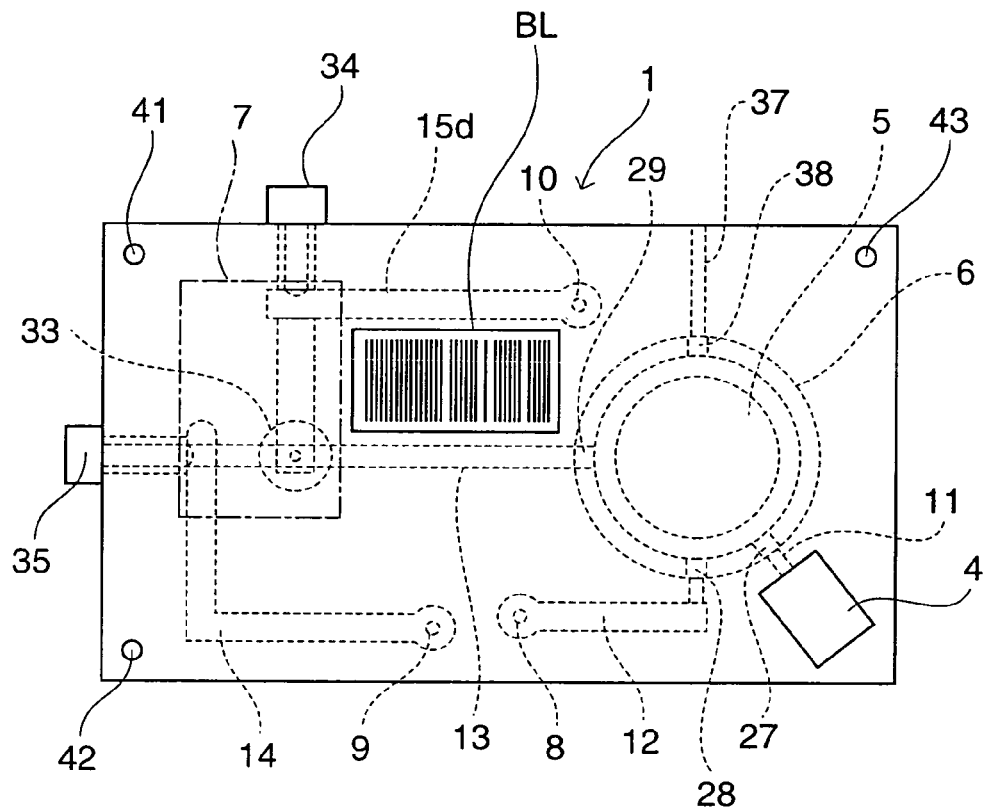
FIG. 12 is a top plan view of the second measuring unit for use in the blood analyzer according to the present embodiment.
Figure 13:
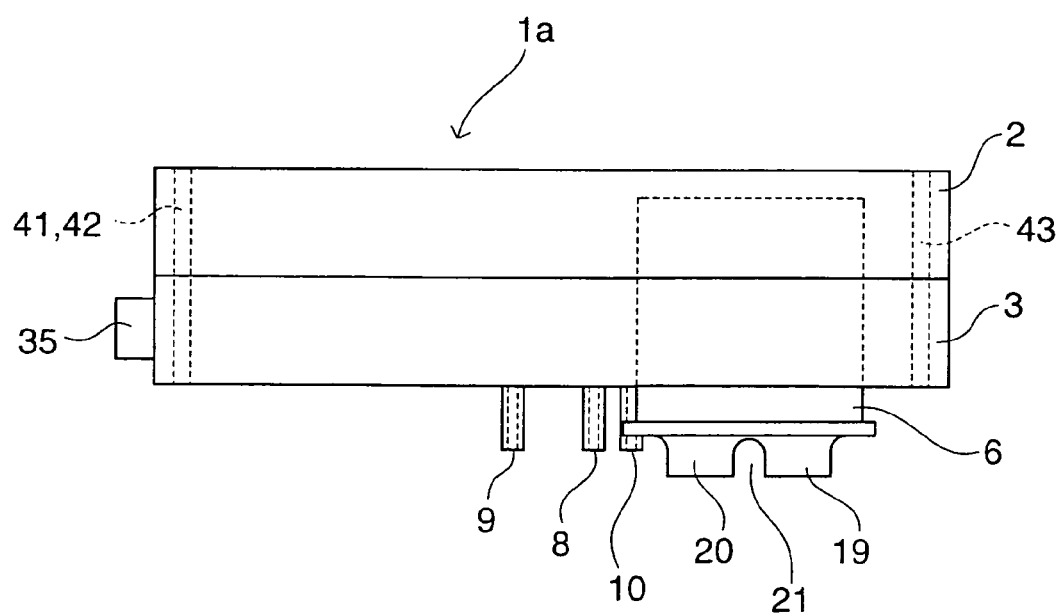
FIG. 13 is a front view of the second measuring unit.
Figure 14:
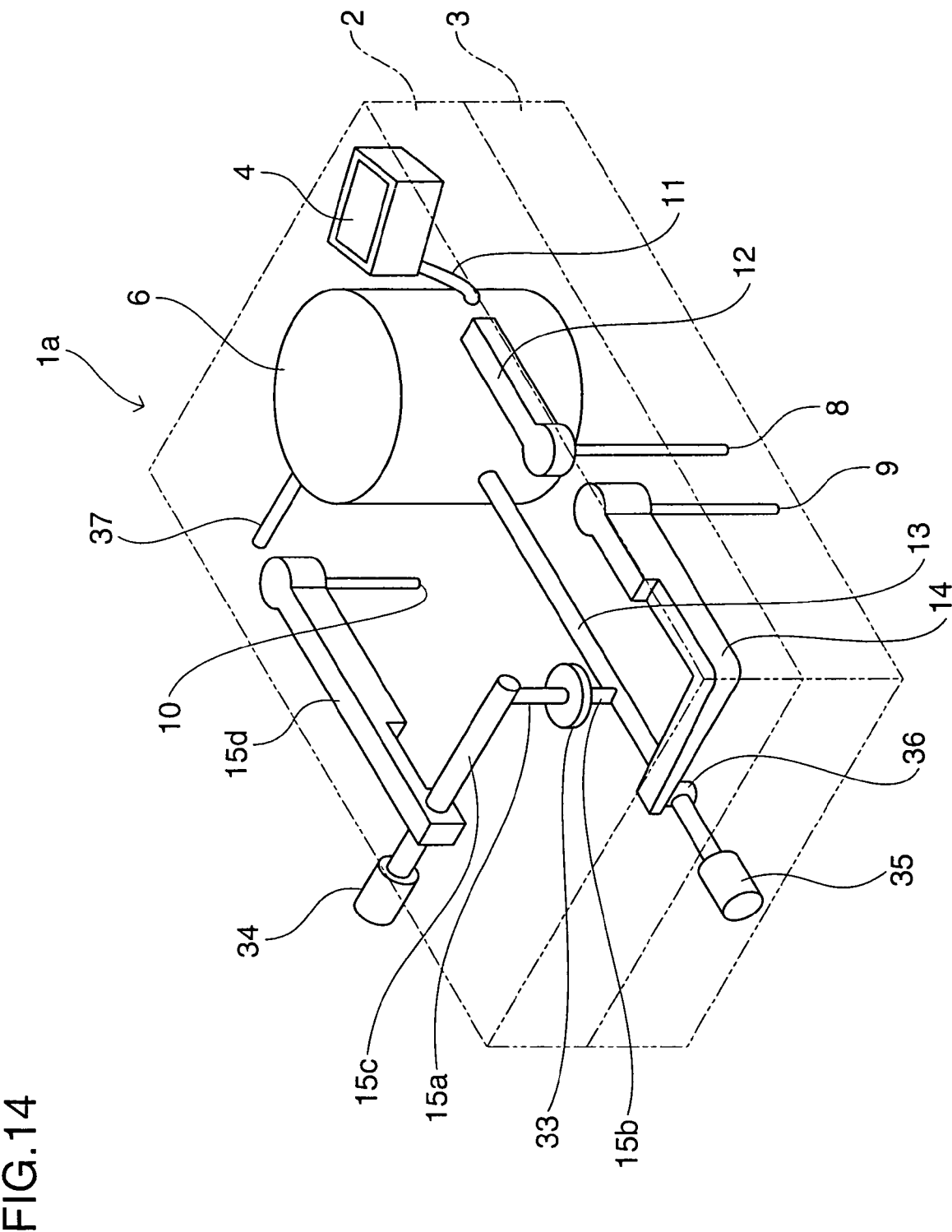
FIG. 14 is a perspective view illustrating the internal construction of the second measuring unit.

FIGS. 12 and 13 are a top plan view and a front view, respectively, of a second measuring unit for use in the blood analyzer according to the present embodiment for measurement of white blood cells. FIG. 14 is a perspective view illustrating the internal construction of the second measuring unit.

As shown in FIGS. 12 to 14, the second measuring unit (hereinafter referred to simply as "second unit") 1*a* includes an upper plate 2 and a lower plate 3. A bar code label BL for identification of the second unit 1*a* is applied on an upper surface of the upper plate 2. The second unit 1*a* includes: a sample receiving section 4 having a volume of 200 μL for receiving a sample; a rotary valve 6 including a diluent container 5 incorporated therein, and having a sample metering function and a flow path switching function; an electrical resistance measuring chamber 7; and first, second and third pump connection ports (pressure introduction port) 8, 9, 10. Further, the second unit 1*a* includes positioning throughholes 41, 42, 43 for properly positioning the second unit 1*a* with respect to the blood analyzer to be described later.

The sample receiving section 4 has a sample injection port provided on the top thereof, and the bottom thereof is connected to the rotary valve 6 via a channel 11. The pump connection port 8 is connected to the rotary valve 6 via a channel 12. The electrical resistance measuring chamber 7 is connected to the rotary valve 6 via a channel 13, to the pump connection port 9 via a channel 14, and to the pump connection port 10 via a channel 15*d*. The pump connection ports 8, 9, 10 each have a pipe projecting from a lower surface of the second unit 1*a* (FIG. 13). A vent hole 37 is provided for opening the rotary valve 6 to the atmosphere (FIG. 12).

As will be detailed later, the channels 11, 12 constitute a metering channel for introducing the sample into a sample metering section. The channel 13 constitutes a measuring channel for introducing a diluted sample from the diluent container 5 into the electrical resistance measuring chamber 7. Further, the channels 13, 14 constitute an agitation channel for agitating a mixture of the metered sample and a diluent for preparation of the diluted sample. The channel 15*d* allows the electrical resistance measuring chamber 7 and the pump connection port 10 to communicate with each other, and constitutes a retention channel for retaining the diluted sample introduced therein after measurement.

As shown in FIGS. 14 and 55, the channel 14 has a slant interior portion 14*a* and a stepped interior portion 14*b*, so that the sectional area thereof becomes greater toward the pump connection port 9. With this arrangement, bubbles generated when the mixture of the metered sample and the diluent is moved back and forth in arrow directions A and B for agitation thereof are prevented from flowing back to the diluent container 5 (i.e., in the arrow direction B). Thus, the bubbles are prevented from being contained in the diluted sample.

As shown in FIGS. 14 and 56, the channel 15*d* has a portion 15*f* having a sufficiently smaller sectional area than an internal channel 15*c* provided in the electrical resistance measuring chamber 7. With this arrangement, bubbles generated in the vicinity of an electrode (to be described later) of the electrical resistance measuring chamber 7 when a flow rate in the channel 15*d* is increased are sucked together with the diluted sample in an arrow direction C, so that the electrical resistance measuring chamber 7 is not influenced by the bubbles during the measurement.

A-2-2. Construction of Rotary Valve

FIGS. 4, 5 and 6 are a top plan view, a front view and a bottom view, respectively, of the rotary valve 6. As shown in FIGS. 4 to 6, the rotary valve 6 includes an outer cylinder 16 having an open bottom, and an inner cylinder 17 having a closed bottom and inserted in the outer cylinder 16 from the open bottom of the outer cylinder 16. The inner cylinder 17 has an open top, and a flange 18 provided at the bottom thereof.

Two projections 19, 20 project downward from the flange 18 to define a groove 21 having non-parallel edges therebetween. The projections 19, 20 constitute a connector to be connected to a valve driving source to be described later. When the inner cylinder 17 is rotated about an axis thereof, an outer circumferential surface of the inner cylinder 17 is slidable in contact with an inner circumferential surface of the outer cylinder 16. Although the groove 21 has the non-parallel edges in this embodiment, the groove 21 may have parallel edges.

FIGS. 7, 8 and 9 are sectional views of the rotary valve 6 as seen in arrow directions A-A, B-B and C-C, respectively, in FIG. 5. FIG. 10 is a sectional view of the rotary valve 6 as seen in an arrow direction X-X in FIG. 4. As shown in FIG. 7, the inner cylinder 17 has two through-holes 22, 23 formed in an upper portion thereof for opening and closing the vent hole 37, and the outer cylinder 16 has a through-hole 38 communicating with the vent hole 37.

As shown in FIG. 8, the inner cylinder 17 has three elongated lateral grooves 24, 25, 26 formed in circumferentially aligned relation in a middle portion of the outer circumferential surface thereof, and the outer cylinder 16 has three through-holes 27, 28 and 29 communicating with the channels 11, 12 and 13, respectively.

As will be described later, the lateral groove 25 serves as the sample metering section, and the lateral grooves 24, 26 serve as channel opening/closing grooves.

As shown in FIG. 9, the inner cylinder 17 has two throughholes 30, 31 formed in a lower portion thereof for channel opening and closing. As shown in FIGS. 8 to 10, the outer cylinder 16 further has an elongated vertical groove 32 formed in the inner circumferential surface thereof as extending axially from a middle portion to a lower portion thereof.

A-2-3. Construction of Electrical Resistance Measuring Chamber

As shown in FIGS. 12 and 14, the electrical resistance measuring chamber 7 includes a disk pellet (separation plate) 33 provided between vertical portions 15a and 15b of the internal channel 15c thereof, an electrode 34 provided in a junction between the channels 15d and 15c with a distal end thereof exposed to the inside of the channel junction, and an electrode 35 provided in a junction 36 between the channels 13 and 14 with a distal end thereof exposed to the inside of the channel junction.

FIG. 11 is a sectional view illustrating a major portion of the electrical resistance measuring chamber 7. The pellet 33 is fitted in a round recess formed in the lower plate 3 coaxially with the vertical portion 15b and pressed by a round projection provided on the upper plate 2 coaxially with the vertical portion 15a.

The pellet 33 has a minute through-hole (orifice) 33a formed in the center thereof, so that the electrical resistance of an electrolytic solution passing through the minute through-hole 33a is measured by the electrodes 34, 35. The pellet 33 is formed of a polyetherimide sheet having a thickness of 125 μm. The minute through-hole 33a is formed in the sheet as having a diameter of 100 μm by an excimer laser.

A-3. Third Measuring Unit
A-3-1. Construction of Third Measuring Unit

Figure 15:
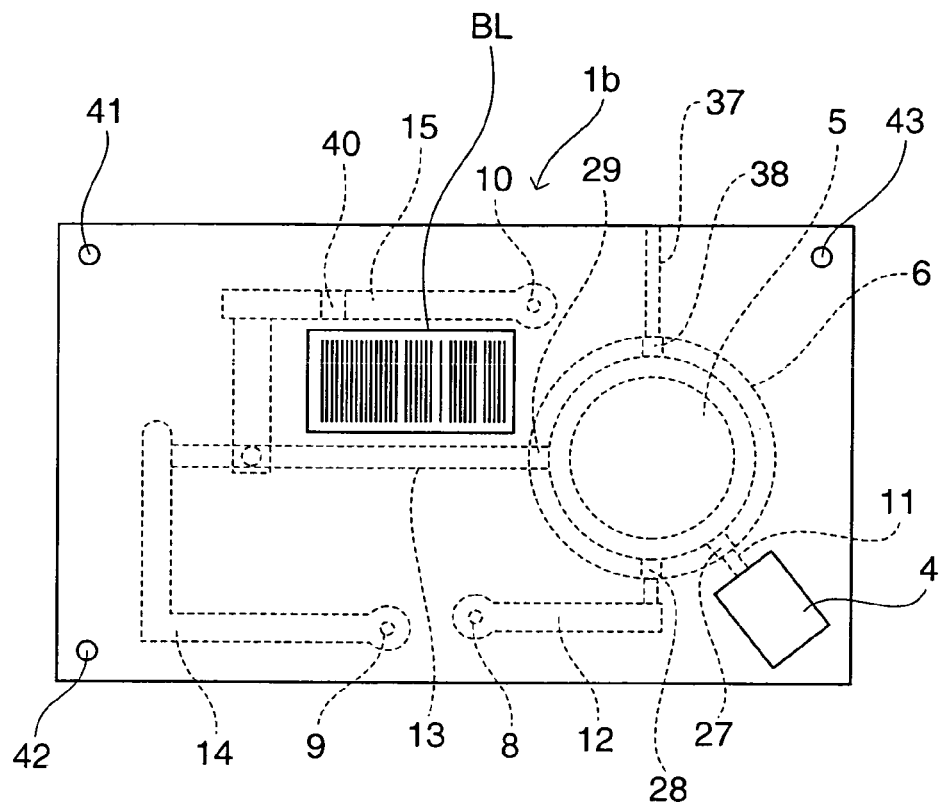
FIG. 15 is a top plan view of the third measuring unit for use in the blood analyzer according to the present embodiment.
Figure 16:
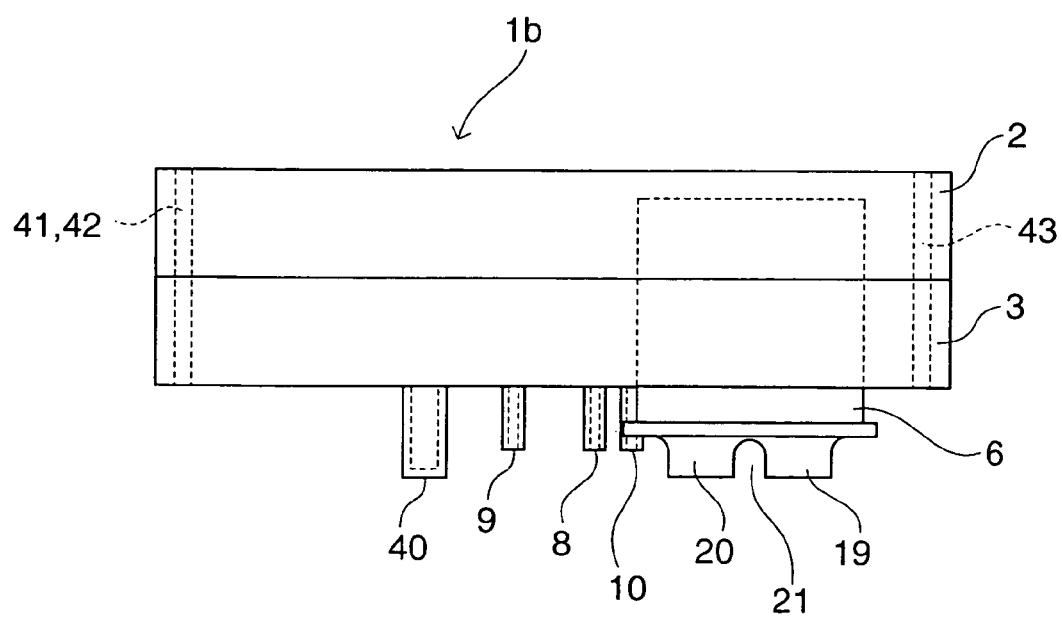
FIG. 16 is a front view of the third measuring unit.
Figure 17:
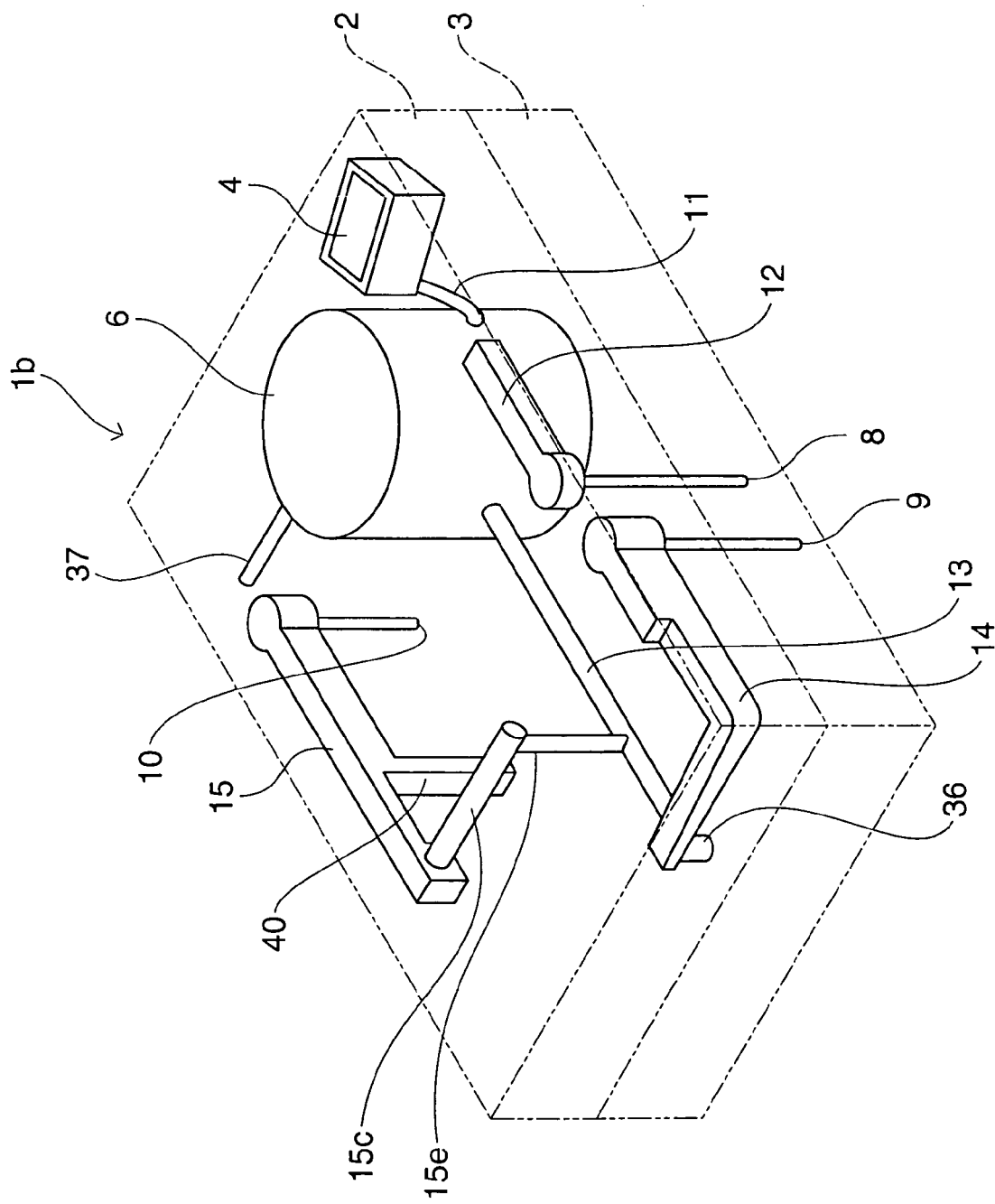
FIG. 17 is a perspective view illustrating the internal construction of the third measuring unit.

FIGS. 15 and 16 are a top plan view and a front view, respectively, of a third measuring unit for use in the blood analyzer according to the present embodiment for measurement of hemoglobin. FIG. 17 is a perspective view illustrating the internal construction of the third measuring unit.

As shown in FIGS. 15 to 17, the third measuring unit (hereinafter referred to simply as "third unit") 1b includes an upper plate 2 and a lower plate 3. A bar code label BL for identification of the third unit 1b is applied on an upper surface of the upper plate 2. The third unit 1b includes: a sample receiving section 4 having a volume of 200 μL for receiving a sample; a rotary valve 6 including a diluent container 5 incorporated therein, and having a sample metering function and a flow path switching function; and first, second and third pump connection ports (pressure introduction port) 8, 9, 10. Further, the third unit 1b includes positioning through-holes 41, 42, 43 for properly positioning the third unit 1b with respect to the blood analyzer to be described later.

The sample receiving section 4 has a sample injection port provided on the top thereof, and the bottom thereof is connected to the rotary valve 6 via a channel 11. The pump connection port 8 is connected to the rotary valve 6 via a channel 12. The rotary valve 6 is connected to the pump connection port 9 via channels 13, 14, and to the pump connection port 10 via channels 13, 15e, 15c, 15. A transparent absorbance measuring chamber 40 is provided in the midst of the channel 15 as projecting from a lower surface of the third unit 1b as shown in FIG. 16. The pump connection ports 8, 9, 10 each have a pipe projecting from the lower surface of the third unit 1b (FIG. 16). A vent hole 37 is provided for opening the rotary valve 6 to the atmosphere (FIG. 15).

As will be detailed later, the channels 11, 12 constitute a metering channel for introducing the sample into a sample metering section. The channel 13 constitutes a measuring channel for introducing a diluted sample from the diluent container 5 into the electrical resistance measuring chamber 7. Further, the channels 13, 14 constitute an agitation channel for agitating a mixture of the metered sample and a diluent for preparation of the diluted sample. The channel 15 constitutes a retention channel for retaining the diluted sample introduced therein after measurement.

As shown in FIGS. 17 and 55, the channel 14 has a slant interior portion 14a and a stepped interior portion 14b, so that the sectional area thereof becomes greater toward the pump connection port 9. With this arrangement, bubbles generated when the mixture of the metered sample and the diluent is moved back and forth in arrow directions A and B for agitation thereof are prevented from flowing back to the diluent container 5 (i.e., in the arrow direction B). Thus, the bubbles are prevented from being contained in the diluted sample.

A-3-2. Construction of Rotary Valve

FIGS. 4, 5 and 6 are a top plan view, a front view and a bottom view, respectively, of the rotary valve 6. As shown in FIGS. 4 to 6, the rotary valve 6 includes an outer cylinder 16 having an open bottom, and an inner cylinder 17 having a closed bottom and inserted in the outer cylinder 16 from the open bottom of the outer cylinder 16. The inner cylinder 17 has an open top, and a flange 18 provided at the bottom thereof.

Two projections 19, 20 project downward from the flange 18 to define a groove 21 having non-parallel edges therebetween. The projections 19, 20 constitute a connector to be connected to a valve driving source to be described later. When the inner cylinder 17 is rotated about an axis thereof, an outer circumferential surface of the inner cylinder 17 is slidable in contact with an inner circumferential surface of the outer cylinder 16. Although the groove 21 has the non-parallel edges in this embodiment, the groove 21 may have parallel edges.

FIGS. 7, 8 and 9 are sectional views of the rotary valve 6 as seen in arrow directions A-A, B-B and C-C, respectively, in FIG. 5. FIG. 10 is a sectional view of the rotary valve 6 as seen in an arrow direction X-X in FIG. 4. As shown in FIG. 7, the inner cylinder 17 has two through-holes 22, 23 formed in an upper portion thereof for opening and closing the vent hole 37, and the outer cylinder 16 has a through-hole 38 communicating with the vent hole 37.

As shown in FIG. 8, the inner cylinder 17 has three elongated lateral grooves 24, 25, 26 formed in circumferentially aligned relation in a middle portion of the outer circumferential surface thereof, and the outer cylinder 16 has three through-holes 27, 28 and 29 communicating with the channels 11, 12 and 13, respectively.

As will be described later, the lateral groove 25 serves as the sample metering section, and the lateral grooves 24, 26 serve as channel opening/closing grooves.

As shown in FIG. 9, the inner cylinder 17 has two through-holes 30, 31 formed in a lower portion thereof for channel opening and closing. As shown in FIGS. 8 to 10, the outer cylinder 16 further has an elongated vertical groove 32 formed in the inner circumferential surface thereof as extending axially from a middle portion to a lower portion thereof.

B. Blood Analyzer
B-1. Construction of Blood Analyzer

Figure 18:
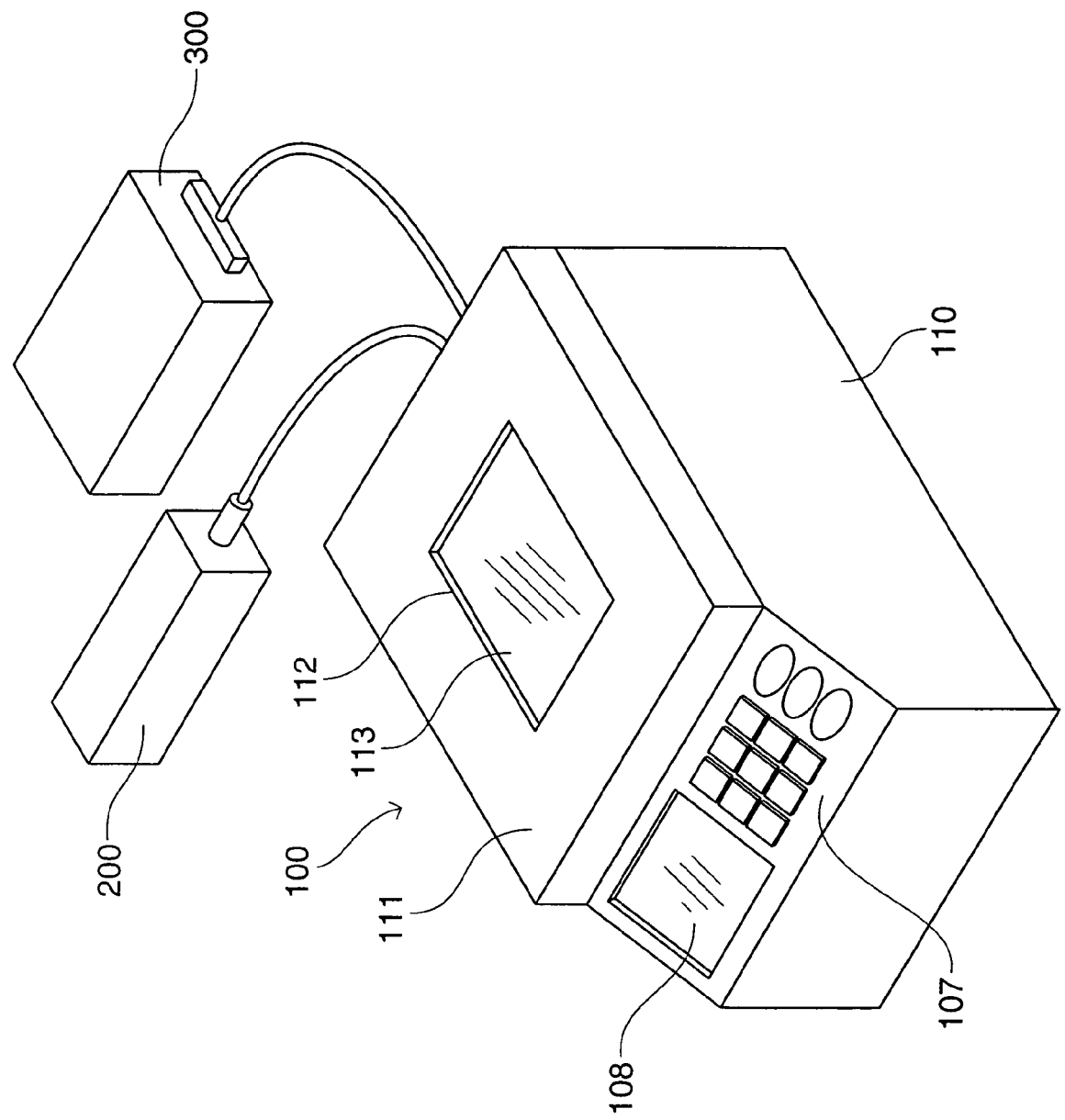
FIG. 18 is a perspective view of the blood analyzer according to the present embodiment.

FIG. 18 is a perspective view illustrating the blood analyzer according to the present embodiment. The blood analyzer includes a main body 100, and a bar code reader 200 and a printer 300 connected to the main body 100 by cables. The main body 100 includes a measuring section 110, and a cover 111 openably provided on an upper face of the measuring section 110. The measuring section 110 includes an input section (key board) 107 and a display device (LCD) 108 provided on a front face thereof.

Figure 19:
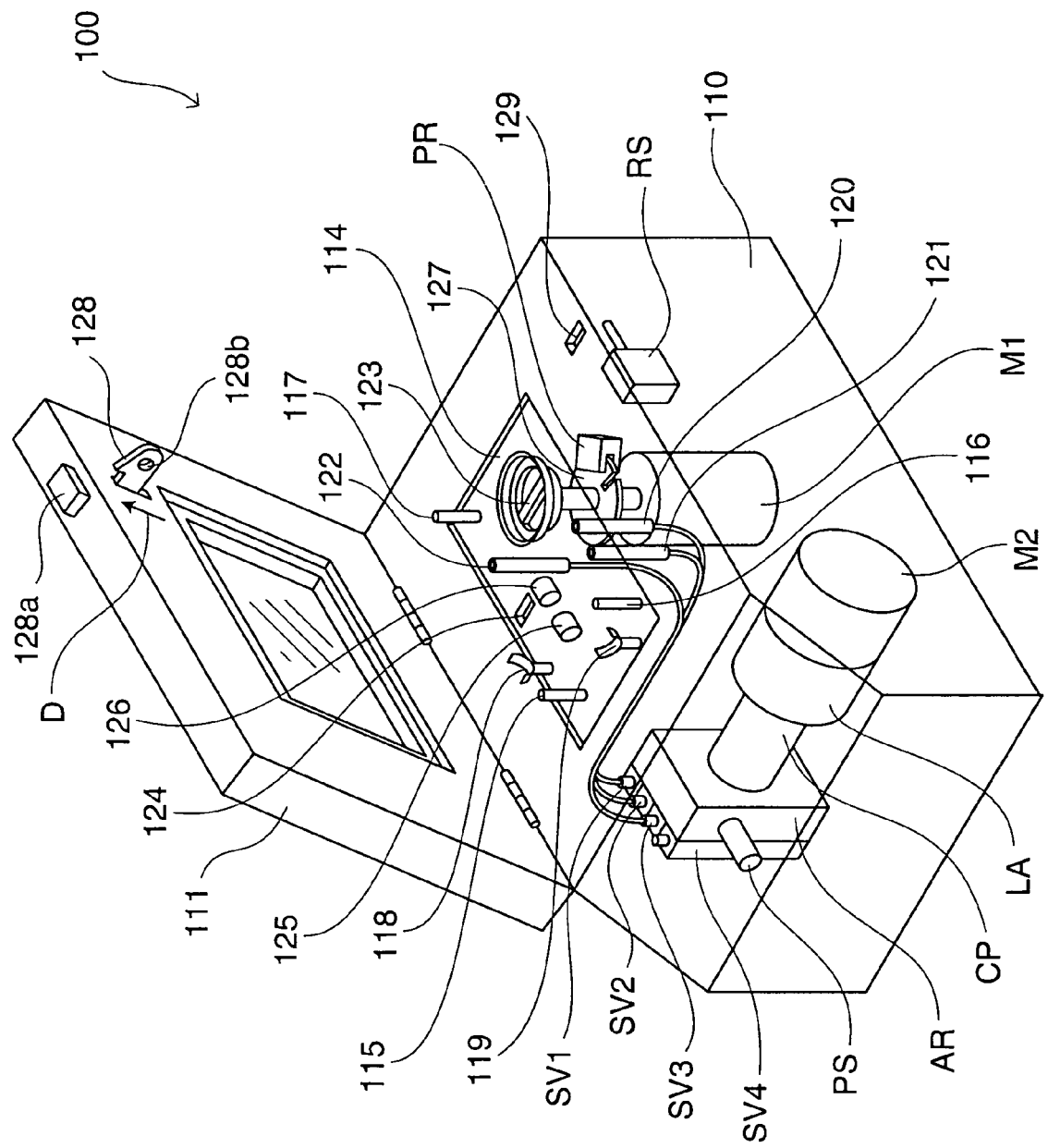
FIG. 19 is a diagram for explaining the construction of the analyzer of FIG. 18.
Figure 20:
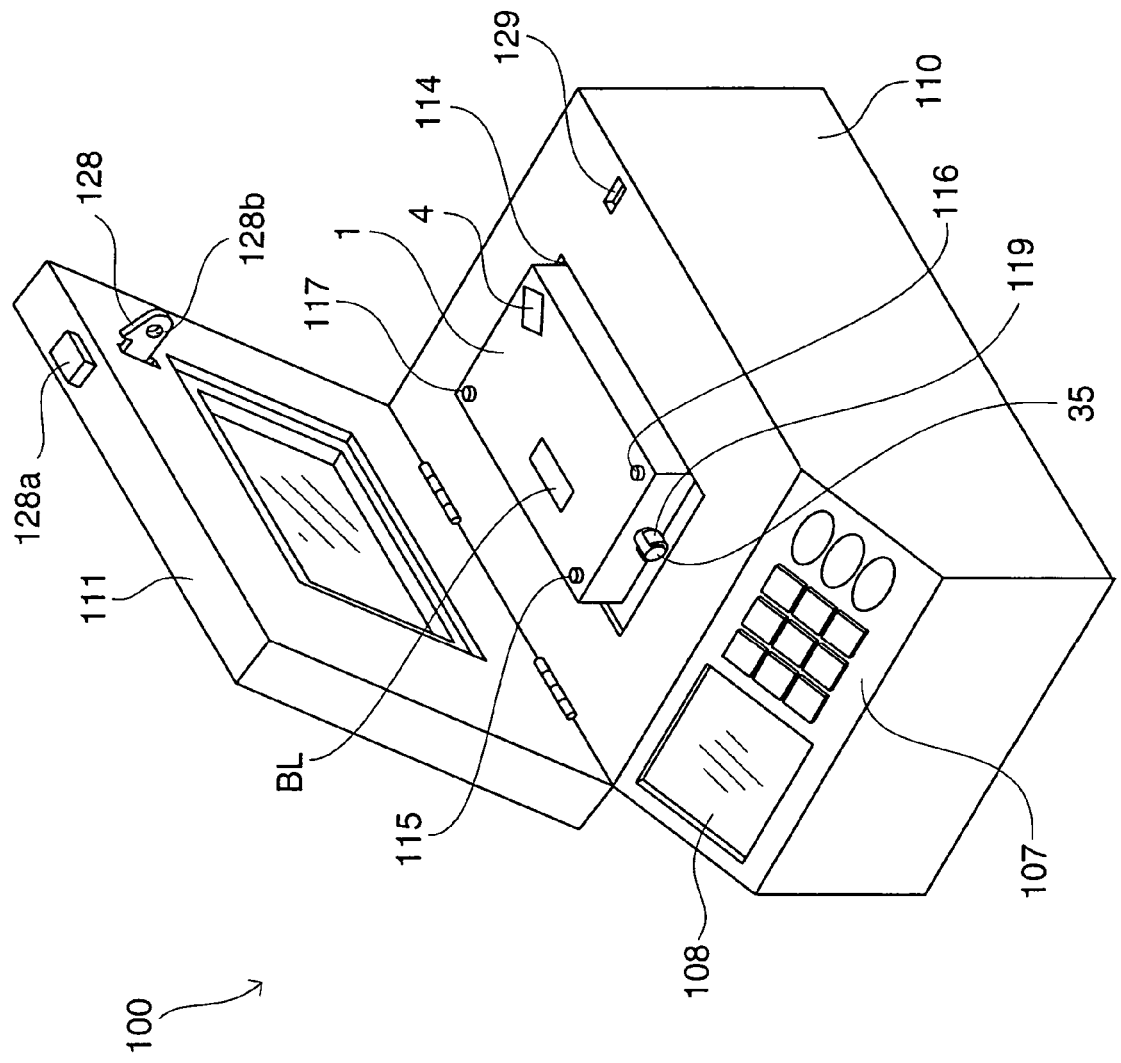
FIG. 20 is a diagram for explaining how to use the analyzer of FIG. 18.

FIG. 19 is a diagram for explaining the construction of the main body 100, and FIG. 20 is a perspective view illustrating the main body 100 in which the first unit 1, the second unit 1a or the third unit 1b is set. An accommodation section 114 in which the first unit 1, the second unit 1a or the third unit 1b is removably set is provided in the upper face of the measuring section 110 shown in FIG. 19. Positioning pins 115, 116 and 117 to be respectively inserted in the through-holes 41, 42 and 43 (FIGS. 1, 12, 15) are provided in the accommodation section 114 as projecting vertically upright. The accommodation section 114 includes electrode contacts 118 and 119 to be respectively brought into contact with the electrodes 34 and 35 (FIGS. 1, 12), pipe connectors 120, 121 and 122 to be respectively connected to the pipes of the pump connection ports 8, 9 and 10 (FIGS. 3, 14, 17), a connection disk 123 having a projection to be fitted with the groove 21 of the rotary valve 6 (FIGS. 5, 13, 16) and detachably connected to the inner cylinder 17, and an opening 124 for receiving the absorbance measuring chamber 40 (FIGS. 2, 16).

A laser diode 125 for emitting a laser beam toward the absorbance measuring chamber 40 of the first unit 1 or the third unit 1b, and a photodiode 126 for receiving light transmitted through the absorbance measuring chamber 40 are provided below the opening 124 in the measuring section 110. The connection disk 123 is fixed to a distal end of an output shaft of a stepping motor M1, and a slit disk 127 for detecting a rotation angle is fitted around the output shaft of the stepping motor M1. A photo-interrupter PR for detecting the position of a slit of the slit disk 127 is provided in proximity to the slit disk 127.

The measuring section 110 further includes an air chamber AR, a syringe pump CP for applying a negative pressure or a positive pressure to the air chamber AR, a stepping motor M2, and a linear actuator LA which actuates the syringe pump CP by converting the rotation of the stepping motor M2 into a linear motion of the syringe pump CP. Electromagnetic valves SV1 to SV5 are provided in the vicinity of the air chamber AR. A peristaltic pump may be used in place of the syringe pump CP and the linear actuator LA.

The air chamber AR is connected to the pipe connectors 121, 120 and 122 via the electromagnetic valves SV1, SV2 and SV3, respectively, and is opened to the atmosphere via the electromagnetic valve SV4. A tube connecting the electromagnetic valve SV1 to the pipe connector 121 is opened to the atmosphere via the electromagnetic valve SV5. The air chamber AR includes a pressure sensor PS for detecting the inside pressure of the air chamber AR.

The cover 111 has an engagement piece 128 provided on a surface thereof to be mated with the upper face of the measuring section 110. The engagement piece 128 is biased in an arrow direction D by a spring not shown. When the unit 1, 1a or 1b is set in the accommodation section 114 and the cover 111 is closed, the engagement piece 128 is engaged with an opening 129 formed in the upper face of the measuring section 110 to keep the cover 111 in a closed state. A button 128a for disengaging the engagement piece 128 from the opening 129 is provided on a side face of the cover 111.

A solenoid RS for locking the engagement piece 128 to the opening 129 is provided below the opening 129. When the solenoid RS is actuated, an actuator of the solenoid RS is inserted into a lateral hole 128b of the engagement piece 128. Instead of the solenoid RS, an electromagnetic valve or the like may be employed for keeping the cover 111 in the closed state.

When the first unit 1 is to be set in the accommodation section 114, the first unit 1 is placed in the accommodation section 114 on the upper face of the measuring section 110 with the positioning pins 115, 116 and 117 respectively fitted in the positioning through-holes 41, 42 and 43 of the first unit 1 (FIG. 1) as shown in FIG. 20, and then the cover 111 is closed.

The first unit 1 is pressed by the cover 111, whereby the pipes of the pump connection ports 8, 9 and 10 are respectively inserted into the pipe connectors 120, 121 and 122 and air-tightly connected to the pipe connectors 120, 121 and 122 via O-rings fitted in the pipe connectors 120, 121 and 122. At the same time, the absorbance measuring chamber 40 is moved downward between the laser diode 125 and the photodiode 126, and the inner cylinder 17 of the rotary valve 6 (FIG. 4) is connected to the connection disk 123. Further, the electrodes 34 and 35 are respectively brought into contact with the electrode contacts 118 and 119.

When the second unit 1a is to be set in the accommodation section 114, the second unit 1a is placed in the accommodation section 114 on the upper face of the measuring section 110 with the positioning pins 115, 116 and 117 respectively fitted in the positioning through-holes 41, 42 and 43 of the second unit 1a (FIG. 12) as shown in FIG. 20, and then the cover 111 is closed.

The second unit 1a is pressed by the cover 111, whereby the pipes of the pump connection ports 8, 9 and 10 are respectively inserted into the pipe connectors 120, 121 and 122 and air-tightly connected to the pipe connectors 120, 121 and 122 via O-rings fitted in the pipe connectors 120, 121 and 122. At the same time, the inner cylinder 17 of the rotary valve 6 is connected to the connection disk 123, and the electrodes 34 and 35 are respectively brought into contact with the electrode contacts 118 and 119.

When the third unit 1b is to be set in the accommodation section 114, the third unit 1b is placed in the accommodation section 114 on the upper face of the measuring section 110 with the positioning pins 115, 116 and 117 respectively fitted in the positioning through-holes 41, 42 and 43 of the third unit 1b (FIG. 15) as shown in FIG. 20, and then the cover 111 is closed.

The third unit 1b is pressed by the cover 111, whereby the pipes of the pump connection ports 8, 9 and 10 are respectively inserted into the pipe connectors 120, 121 and 122 and air-tightly connected to the pipe connectors 120, 121 and 122 via O-rings fitted in the pipe connectors 120, 121 and 122. At the same time, the inner cylinder 17 of the rotary valve 6 is connected to the connection disk 123, and the absorbance measuring chamber 40 is moved downward between the laser diode 125 and the photodiode 126.

B-2. Control Circuit and Fluid Circuit

Figure 21:
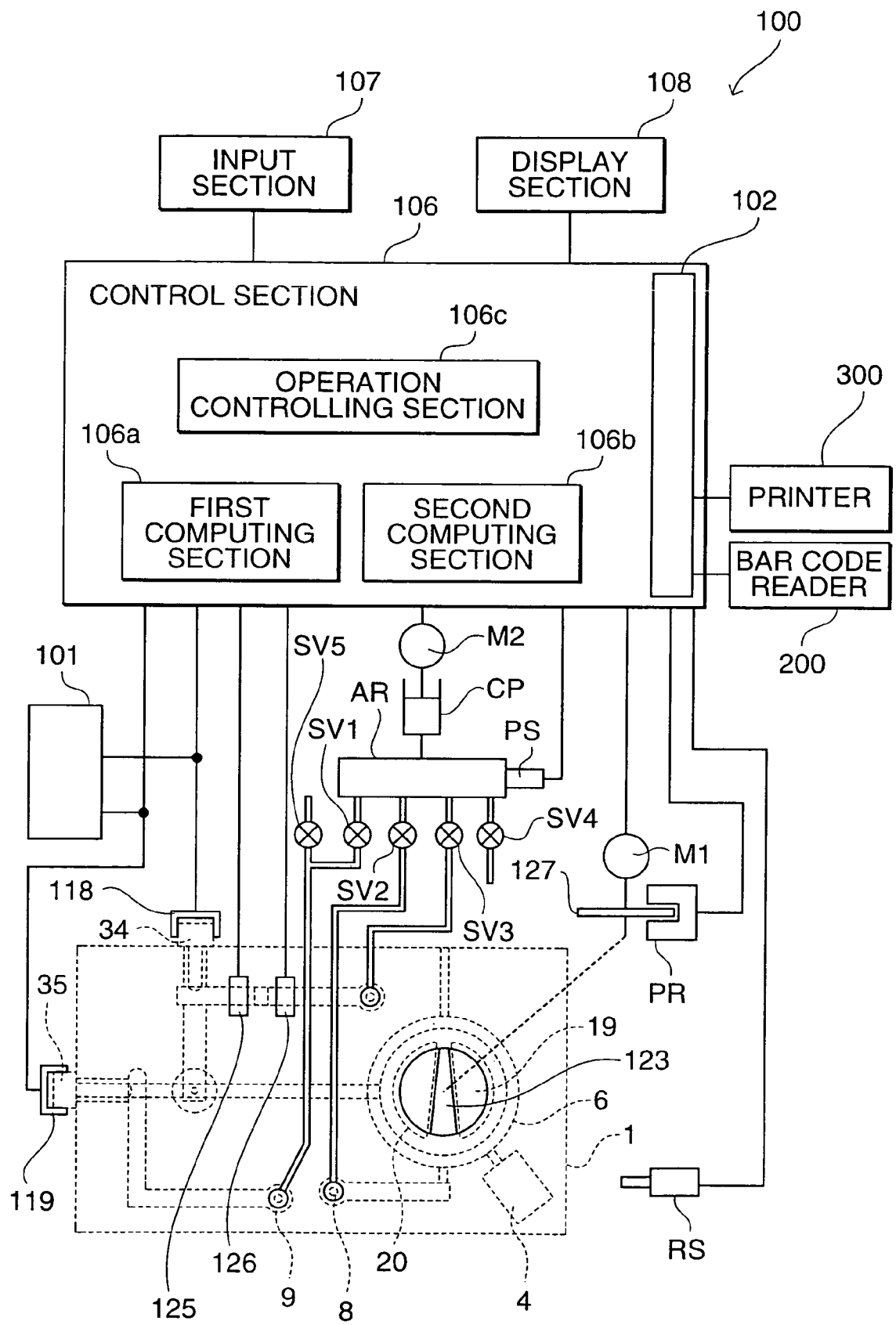
FIG. 21 is a block diagram illustrating the construction of the analyzer of FIG. 18 in which the first measuring unit is set.

FIG. 21 is a block diagram illustrating a control circuit and a fluid circuit established when the first unit 1 is set in the main body 100. In FIG. 21, an output of a constant direct current source 101 is connected to the electrodes 34 and 35 of the first unit 1 via the contacts 118 and 119, respectively.

Figure 22:
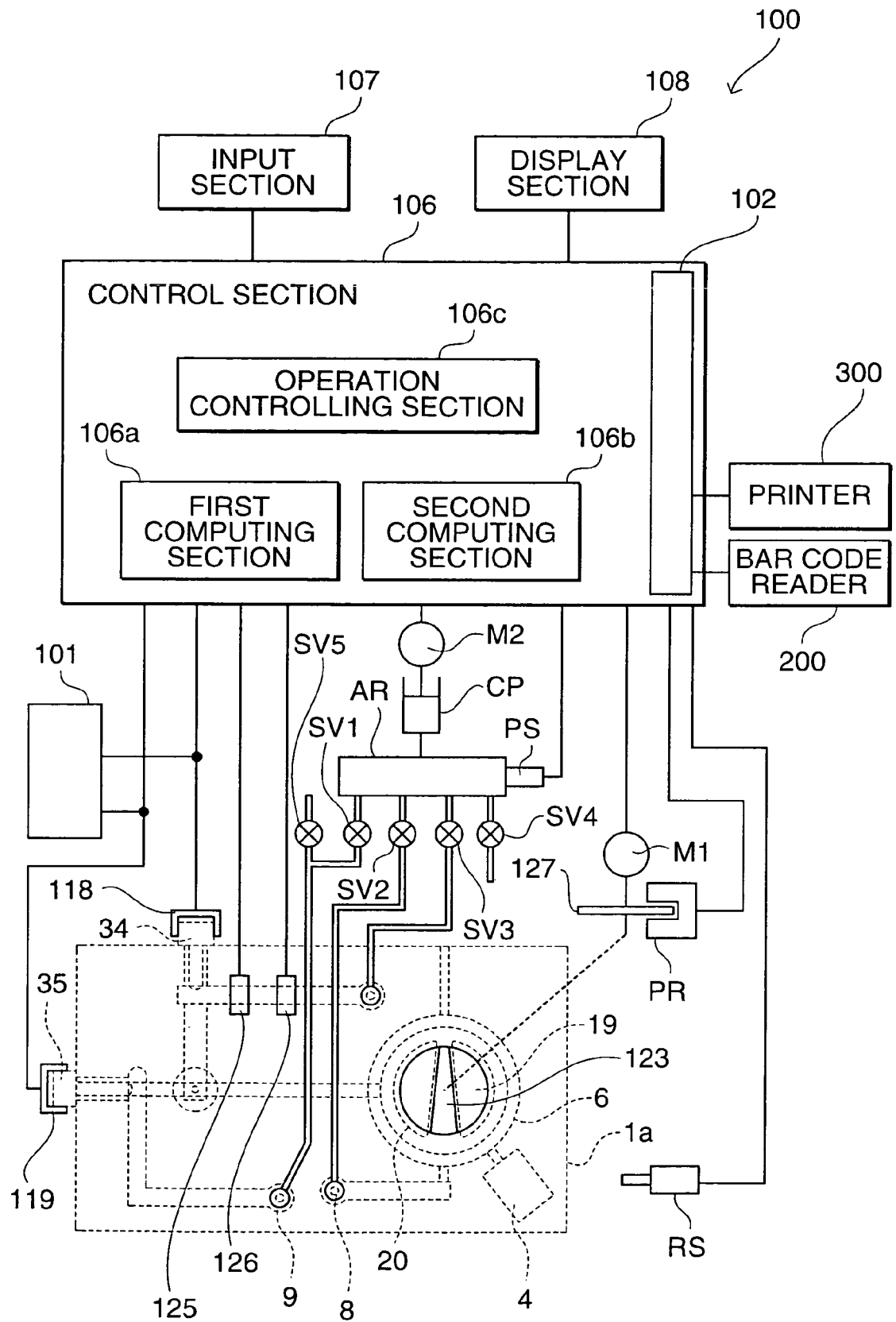
FIG. 22 is a block diagram illustrating the construction of the analyzer of FIG. 18 in which the second measuring unit is set.

FIG. 22 is a block diagram illustrating a control circuit and a fluid circuit established when the second unit 1a is set in the main body 100. In FIG. 22, the output of the constant direct current source 101 is connected to the electrodes 34 and 35 of the second unit 1a via the contacts 118 and 119, respectively.

Figure 23:
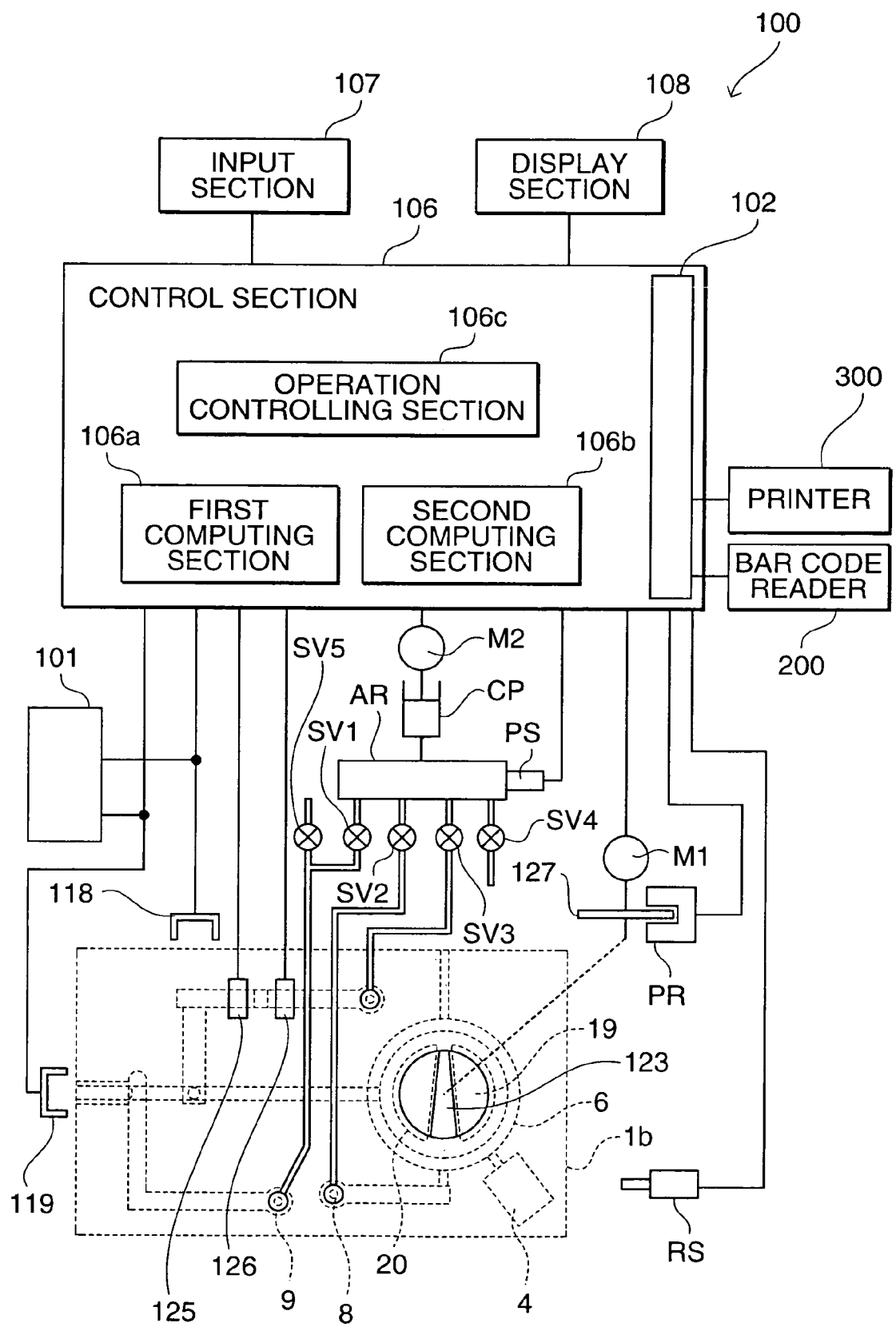
FIG. 23 is a block diagram illustrating the construction of the analyzer of FIG. 18 in which the third measuring unit is set.

FIG. 23 is a block diagram illustrating a control circuit and a fluid circuit established when the third unit 1b is set in the main body 100.

In FIGS. 21, 22 and 23, a control section 106 includes a microprocessor including a CPU, a ROM and a RAM, a driver circuit for driving the motors and the electromagnetic valves, and an external output port 102a. The ROM serving as a memory section has a plurality of analysis controlling programs stored therein for executing operations shown in the flowcharts of FIGS. 24 to 33 and FIGS. 87 to 99 in accordance with the type of the measuring unit set in the measuring section 110. The ROM, together with the CPU and the RAM, constitutes a first computing section 106a, a second computing section 106b and an operation controlling section 106c. The control section 106 performs signal processing operations upon reception of output signals from the input section 107, the electrodes 34, 35, the photodiode 126, the photo-interrupter PR, the bar code reader 200 and the pressure sensor PS, and outputs signals to the laser diode 125, the stepping motors M1, M2, the electromagnetic valves SV1 to SV5, the solenoid RS, the display section 108 and the printer 300. The first computing section 106a mainly receives signals from the electrodes 34, 35. The second computing section 106b mainly receives a signal from the photodiode 126. The first and second computing sections 106a, 106b perform analyzing operations. The operation controlling section 106c performs other controlling operations. The display section 108 may be a CRT or an LCD, and the printer 300 may be a thermal printer, a laser printer or an inkjet printer.

The electromagnetic valves SV1 to SV5 are of a constantly closed type, i.e., are constantly closed. The control section 106 is capable of transmitting and receiving signals with respect to an external information processing device, e.g., a personal computer, via an external output port 102. The constant direct current source 101 supplies a constant current to the electrolytic solution present between the electrodes 34 and 35 when the first unit 1 or the second unit 1a is set in the main body 100. Then, a potential difference between the electrodes 34 and 35 is inputted as a change in impedance (resistance) to the control section 106.

C. Measuring Operation

With reference to flow charts shown in FIGS. 24 to 27, FIGS. 28 to 30 and FIGS. 31 to 33, an explanation will hereinafter be given to the operation of the analyzer 100 shown in FIG. 18. FIGS. 34(a) to 38(a), FIGS. 34(b) to 38(b) and FIGS. 34(c) to 38(c) illustrate rotational positions of the inner cylinder 17 with respect to the outer cylinder 16 of the rotary valve 6. Particularly, FIGS. 34(a) to 38(a), FIGS. 34(b) to 38(b) and FIGS. 34(c) to 38(c) are sectional views of the rotary valve 6 as seen in arrow directions A-A, B-B and C-C, respectively, in FIG. 5.

A user sets the first unit 1, the second unit 1a or the third unit 1b in the measuring section 110 (FIG. 20 illustrates a case where the first unit 1 or the second unit 1a is set in the measuring section 110), and closes the cover 111 (Step S101, S102). At this time, the cover 111 is locked (Step S102a). The control section 106 checks the rotational position of the inner cylinder 17 by the photo-interrupter PR and, if necessary, drives the stepping motor M1 to rotate the inner cylinder 17 to an initial position (Step S103). Then, the user operates the input section 107 to input a command "PRESSURE TEST" (Step S104).

Thus, the syringe pump CP and the electromagnetic valves SV1 to SV5 are actuated. Then, the inside pressure of the air chamber AR is detected by the pressure sensor PS, and it is checked whether or not the respective components normally operate. If it is confirmed that all the components are normal, a message "PRESSURE TEST OK. PLEASE OPEN THE COVER AND INJECT A WHOLE BLOOD." is displayed on the display section 108 (Step S104a). The message displayed on the display section 108 in Step S104a may be printed using the printer 300. Then, the cover 111 is unlocked (Step S104b).

Subsequently, the user opens the cover 111, and reads the bar code label BL of the unit set in the measuring section 110 by means of the bar code reader 200 (Steps S105 and S106). Then, the user injects a whole blood sample into the sample injection port of the sample receiving section 4(Step S107).

In turn, the user closes the cover 111, and inputs a start command from the input section 107 (Steps S108, S109). The control section 106 judges the type of the unit set in the measuring section 110 on the basis of a bar code read by the bar code reader 200 (Steps S112 to S114). If the unit set in the measuring section 110 is classified into none of the known types of units and is judged to be unidentifiable, the measurement is interrupted and a message "UNIT UNIDENTIFIABLE. PLEASE SET ANOTHER UNIT." is displayed on the display section 108 (Step S115). The type of the unit may be input to the control section 106 through the input section 107.

C-1. Detailed Procedure for Pressure Test

A pressure test process in Steps S104, S104a will be described in detail with reference to flow charts shown in FIGS. 87 to 99.

Figure 24:
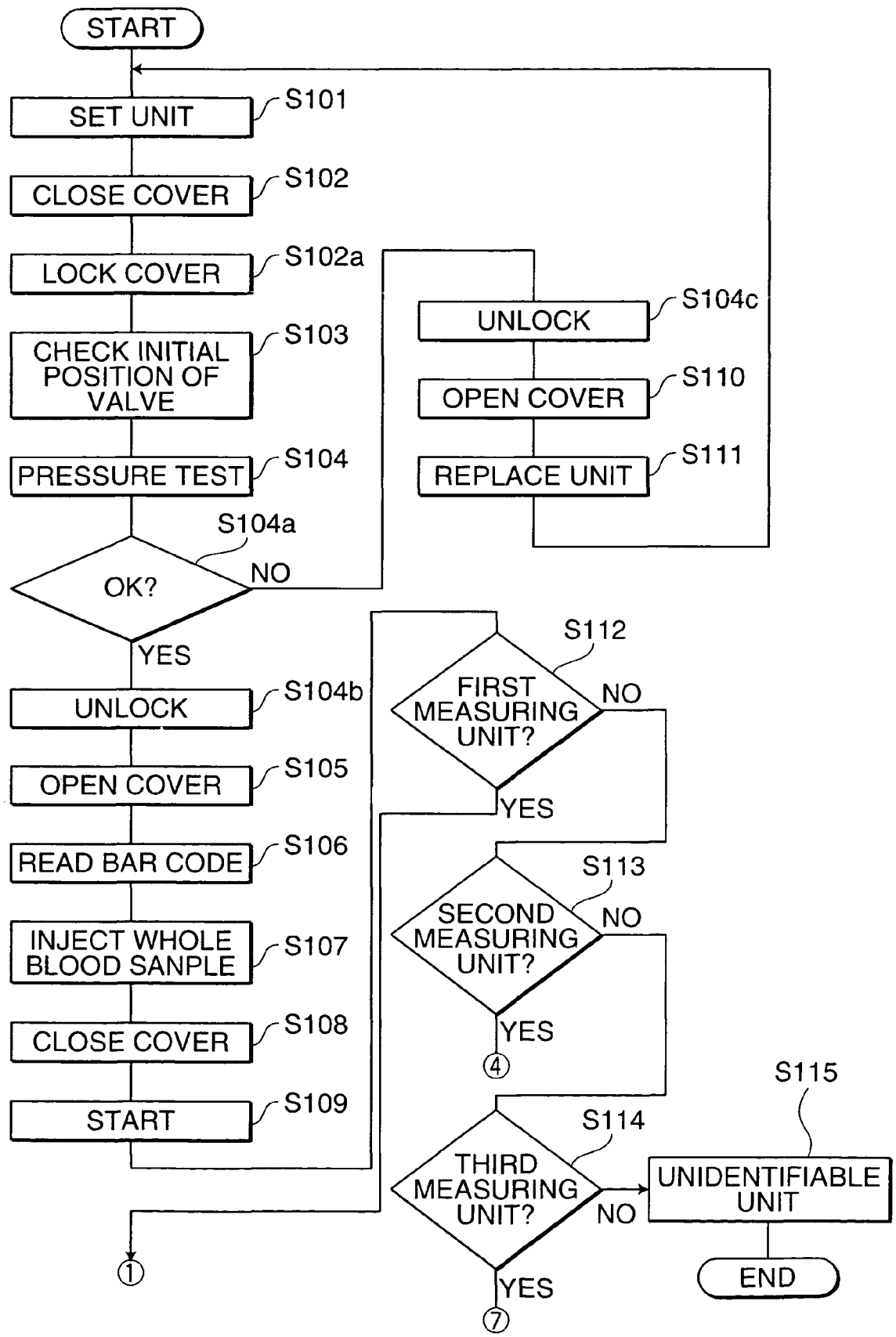
FIG. 24 is a flow chart for explaining an operation to be performed by the analyzer of FIG. 18.
Figure 87:
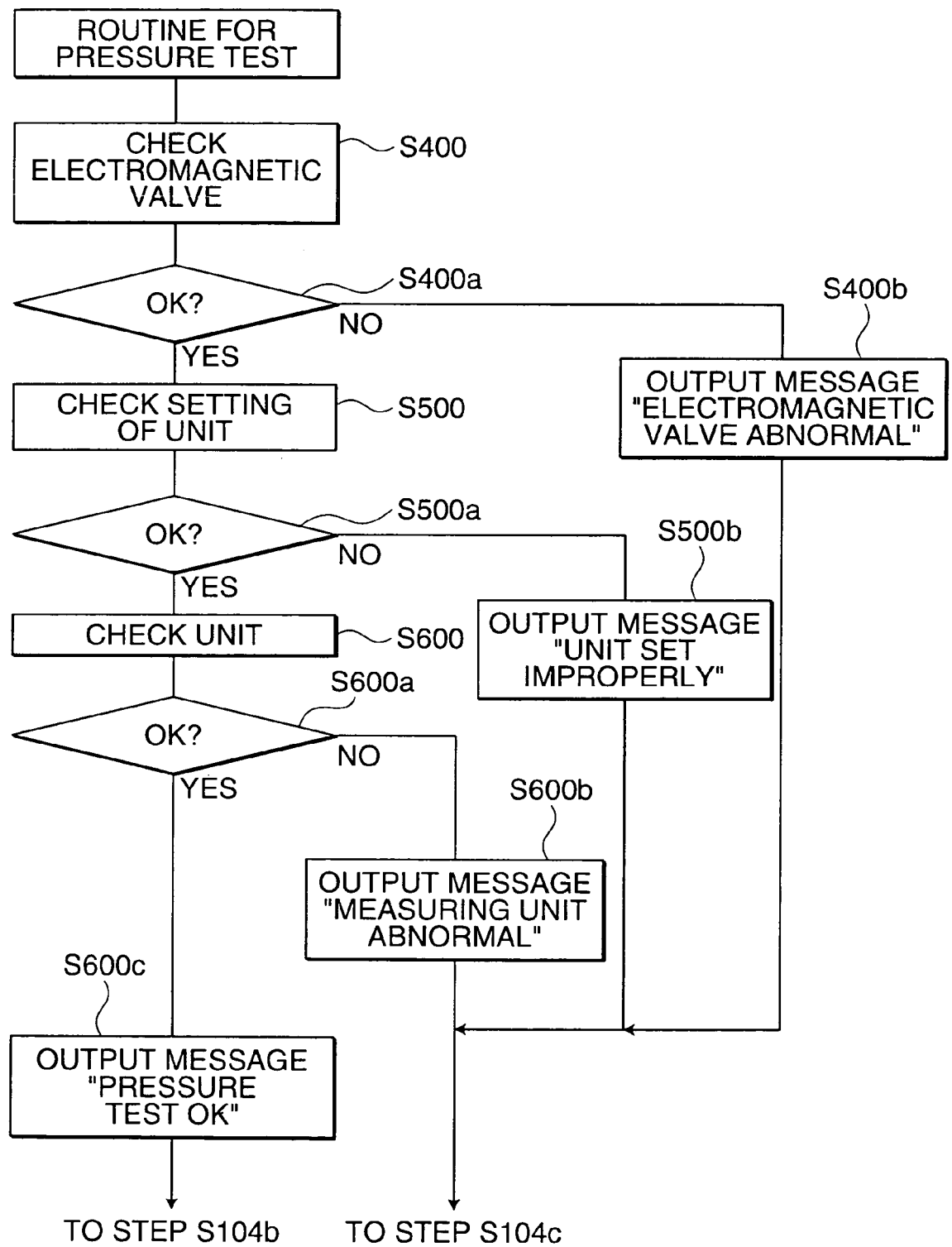
FIGS. 87 to 99 are flow charts for explaining the operation shown in FIG. 24 in greater detail.

In the pressure test process shown in FIG. 87, it is first checked whether or not the electromagnetic valves SV1 to SV5 operate normally (Step S400). If the electromagnetic valves SV1 to SV5 operate normally (OK in Step S400a), it is checked whether or not a measuring unit (the first, second or third measuring unit 1, 1a, 1b) is set properly (Step S500). If the measuring unit is set properly (OK in Step S500a), it is checked whether or not the measuring unit per se is normal (Step S600). If the measuring unit is normal (OK in Step S600a), the message "PRESSURE TEST OK" is displayed on the display section 108 (Step S600c), and the routine goes to Step S104b (FIG. 24). If the check result in Step S400a, S500a or S600a is negative (not OK), a message "ELECTROMAGNETIC VALVE ABNORMAL", "UNIT SET IMPROPERLY" or "MEASURING UNIT ABNORMAL" is displayed on the display section 108, and the routine goes to Step S104c (FIG. 24).

Then, the user opens the cover 111 (Step S110), and replaces or resets the measuring unit according to the displayed message (Step S111).

C-1-1. Check of Operation of Electromagnetic Valves

Figure 88:
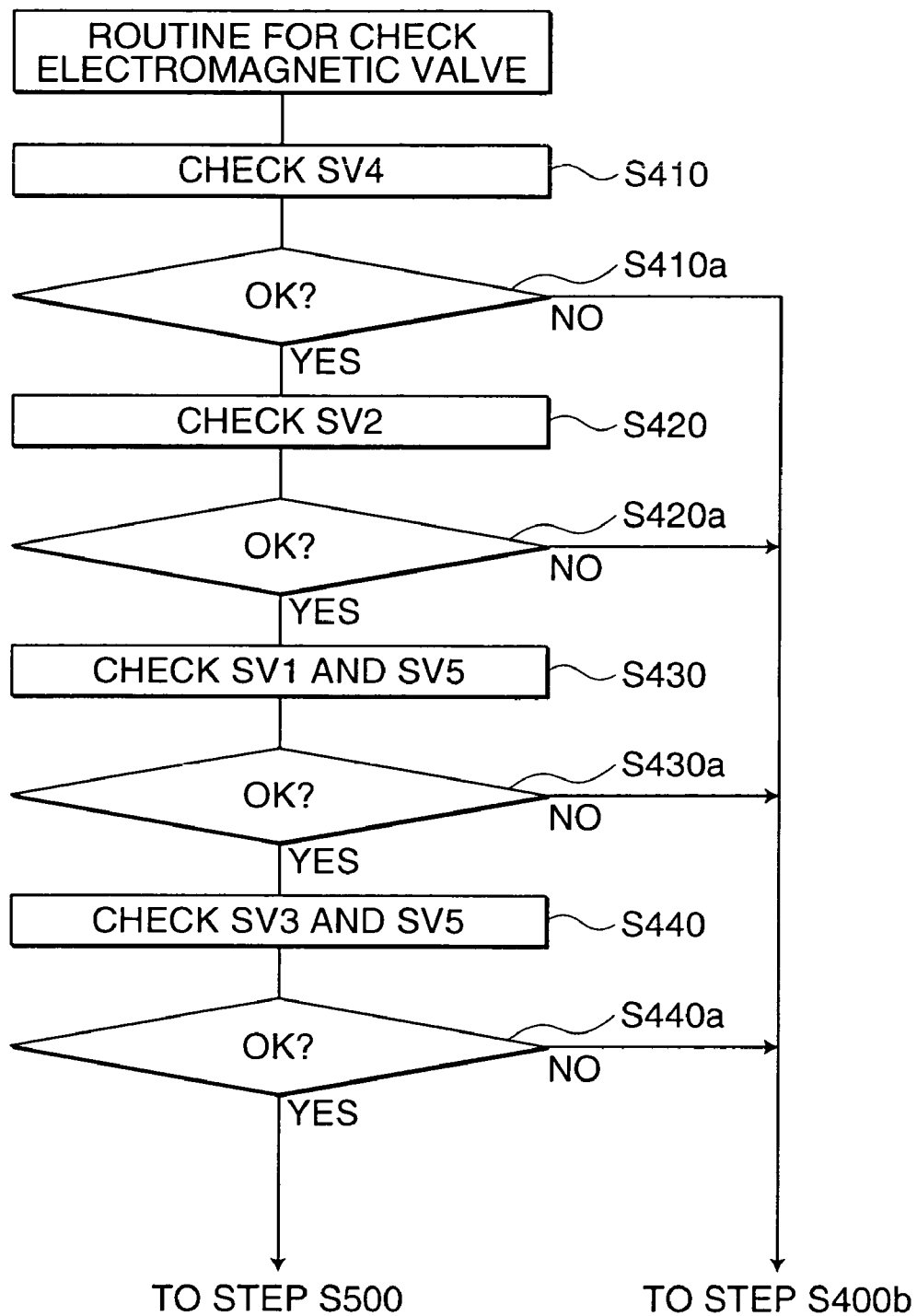

A detailed procedure (routine) for the check of the electromagnetic valves in Step S400 of FIG. 87 is shown in FIG. 88.

As shown in FIG. 88, it is sequentially checked whether or not the electromagnetic valve SV4 operates normally, whether or not the electromagnetic valve SV2 operates normally, whether or not the electromagnetic valves SV1 and SV5 operate normally, and whether or not the electromagnetic valves SV3 and SV5 operate normally (Steps S410, S420, S430, S440). If all the electromagnetic valves SV1 to SV5 operate normally (OK in Steps S410a, S420a, S430a, S440a), the routine goes to Step S500 (FIG. 87). If the check result in Step S410a, S420a, S430a or S440a is negative, the routine goes to Step S400b (FIG. 87).

Figure 89:
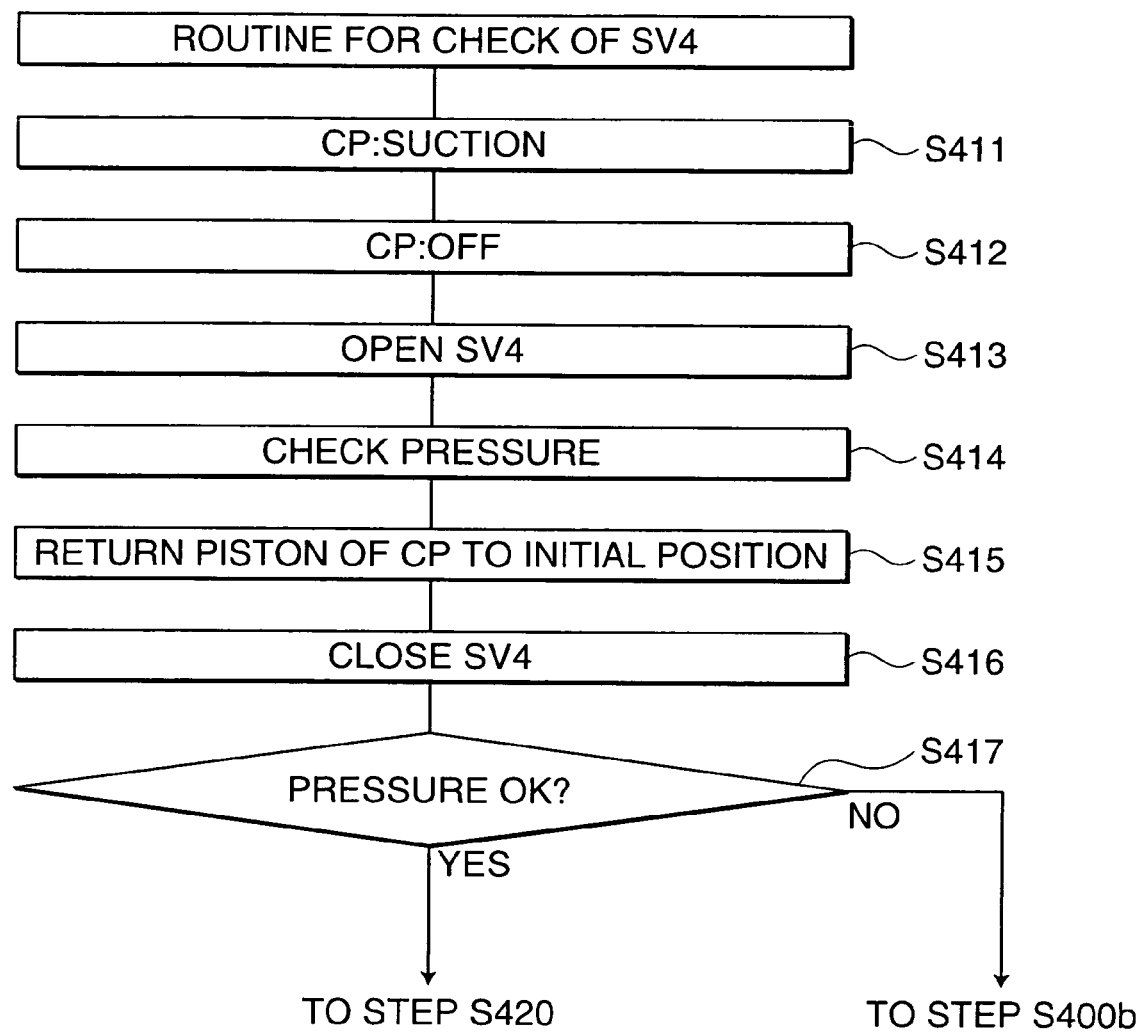

A detailed procedure (routine) for the check of the electromagnetic valve SV4 in Step S410 of FIG. 88 is shown in FIG. 89.

As shown in FIG. 89, the syringe pump CP is first actuated to perform the sucking operation to keep the air chamber AR at a negative pressure (Steps S411, S412). Then, the electromagnetic valve SV4 is opened, and it is checked whether or not the inside pressure of the air chamber AR detected by the pressure sensor PS returns to the atmospheric pressure within a predetermined period (Steps S413, S414). In turn, the piston of the syringe pump CP is returned to an initial position, and the electromagnetic valve SV4 is closed (Steps S415, S416). If the inside pressure of the air chamber AR returns to the atmospheric pressure in Step S414, the routine goes to Step S420 (FIG. 88). If the inside pressure of the air chamber AR does not return to the atmospheric pressure (Step S417), the routine goes to Step S400b (FIG. 87). This is because it is judged that the electromagnetic valve SV4 is not completely opened if the inside pressure of the air chamber AR does not return to the atmospheric pressure. On the other hand, it is judged that a predetermined amount of air is passed through the electromagnetic valve SV4 if the inside pressure of the air chamber AR returns to the atmospheric pressure.

Figure 90:
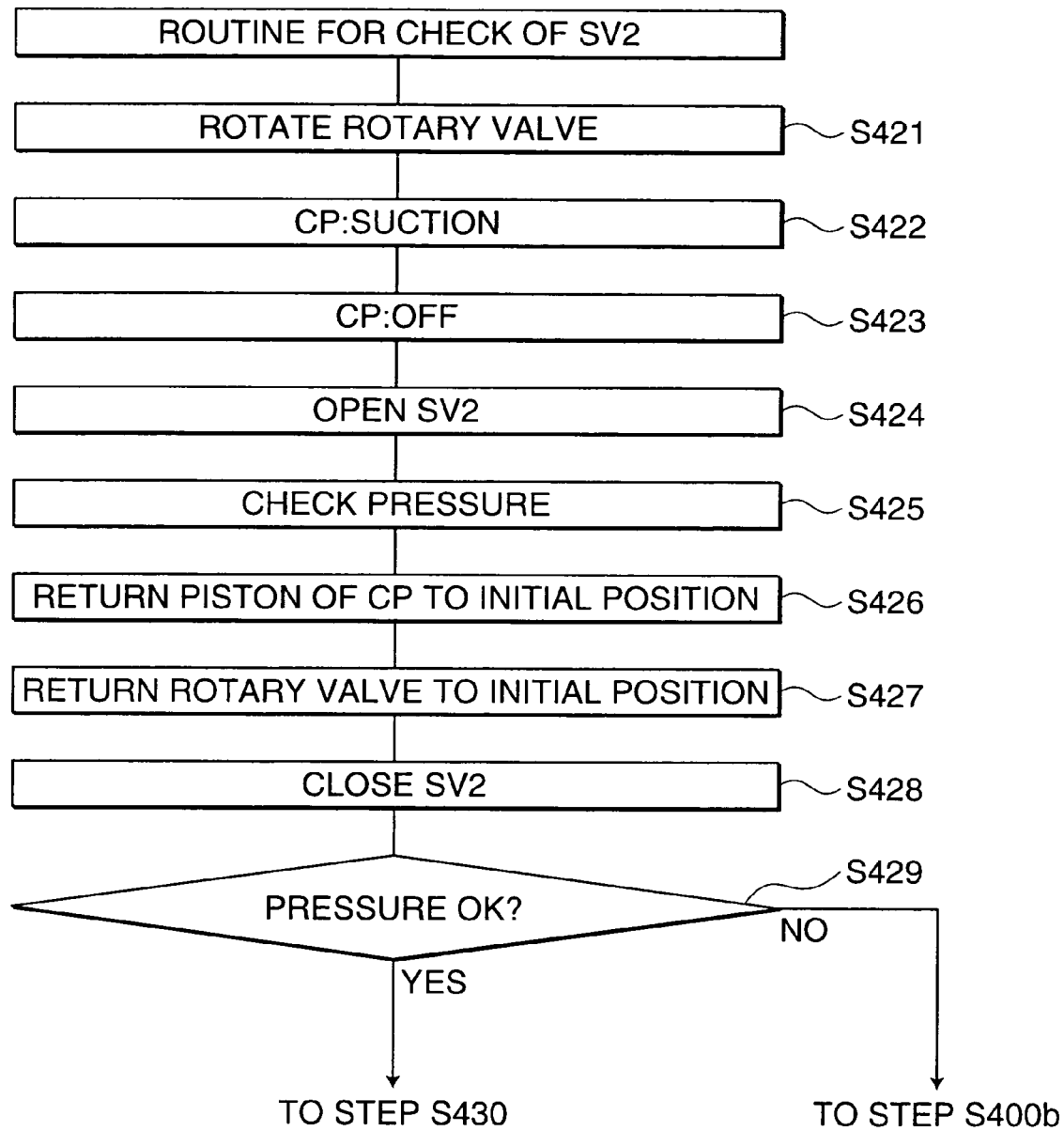

A detailed procedure (routine) for the check of the electromagnetic valve SV2 in Step S420 of FIG. 88 is shown in FIG. 90.

Figure 40:
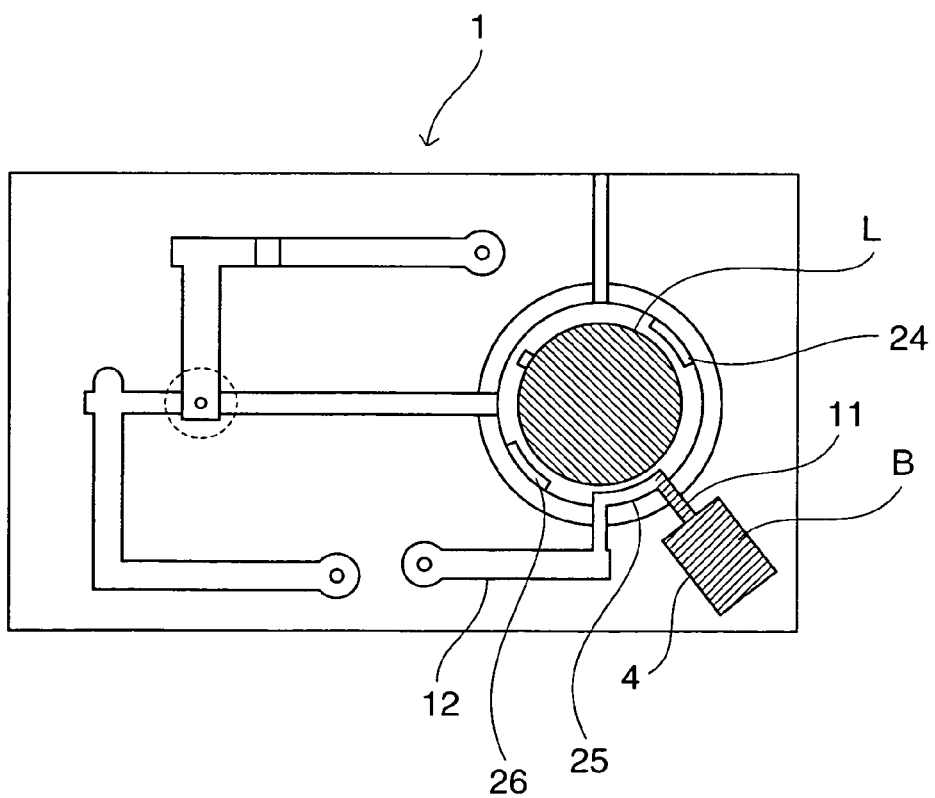

As shown in FIG. 90, the rotary valve 6 is first rotated to a position shown in FIG. 35 or FIG. 40 (Step S421).

Subsequently, the syringe pump CP is actuated to perform the sucking operation to keep the air chamber AR at a negative pressure (Steps S422, S423). Then, the electromagnetic valve SV2 is opened, and it is checked whether or not the inside pressure of the air chamber AR detected by the pressure sensor PS returns to the atmospheric pressure within a predetermined period (Steps S424, S425). In turn, the piston of the syringe pump CP and the rotary valve 6 are respectively returned to the initial positions, and the electromagnetic valve SV2 is closed (Steps S426 to S428). If the inside pressure of the air chamber AR returns to the atmospheric pressure in Step S425, the routine goes to Step S430 (FIG. 88). If the inside pressure of the air chamber AR does not return to the atmospheric pressure (Step S429), the routine goes to Step S400b (FIG. 87). This is because it is judged that the electromagnetic valve SV2 is not completely opened if the inside pressure of the air chamber AR does not return to the atmospheric pressure. On the other hand, it is judged that a predetermined amount of air is passed through the electromagnetic valve SV2 if the inside pressure of the air chamber AR returns to the atmospheric pressure.

Figure 91:
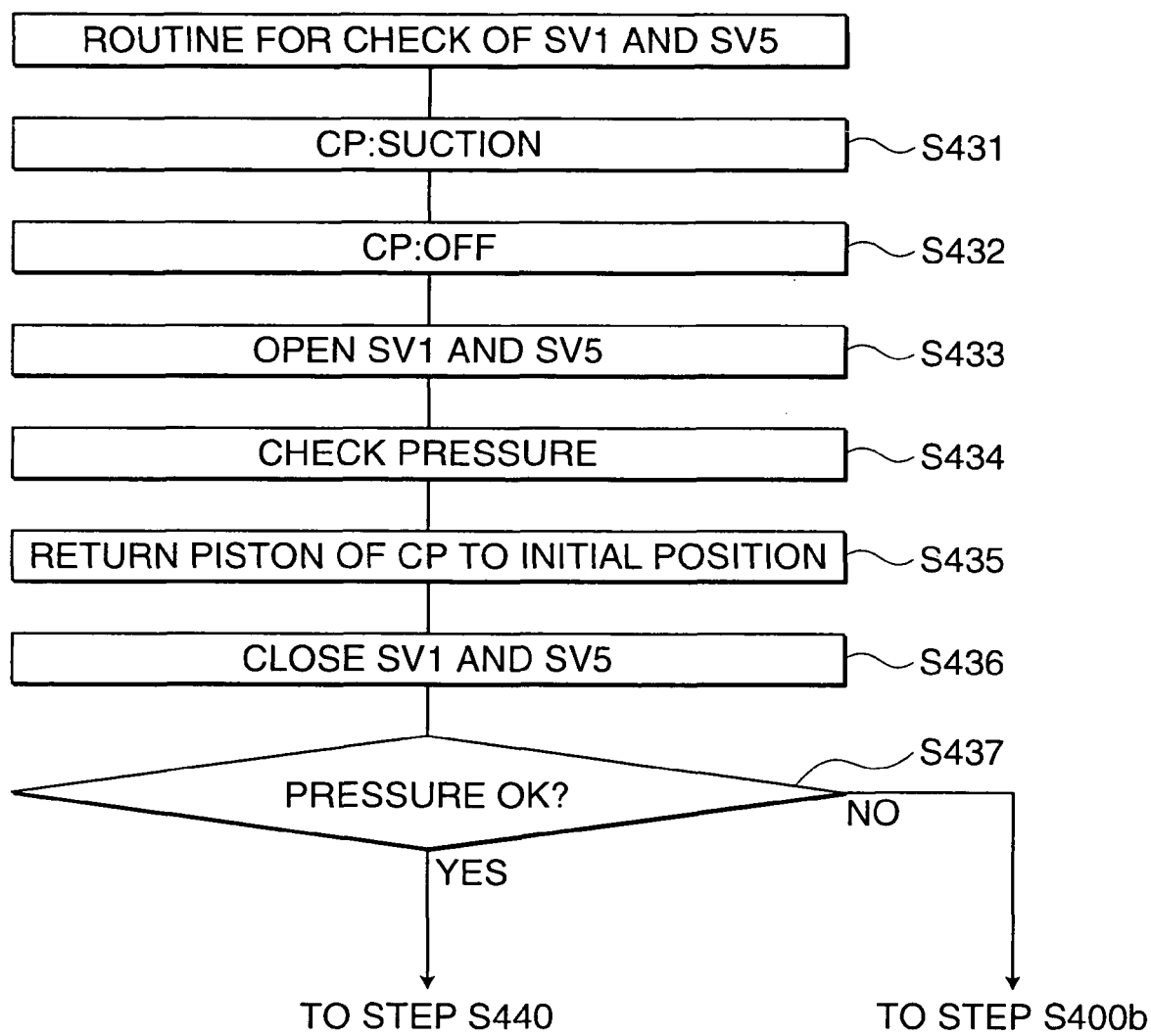

A detailed procedure (routine) for the check of the electromagnetic valves SV1, SV5 in Step S430 of FIG. 88 is shown in FIG. 91.

As shown in FIG. 91, the syringe pump CP is first actuated to perform the sucking operation to keep the air chamber AR at a negative pressure (Steps S431, S432). Then, the electromagnetic valves SV1, SV5 are opened, and it is checked whether or not the inside pressure of the air chamber AR detected by the pressure sensor PS returns to the atmospheric pressure within a predetermined period (Steps S433, S434). In turn, the piston of the syringe pump CP is returned to the initial position, and the electromagnetic valves SV1, SV5 are closed (Steps S435, S436). If the inside pressure of the air chamber AR returns to the atmospheric pressure in Step S434, the routine goes to Step S440 (FIG. 88). If the inside pressure of the air chamber AR does not return to the atmospheric pressure (Step S437), the routine goes to Step S400b (FIG. 87). This is because it is judged that the electromagnetic valve SV1 or SV5 is not completely opened if the inside pressure of the air chamber AR does not return to the atmospheric pressure. On the other hand, it is judged that a predetermined amount of air is passed through the electromagnetic valves SV1, SV5 if the inside pressure of the air chamber AR returns to the atmospheric pressure.

Figure 92:
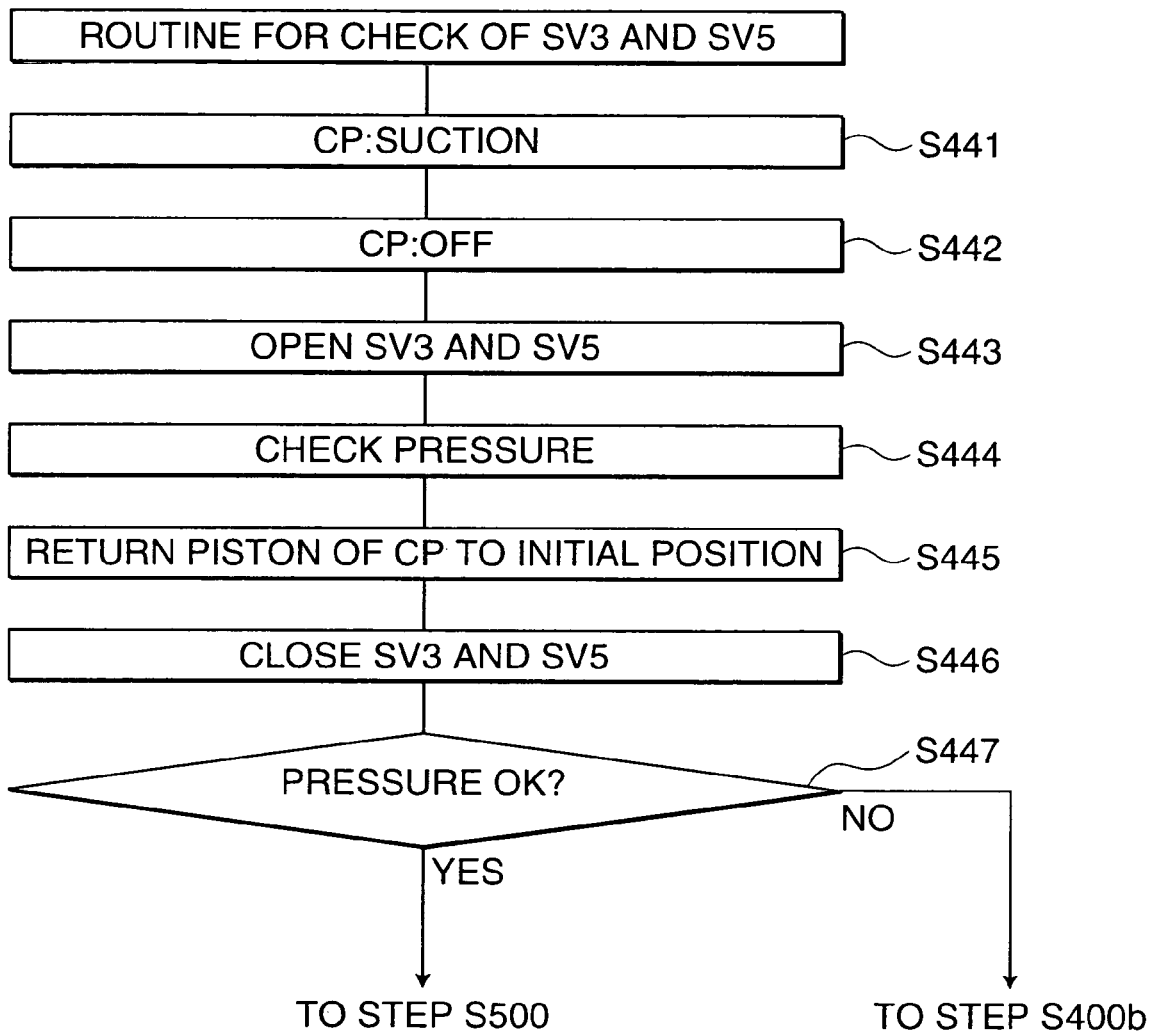

A detailed procedure (routine) for the check of the electromagnetic valves SV3, SV5 in Step S440 of FIG. 88 is shown in FIG. 92.

The syringe pump CP is first actuated to perform the sucking operation to keep the air chamber AR at a negative pressure (Steps S441, S442). Then, the electromagnetic valves SV3, SV5 are opened, and it is checked whether or not the inside pressure of the air chamber AR detected by the pressure sensor PS returns to the atmospheric pressure within a predetermined period (Steps S443, S444). In turn, the piston of the syringe pump CP is returned to the initial position, and the electromagnetic valves SV3, SV5 are closed (Steps S445, S446). If the inside pressure of the air chamber AR returns to the atmospheric pressure in Step S444, the routine goes to Step S500 (FIG. 87). If the inside pressure of the air chamber AR does not return to the atmospheric pressure (Step S447), the routine goes to Step S400b (FIG. 87). This is because it is judged that the electromagnetic valve SV3 or SV5 is not completely opened if the inside pressure of the air chamber AR does not return to the atmospheric pressure. On the other hand, it is judged that a predetermined amount of air is passed through the electromagnetic valves SV3, SV5 if the inside pressure of the air chamber AR returns to the atmospheric pressure.

Thus, the operation check of the electromagnetic valves is completed.

C-1-2. Check of Setting of Measuring Unit

Figure 93:
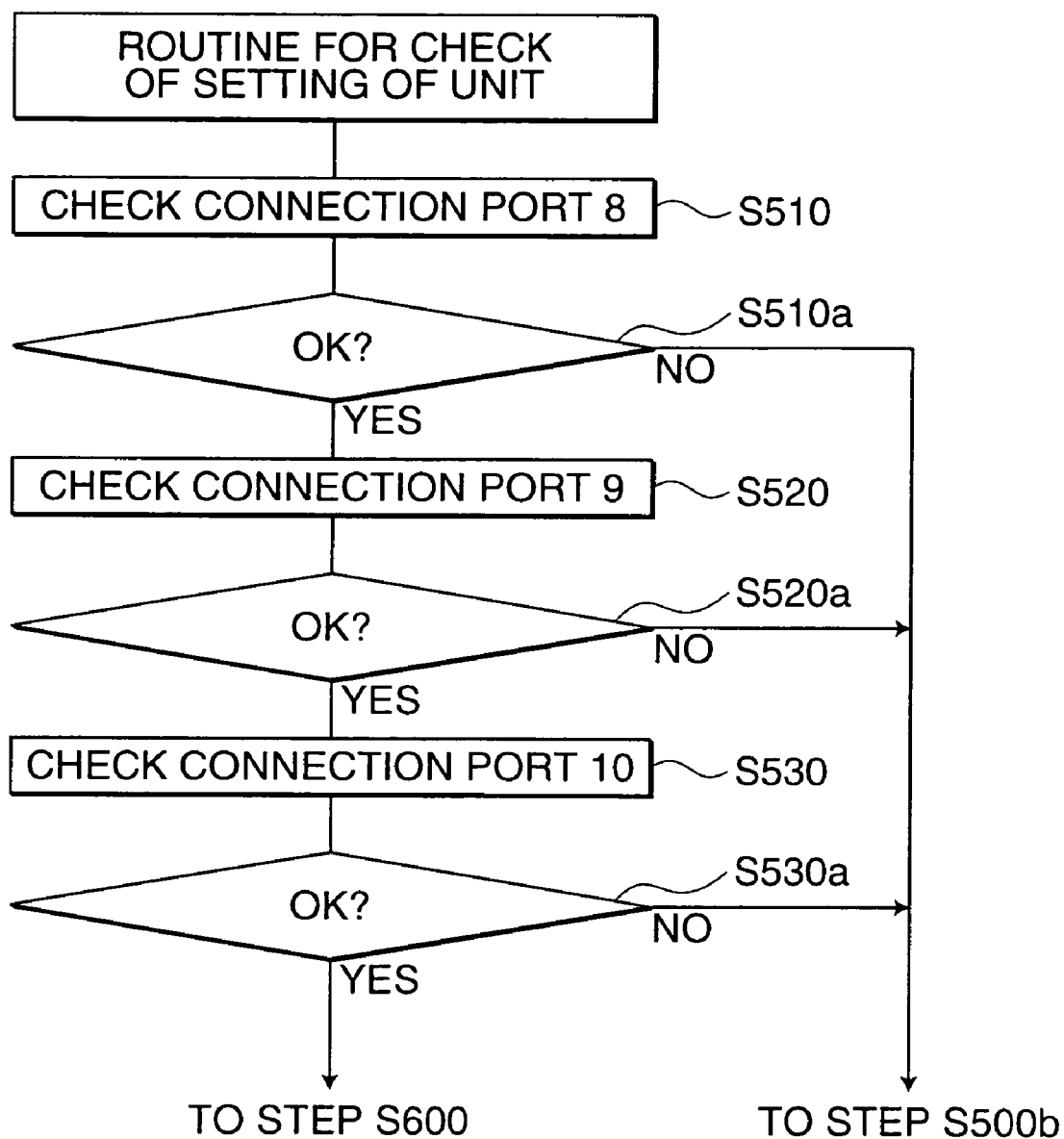

A detailed procedure (routine) for the check of the setting of the measuring unit in Step S500 of FIG. 87 is shown in FIG. 93.

As shown in FIG. 93, it is sequentially checked whether or not the connection port 8 is properly connected to the pipe connector 120, whether or not the connection port 9 is properly connected to the pipe connector 121, and whether or not the connection port 10 is properly connected to the pipe connector 122 (Steps S510, S520, S530). If the connection ports 8, 9 and 10 are normally connected to the pipe connectors 120, 121 and 122, respectively, the routine goes to Step S600 (FIG. 87). If the check result in Step S510a, S520a or S530a is negative, the routine goes to Step S500b (FIG. 87).

Figure 94:
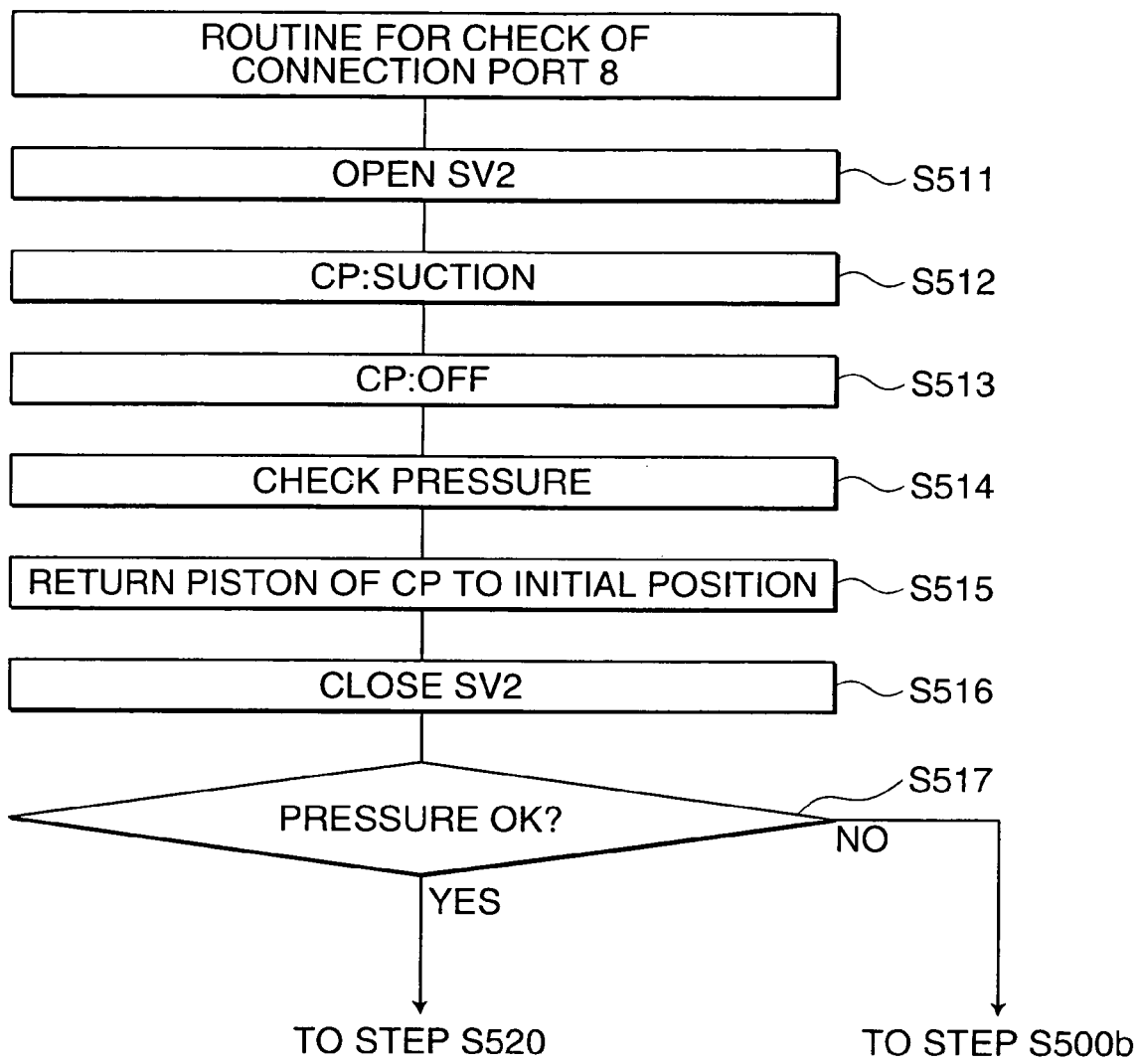

A detailed procedure (routine) for the check of the connection of the connection port 8 in Step S510 of FIG. 93 is shown in FIG. 94.

As shown in FIG. 94, the electromagnetic valve SV2 is first opened (Step S511), and the syringe pump CP is actuated to perform the sucking operation to evacuate the air chamber AR (Steps S512, S513). It is checked whether or not the inside pressure of the air chamber AR detected by the pressure sensor PS decreases to a predetermined level within a predetermined period (Step S514). Then, the piston of the syringe pump CP is returned to the initial position, and the electromagnetic valve SV2 is closed (Steps S515, S516). If the inside pressure of the air chamber AR decreases to the predetermined level in Step S514, the routine goes to Step S520 (FIG. 93). If the inside pressure of the air chamber AR does not decrease (Step S517), the routine goes to Step S500b (FIG. 87). This is because it is judged that the connection port 8 is not properly connected to the pipe connector 120 if the inside pressure of the air chamber AR does not decrease to the predetermined level. On the other hand, it is judged that no air is introduced into the channel connecting the air chamber AR and the connection port 8 from outside of the measuring unit 1 if the inside pressure of the air chamber AR decreases to the predetermined level.

Figure 95:
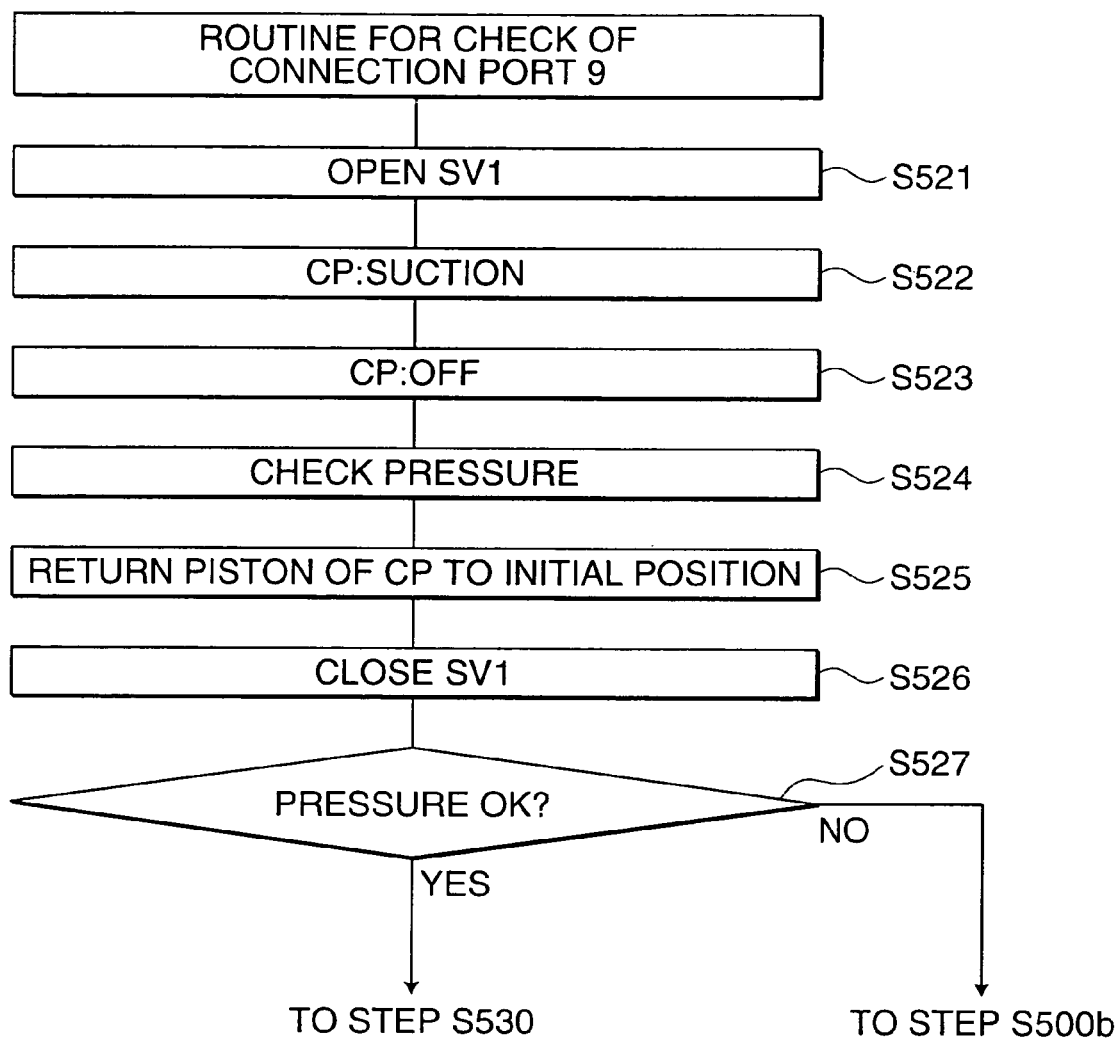

A detailed procedure (routine) for the check of the connection of the connection port 9 in Step S520 of FIG. 93 is shown in FIG. 95.

As shown in FIG. 95, the electromagnetic valve SV1 is first opened (Step S521), and the syringe pump CP is actuated to perform the sucking operation to evacuate the air chamber AR (Steps S522, S523). It is checked whether or not the inside pressure of the air chamber AR detected by the pressure sensor PS decreases to a predetermined level within a predetermined period (Step S524). Then, the piston of the syringe pump CP is returned to the initial position, and the electromagnetic valve SV1 is closed (Steps S525, S526). If the inside pressure of the air chamber AR decreases to the predetermined level in Step S524, the routine goes to Step S530 (FIG. 93). If the inside pressure of the air chamber AR does not decrease (Step S527), the routine goes to Step S500b (FIG. 87). This is because it is judged that the connection port 9 is not properly connected to the pipe connector 121 if the inside pressure of the air chamber AR does not decrease to the predetermined level. On the other hand, it is judged that no air is introduced into the channel connecting the air chamber AR and the connection port 9 from outside of the measuring unit 1 if the inside pressure of the air chamber AR decreases to the predetermined level.

Figure 96:
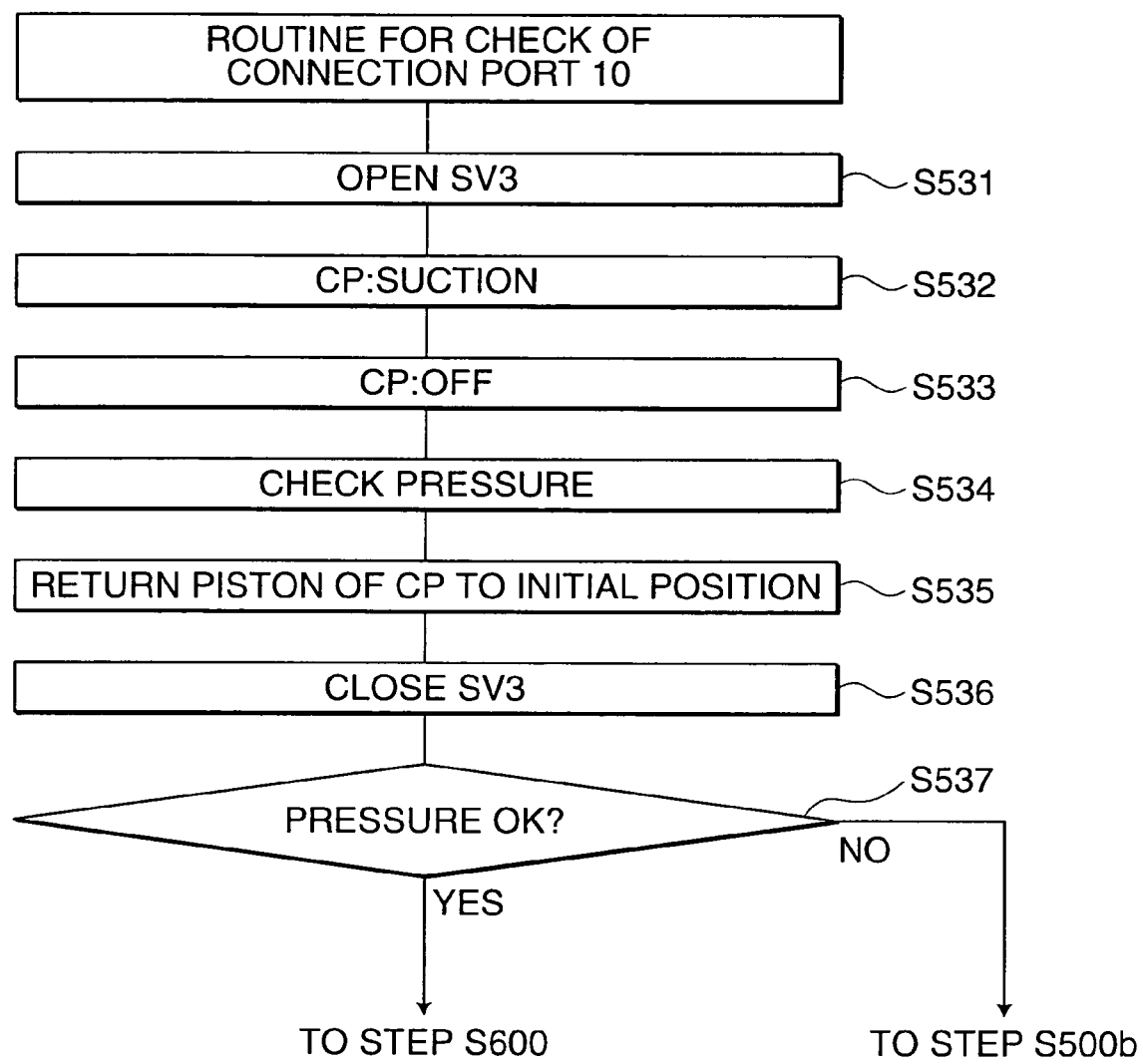

A detailed procedure (routine) for the check of the connection of the connection port 10 in Step S530 of FIG. 93 is shown in FIG. 96.

As shown in FIG. 96, the electromagnetic valve SV3 is first opened (Step S531), and the syringe pump CP is actuated to perform the sucking operation to evacuate the air chamber AR (Steps S532, S533). It is checked whether or not the inside pressure of the air chamber AR detected by the pressure sensor PS decreases to a predetermined level within a predetermined period (Step S534). Then, the piston of the syringe pump CP is returned to the initial position, and the electromagnetic valve SV3 is closed (Steps S535, S536). If the inside pressure of the air chamber AR decreases to the predetermined level in Step S534, the routine goes to Step S600 (FIG. 87). If the inside pressure of the air chamber AR does not decrease (Step S537), the routine goes to Step S500b (FIG. 87). This is because it is judged that the connection port 10 is not properly connected to the pipe connector 122 if the inside pressure of the air chamber AR does not decrease to the predetermined level. On the other hand, it is judged that no air is introduced into the channel connecting the air chamber AR and the connection port 10 from outside of the measuring unit 1 if the inside pressure of the air chamber AR decreases to the predetermined level.

Thus, the check of the setting of the measuring unit is completed.

C-1-3. Check of Measuring Unit

Figure 97:
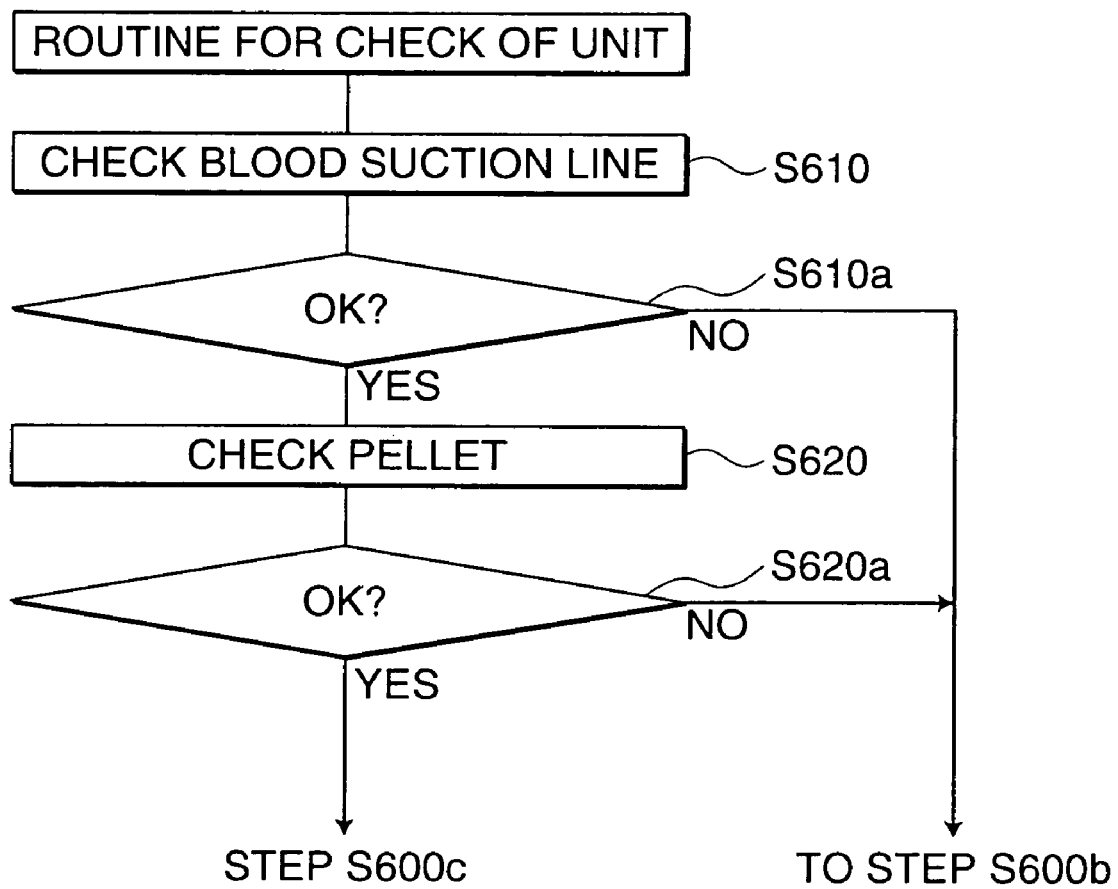

A detailed procedure (routine) for the check of the measuring unit in Step S600 of FIG. 87 is shown in FIG. 97.

As shown in FIG. 97, it is sequentially checked whether or not a blood suction line in the measuring unit set in the measuring section 110 is normal and whether or not the pellet 33 incorporated in the measuring unit is normal (Steps S610, S620). If the blood suction line and the pellet 33 are both normal, the routine goes to Step S600c (FIG. 87). If the check result in Step S610a or S620a is negative, the routine goes to step S600b (FIG. 87).

Figure 98:
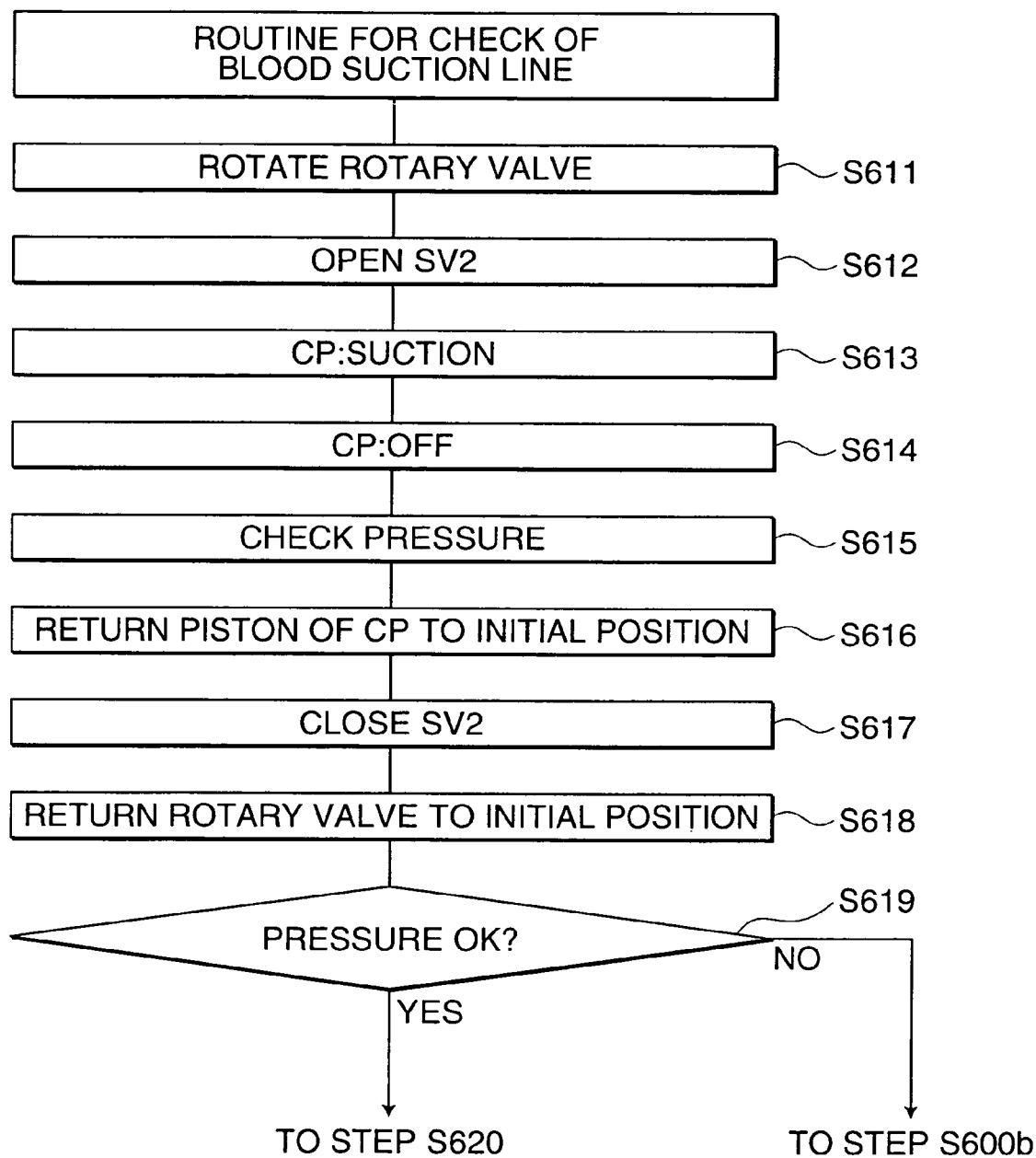

A detailed procedure (routine) for the check of the blood suction line in Step S610 of FIG. 97 is shown in FIG. 98.

As shown in FIG. 98, the rotary valve 6 is first rotated to a position shown in FIG. 35 or FIG. 40 (Step S611).

Subsequently, the valve SV2 is opened (Step S612), and the syringe pump CP is actuated to perform the sucking operation (Steps S613, S614). It is checked whether or not the inside pressure of the air chamber AR detected by the pressure sensor PS decreases to a predetermined level within a predetermined period (Step S615). In turn, the piston of the syringe pump CP and the rotary valve 6 are respectively returned to the initial positions, and the electromagnetic valve SV2 is closed (Steps S616 to S618). If the inside pressure of the air chamber AR does not decrease to the predetermined level in Step S615, the routine goes to Step S620 (FIG. 97). If the inside pressure of the air chamber AR decreases to the predetermined level (Step S619), the routine goes to Step S600b (FIG. 87). This is because it is judged that the blood suction line is clogged if the inside pressure of the air chamber AR decreases to the predetermined level. On the other hand, it is judged that a predetermined amount of air is not passed through the blood suction line if the inside pressure of the air chamber AR does not decrease to the predetermined level.

Figure 99:
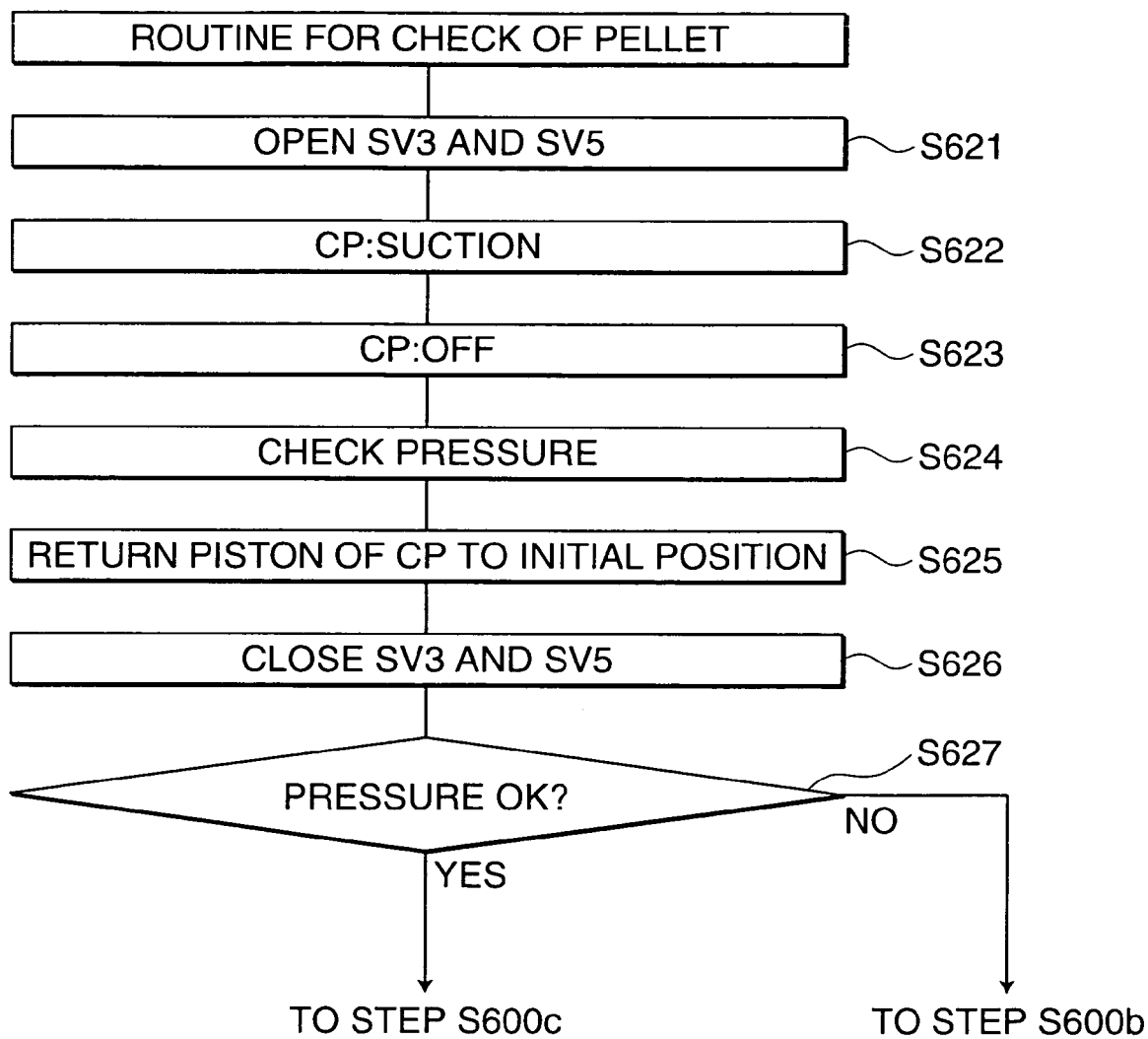

A detailed procedure (routine) for the check of the pellet in Step S620 of FIG. 97 is shown in FIG. 99.

As shown in FIG. 99, the electromagnetic valves SV3, SV5 are opened (Step S621), and the syringe pump CP is actuated to perform the sucking operation (Steps S622, S623). It is checked whether or not the inside pressure of the air chamber AR detected by the pressure sensor PS decreases to a predetermined level within a predetermined period (Step S624). In turn, the piston of the syringe pump CP is returned to the initial position, and the electromagnetic valves SV3, SV5 are closed (Steps S625, S626). If the inside pressure of the air chamber AR does not decrease to the predetermined level in Step S624, the routine goes to Step S600c (FIG. 87). If the inside pressure of the air chamber AR decreases to the predetermined level (Step S627), the routine goes to Step S600b (FIG. 87). This is because it is judged that the through-hole of the pellet 33 or a peripheral line is clogged if the inside pressure of the air chamber AR decreases to the predetermined level. On the other hand, it is judged that a predetermined amount of air is passed through the pellet 33 and the peripheral line if the inside pressure of the air chamber AR does not decrease to the predetermined level.

Thus, the check of the measuring unit is completed, and the pressure test (Step S104 of FIG. 24) is completed.

C-2. Measuring Operation with First Measuring Unit

Figure 25:
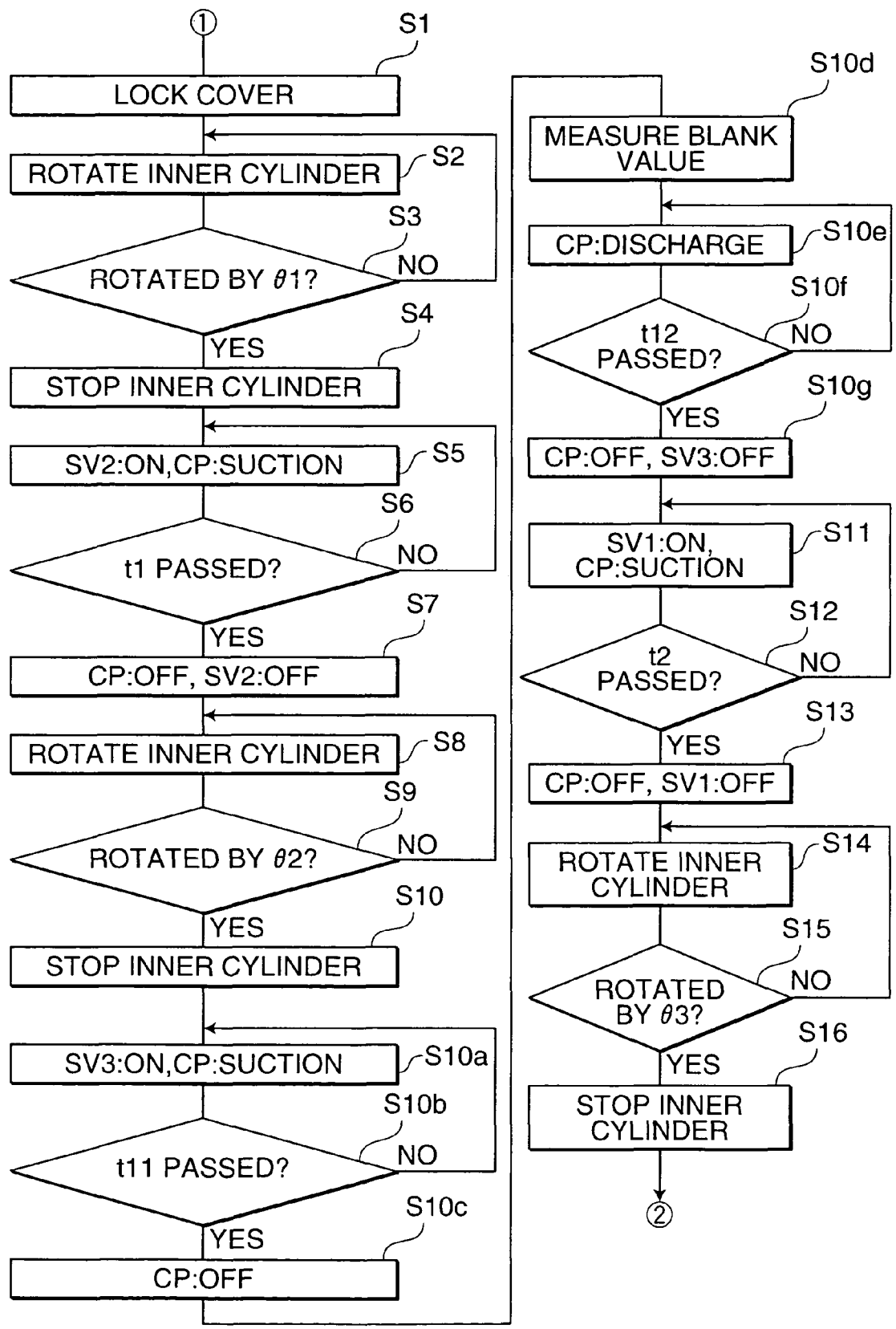
FIGS. 25 to 27 are flow charts for explaining an operation to be performed by the analyzer of FIG. 18 when the first measuring unit is set in the analyzer.
Figure 26:
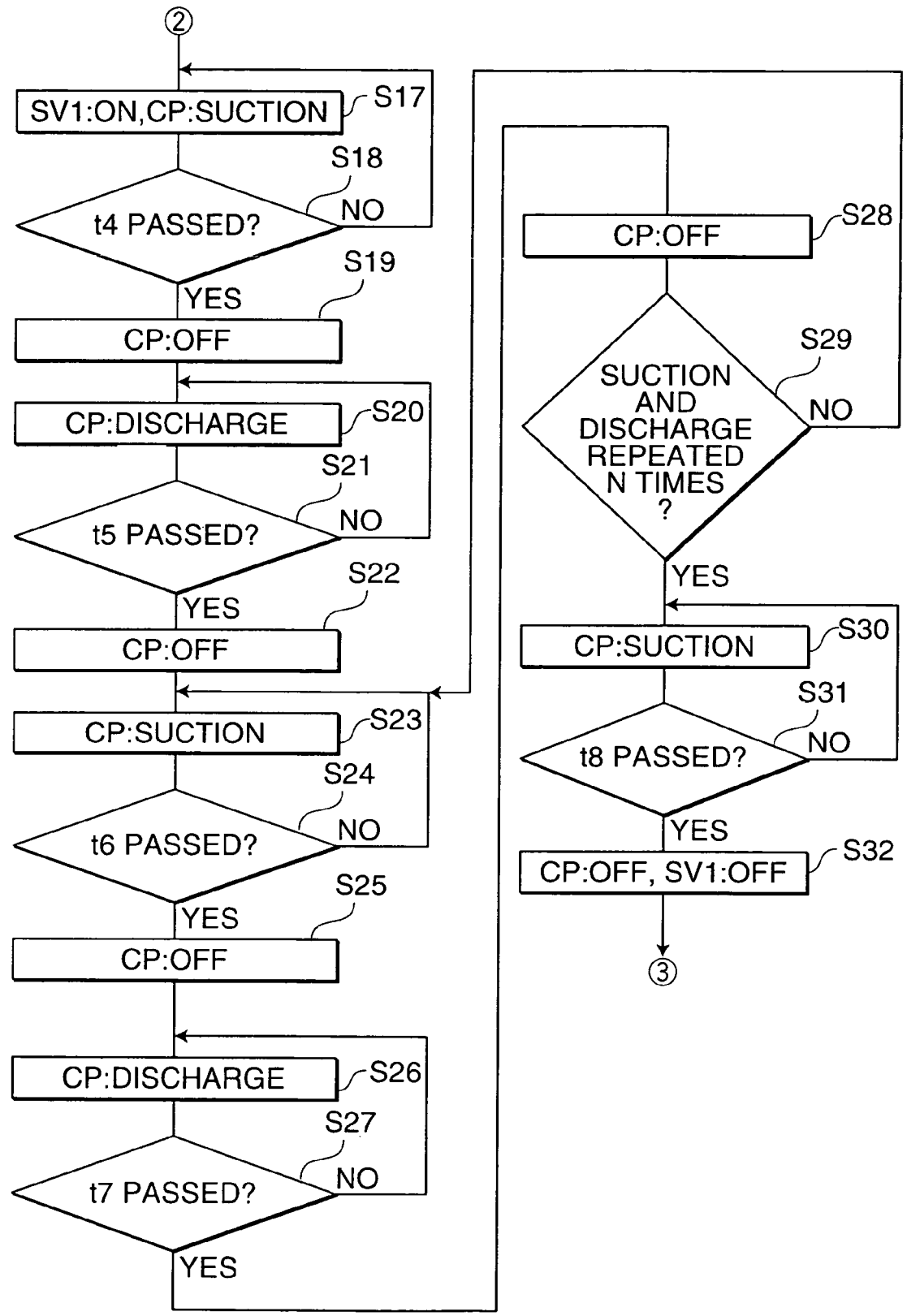
Figure 27:
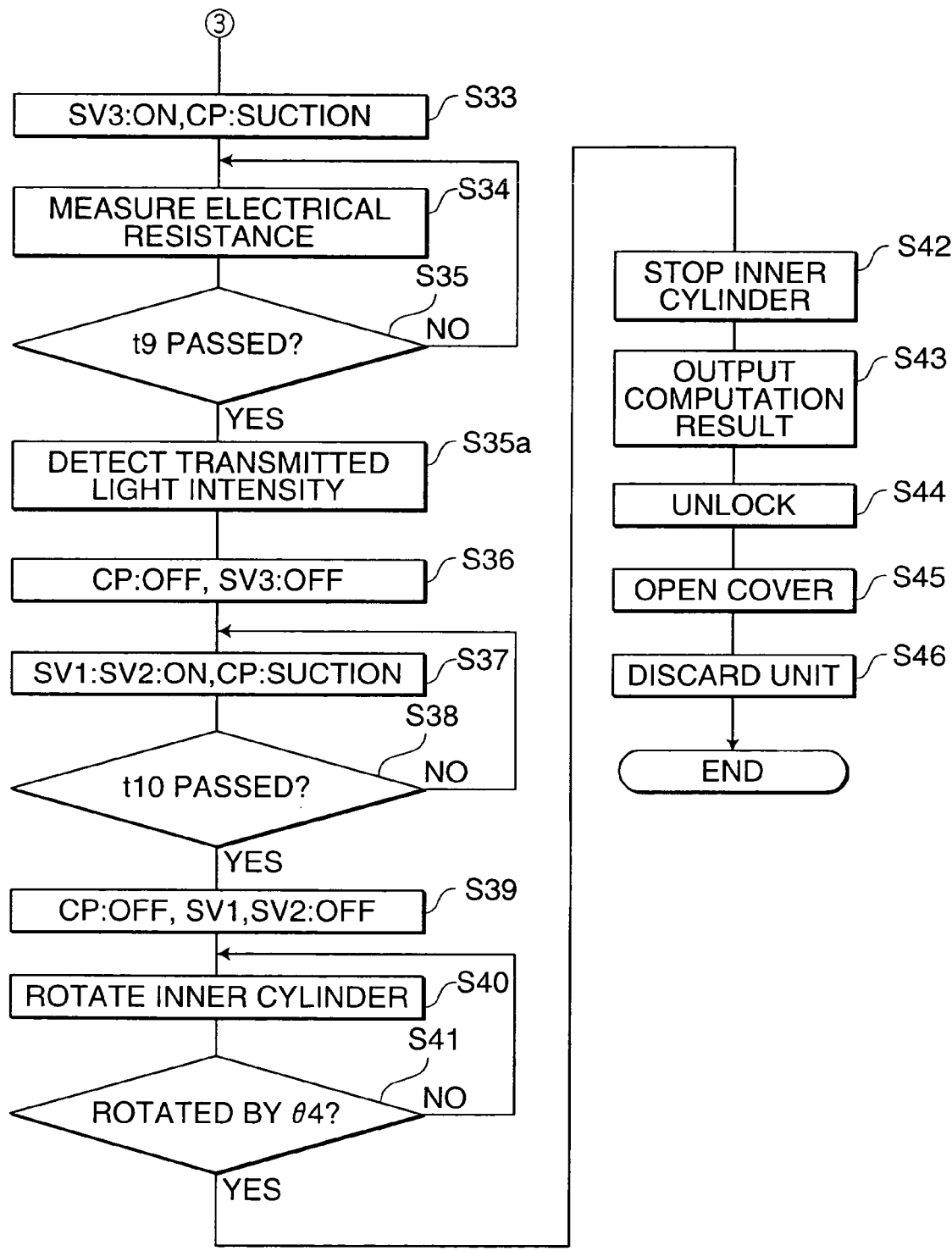

If it is judged in Step S112 of FIG. 24 that the measuring unit set in the measuring section 110 is the first unit 1, the routine goes to Step S1 of FIG. 25. The solenoid RS is first actuated to lock the cover 111 (Step S1). The electromagnetic valve SV4 is actuated as required to open the air chamber AR to the atmosphere. However, no explanation will be given to the operation of the electromagnetic valve SV4 in the following measuring operation.

Then, the stepping motor M1 is driven to rotate the inner cylinder 17 clockwise by an angle θ1 from the initial position shown in FIGS. 34(a) to 34(c) and 39 to a position as shown in FIGS. 35(a) to 35(c) and 40 (Steps S2 to S4).

Figure 35A:
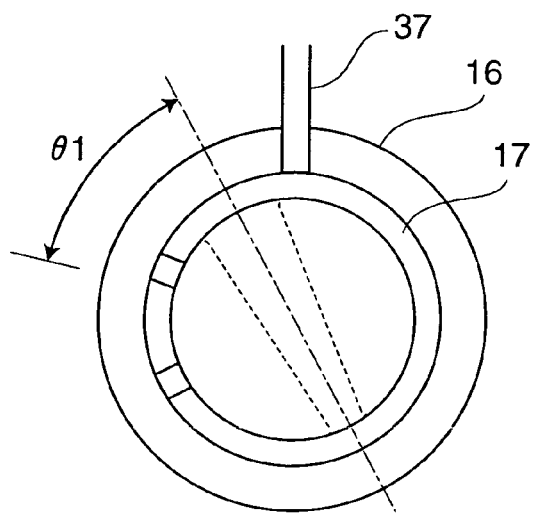
Figure 35B:
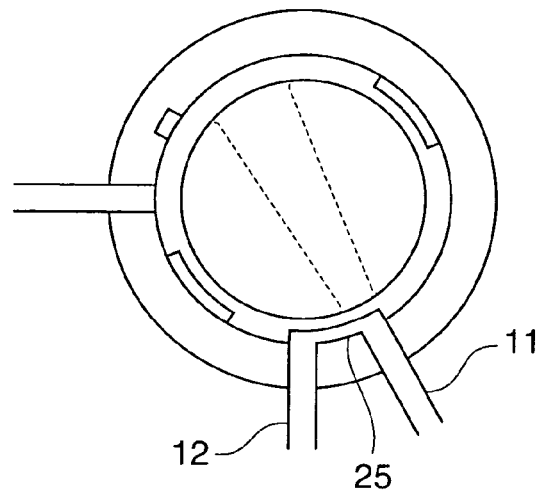
Figure 35C:
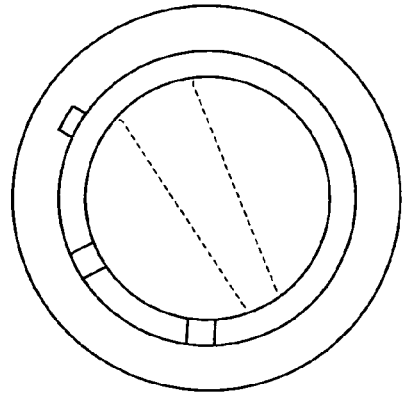
Figure 41:
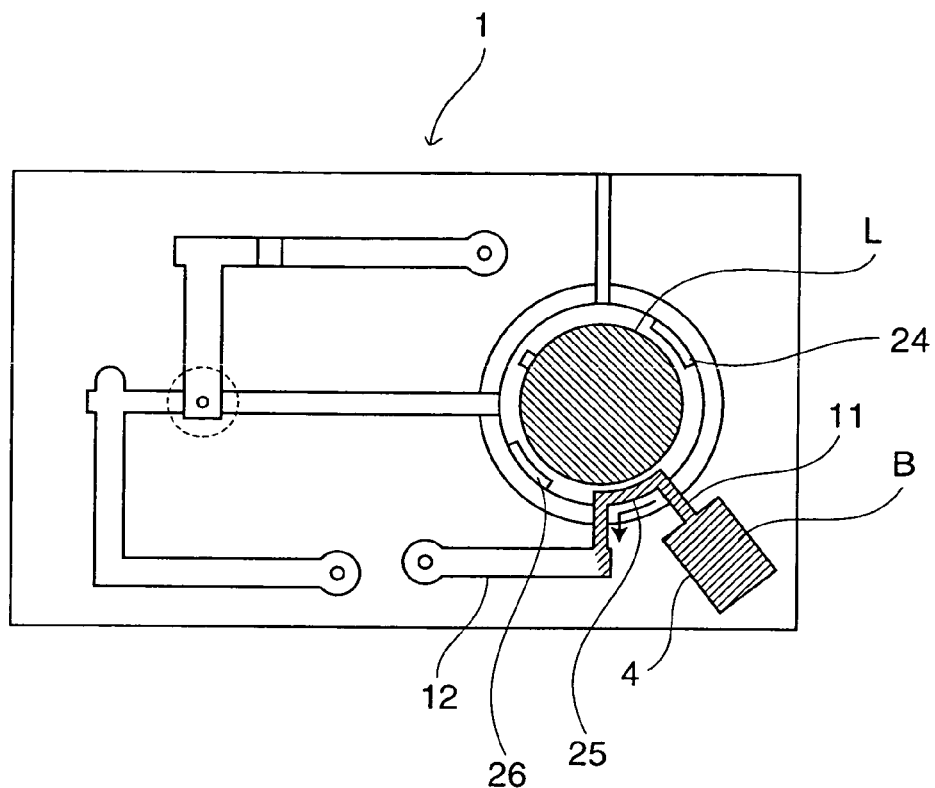

Thus, the channels 11, 12 communicate with each other via the lateral groove 25 to form the metering channel as shown in FIGS. 35(b) and 40. In this state, the syringe pump CP performs the sucking operation for a time period t1 with the valve SV2 being open, and then the valve SV2 is closed (Steps S5 to S7), whereby a whole blood sample B flows into the channel 12 from the sample receiving section 4 via the lateral groove 25 to fill the lateral groove 25 as shown in FIG. 41.

Figure 42:
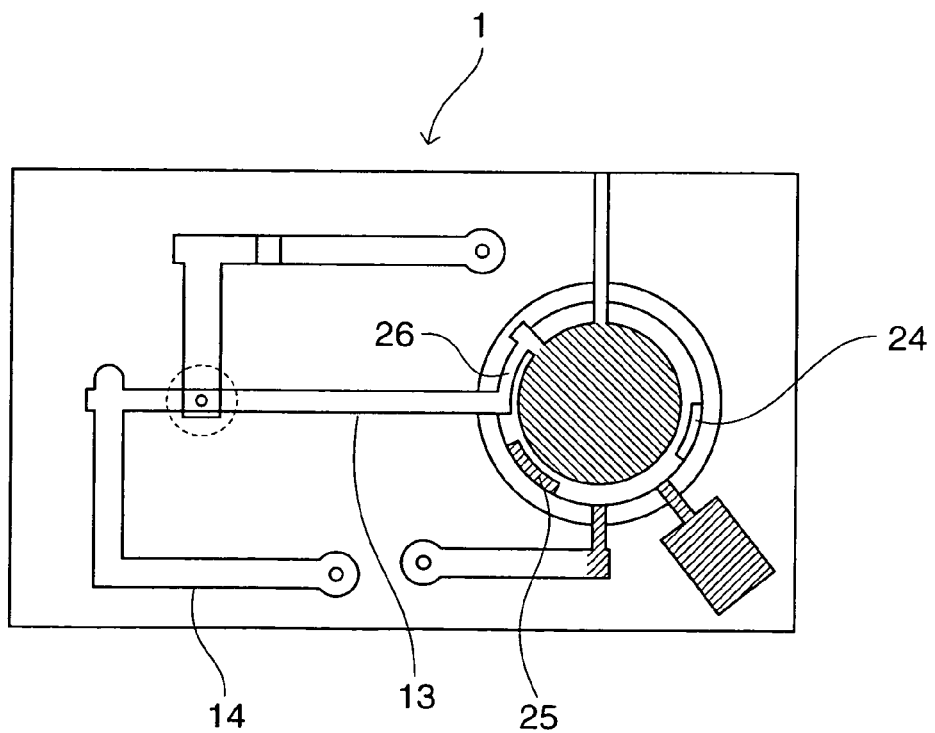

In turn, the stepping motor M1 is driven to rotate the inner cylinder 17 clockwise by an angle θ2 to a position as shown in FIGS. 36(a) to 36(c) and 42 (Steps S8 to S10). Thus, the sample is metered in a volume of 2 μL which is equivalent to the volume of the lateral groove 25, and separated by the inner circumferential surface of the outer cylinder 16 as shown in FIG. 42.

Figure 36A:
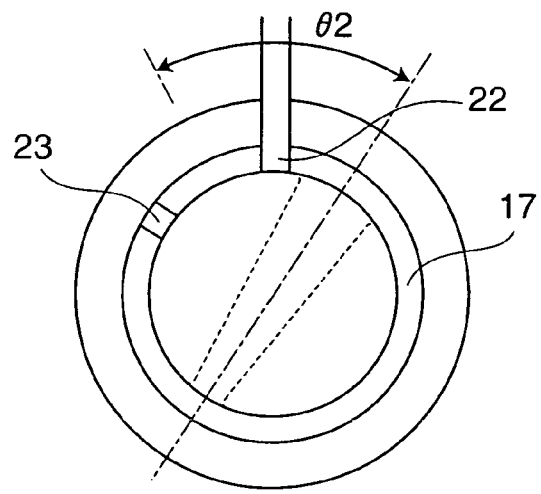
Figure 36B:
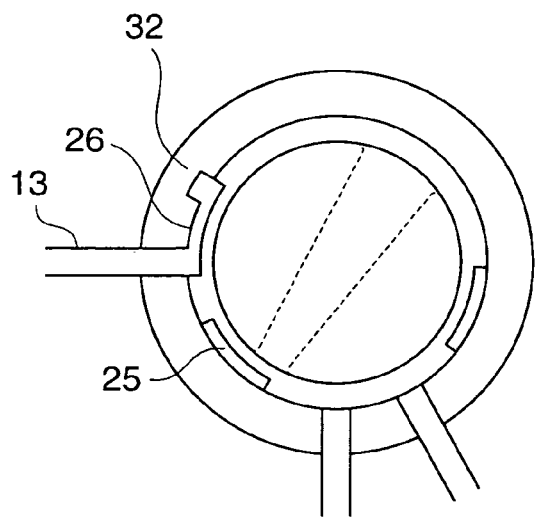
Figure 36C:
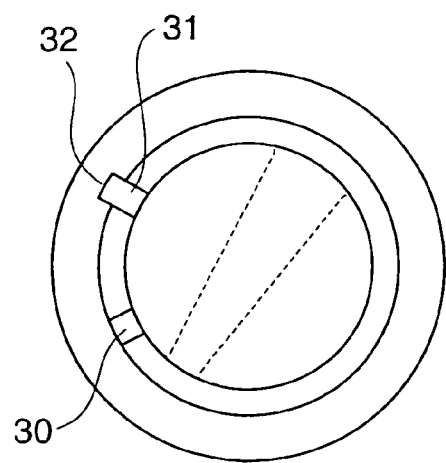

At the same time, the through-hole 22 of the inner cylinder 17 communicates with the vent hole 37 to open an upper portion of the diluent container 5 to the atmosphere as shown in FIG. 36(a), and the channel 13 communicates with the bottom of the diluent container 5 via the lateral groove 26, the vertical groove 32 and the through-hole 31 as shown in FIGS. 36(b) and 36(c).

Figure 43:
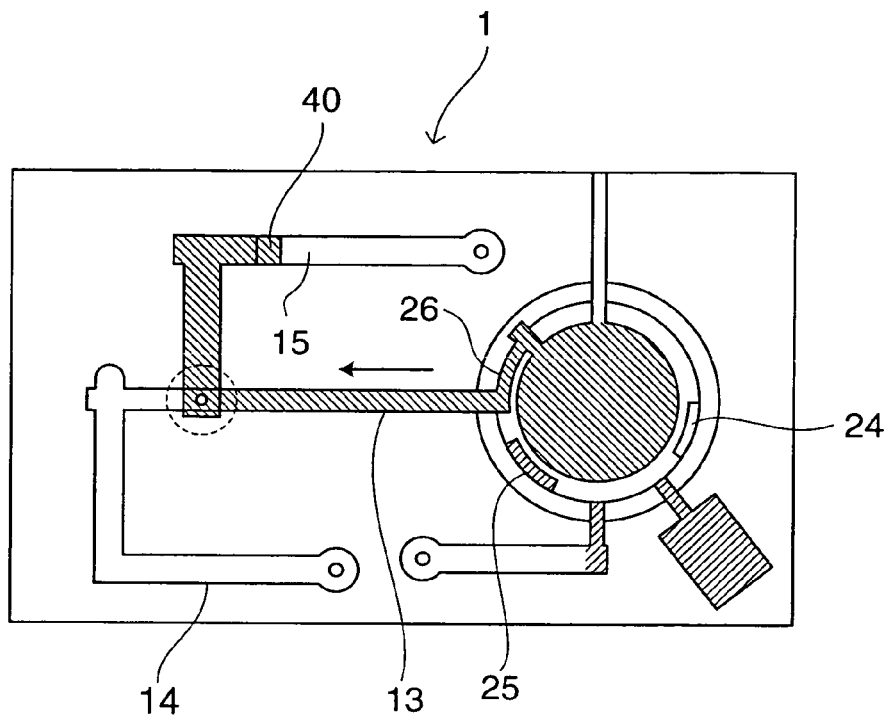
Figure 44:
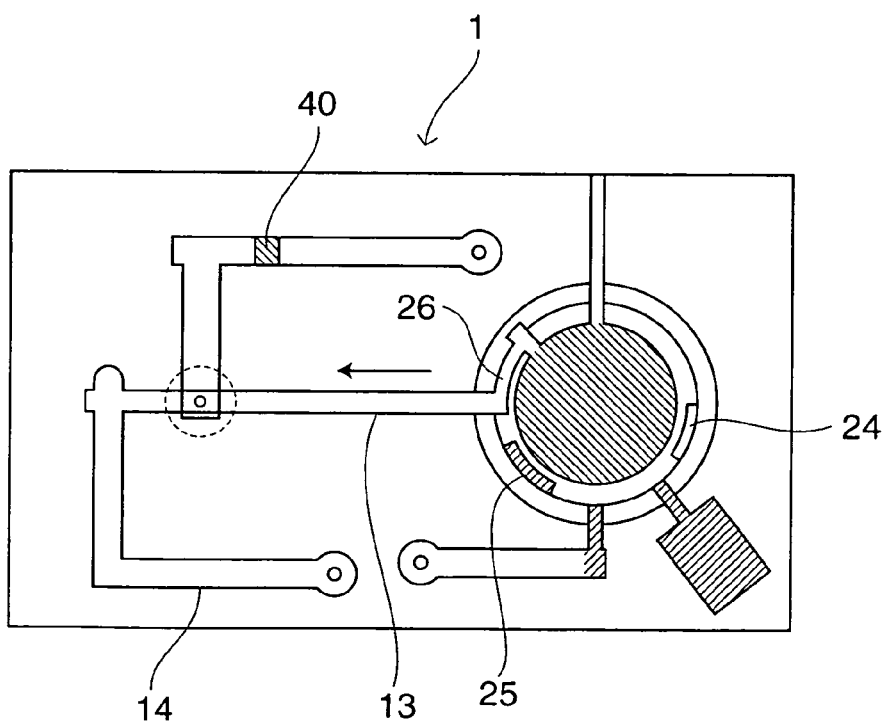

Then, the valve SV3 is opened, and the syringe pump CP performs the sucking operation for a time period t11 (Steps S10a to S10c), whereby the diluent L is introduced into the channel 15 from the diluent container 5 through the channel 13 as shown in FIG. 43. Thus, 50 μL of the diluent L is retained in the absorbance measuring chamber 40. Then, the laser diode 125 emits light toward the absorbance measuring chamber 40, and the photodiode 126 detects the intensity of light transmitted through the absorbance measuring chamber 40. A detection value (blank value) is stored in the control section 106 (Step S10d). Then, the syringe pump CP performs a discharging operation for a time period t12, and the valve SV3 is closed (Steps S10e to S10g). Thus, the diluent L in the channels 15, 13 is fed back into the diluent container 5 as shown in FIG. 44.

Figure 45:
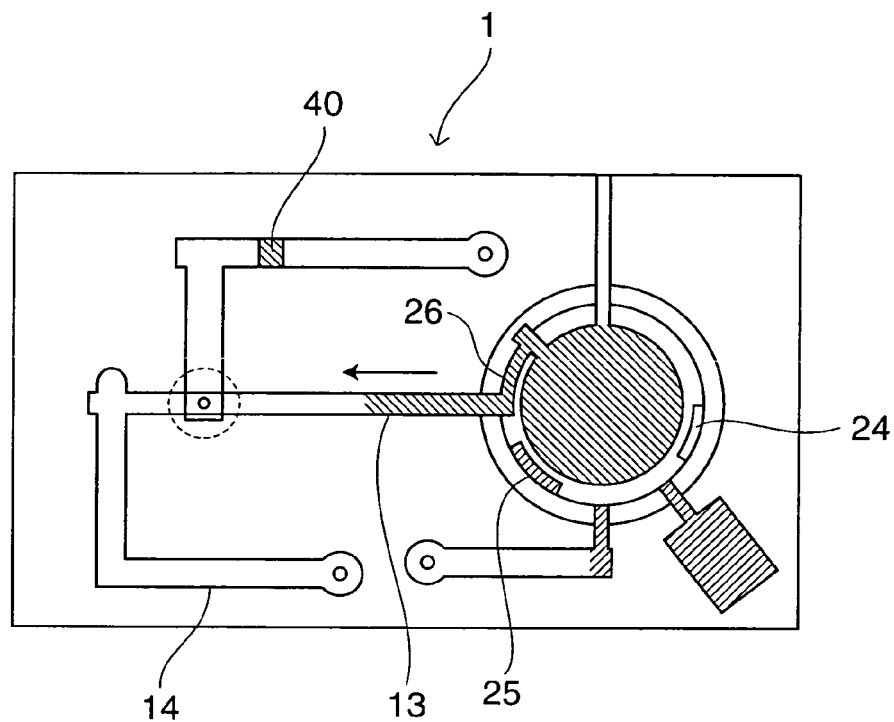

In turn, the syringe pump CP performs the sucking operation for a time period t2 with the valve SV1 being open, and then the valve SV1 is closed (Steps S11 to S13), whereby the diluent L is sucked into the channel 13 from the diluent container 5 as shown in FIG. 45.

Figure 37A:
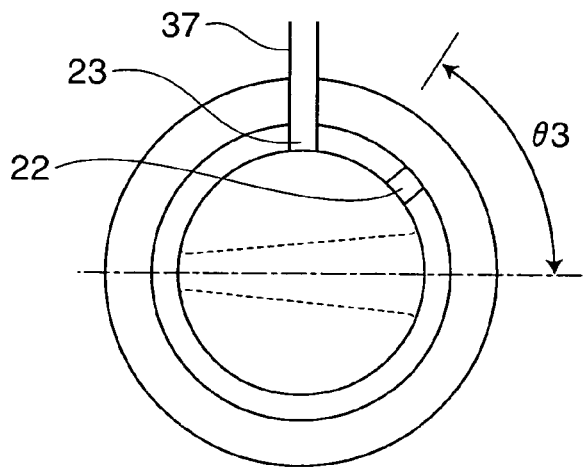
Figure 37B:
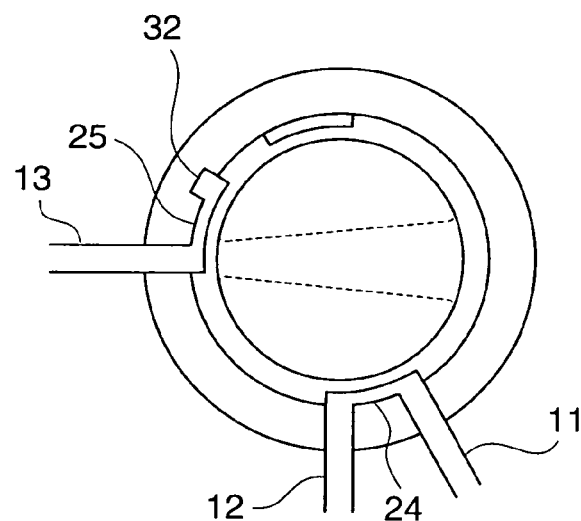
Figure 37C:
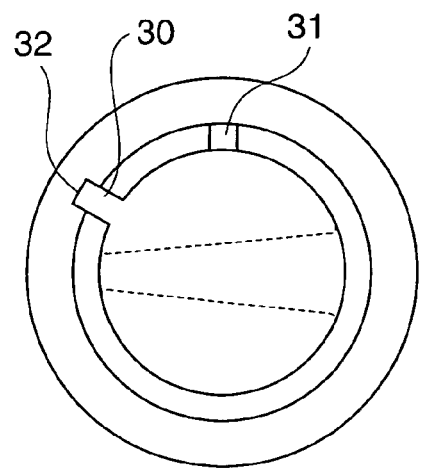

Subsequently, the stepping motor M1 is driven to rotate the inner cylinder 17 clockwise by an angle θ3 to a position as shown in FIGS. 37(a) to 37(c) (Steps S14 to S16).

Figure 46:
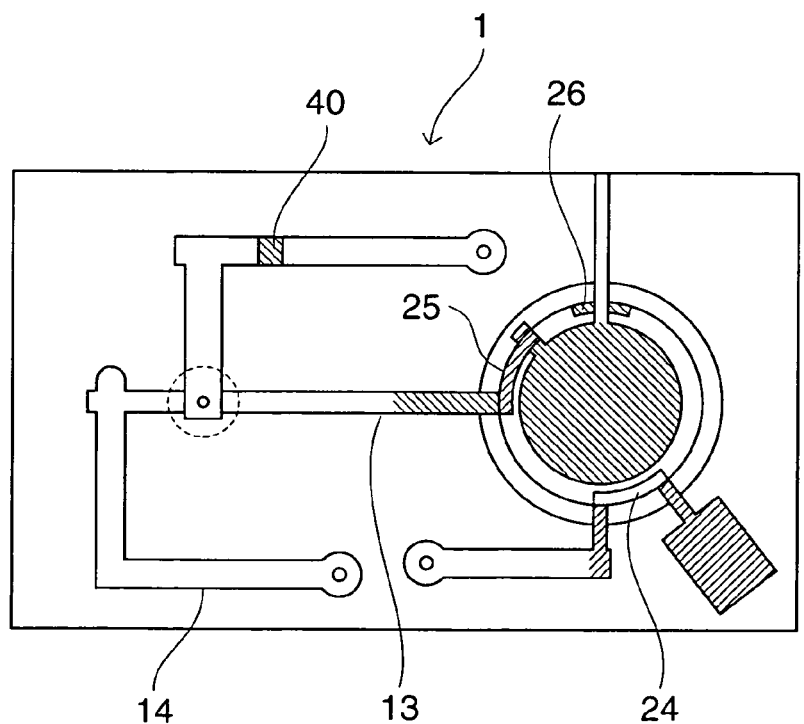

Thus, the through-hole 23 of the inner cylinder 17 communicates with the vent hole 37 to open the upper portion of the diluent container 5 to the atmosphere as shown in FIG. 37(a), and the channel 13 communicates with the bottom of the diluent container 5 via the lateral groove 25, the vertical groove 32 and the through-hole 30 to form the agitation channel as shown in FIGS. 37(b), 37(c) and 46. At the same time, the channel 11 communicates with the channel 12 via the lateral groove 24 as shown in FIG. 37(b).

Figure 47:
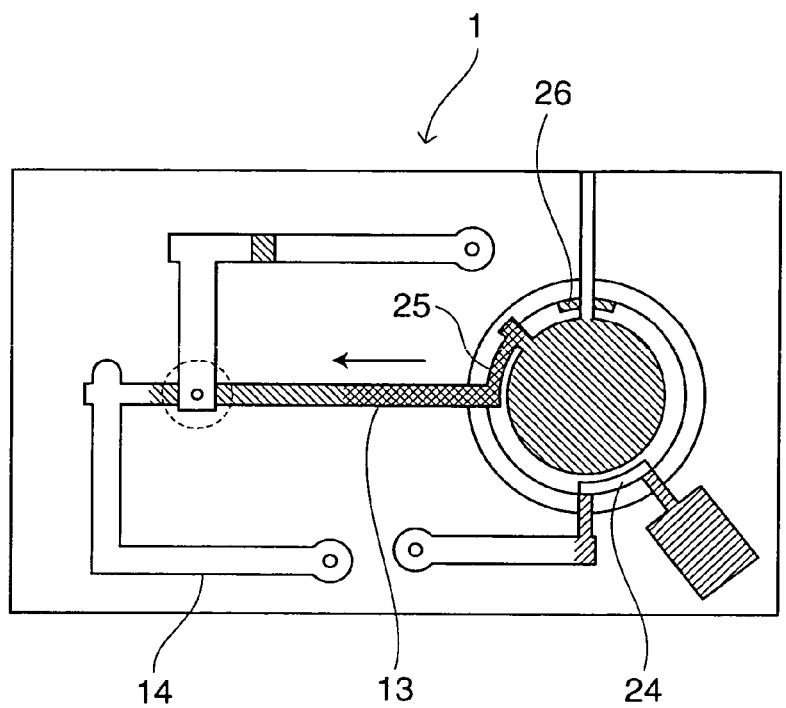

Then, the valve SV1 is opened, and the syringe pump CP further performs the sucking operation for a time period t4 (Steps S17 to S19), whereby the diluent L is sucked into the channel 13 from the diluent container 5 together with the metered sample in the lateral groove 25 as shown in FIG. 47.

Figure 48:
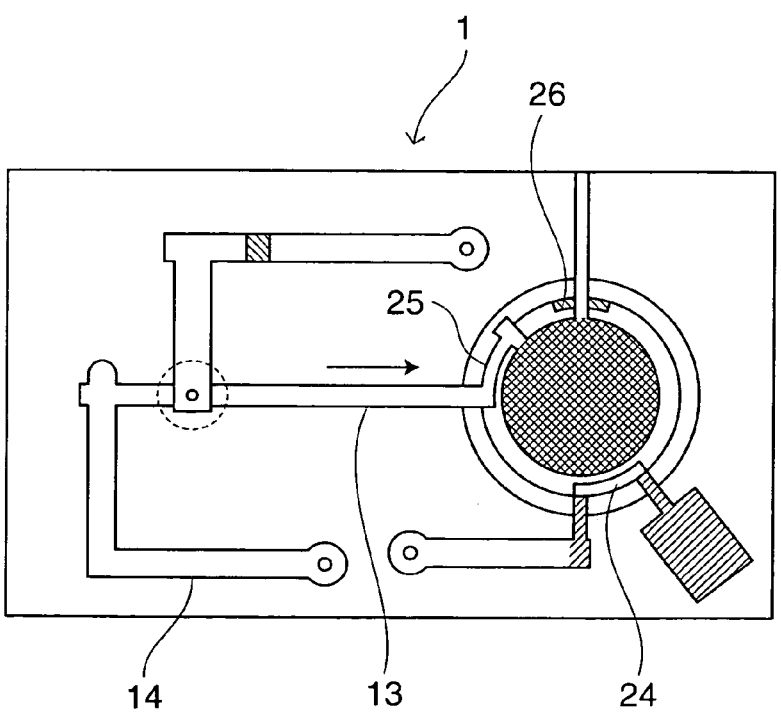

In turn, the syringe pump CP performs the discharging operation for a time period t5 (Steps S20 to S22), whereby the sample and the diluent are fed back into the diluent container 5 as shown in FIG. 48.

Figure 49:
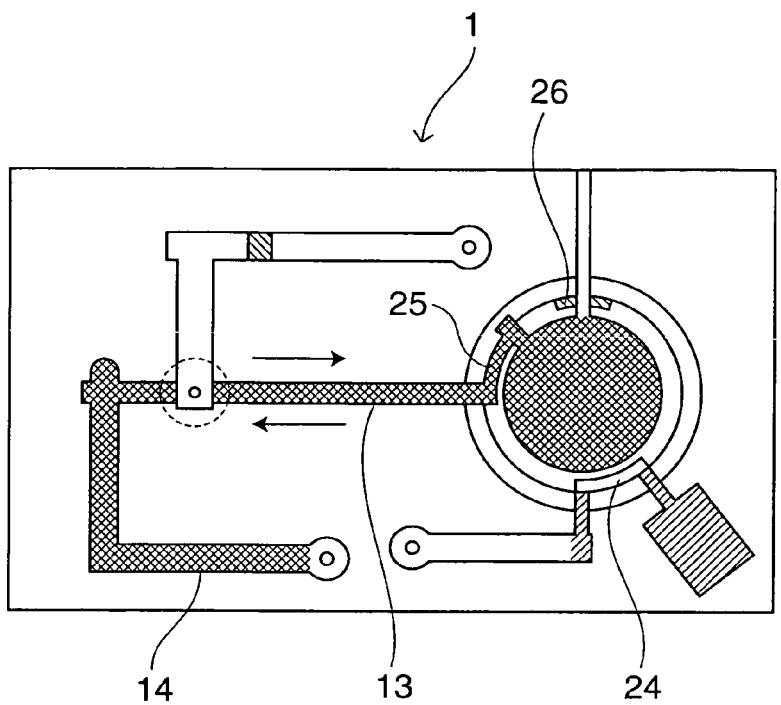
Figure 50:
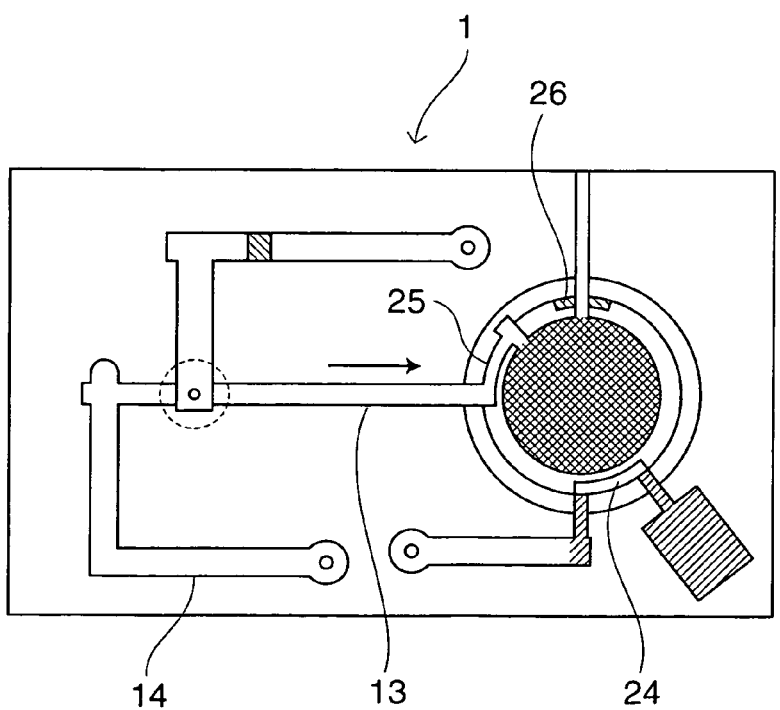

Subsequently, the syringe pump CP repeats a t6-period sucking operation and a t7-period discharging operation N times (Steps S23 to S29), whereby the diluent and the sample flow back and forth between the channels 13, 14 and the diluent container 5 as shown in FIG. 49. Thus, the diluent and the sample are sufficiently mixed and agitated for preparation of a 500-time diluted sample. The diluted sample is retained in the diluent container 5 as shown in FIG. 50.

Figure 51:
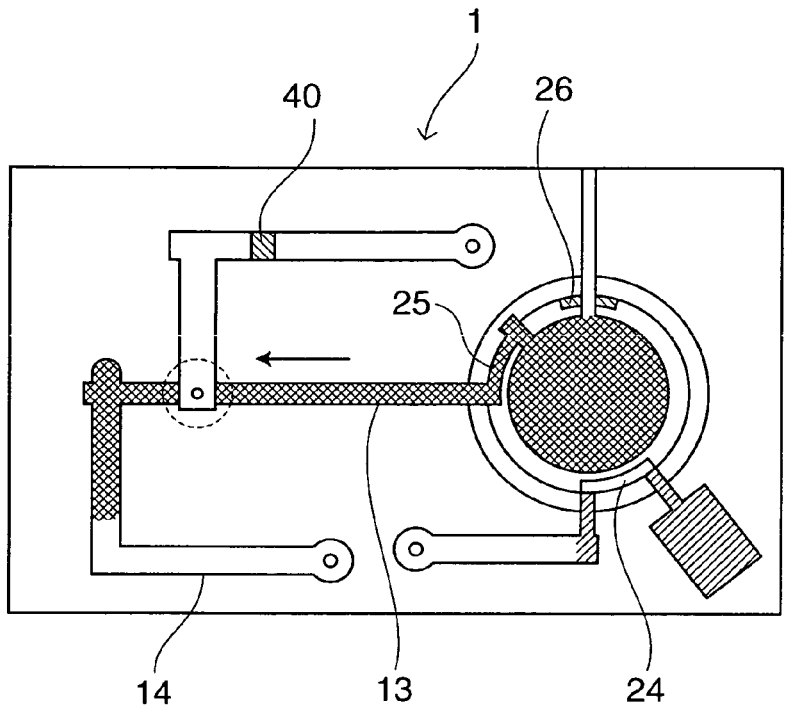

In turn, the syringe pump CP performs the sucking operation for a time period t8, and then the valve SV1 is closed (Steps S30 to S32), whereby the diluted sample is sucked into the channels 13, 14 from the diluent container 5 as shown in FIG. 51.

Figure 52:
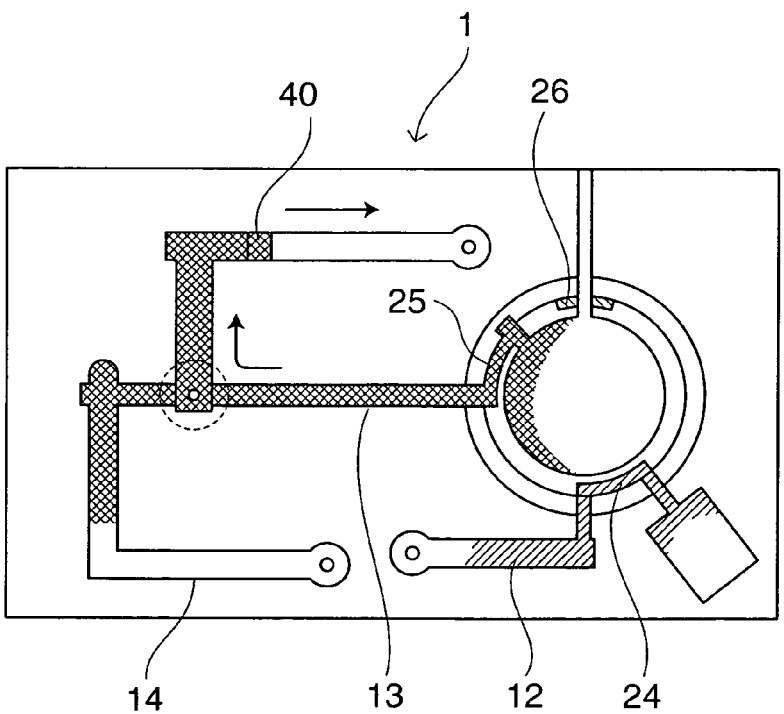

Subsequently, the syringe pump CP performs the sucking operation for a time period t9 with the valve SV3 being open, and then the valve SV3 is closed (Steps S33 to S36), whereby the diluted sample flows through the channel 13, the pellet 33 and the channel 15 from the diluent container 5 by suction as shown in FIG. 52, and 200 μL of the diluted sample is supplied into the absorbance measuring chamber 40. During this period, the control section 106 measures an electrical resistance between the electrodes 34 and 35 (Step S34).

On the other hand, the 200 μL diluted sample supplied into the absorbance measuring chamber 40 is further diluted by the 50 μL diluent preliminarily retained in the absorbance measuring chamber 40. As a result, a 625-time diluted sample is prepared. This diluted sample is irradiated with light from the laser diode 125, and the intensity of the transmitted light is detected by the photodiode 126. A detection value is stored in the control section 106 (Step S35a).

Figure 53:
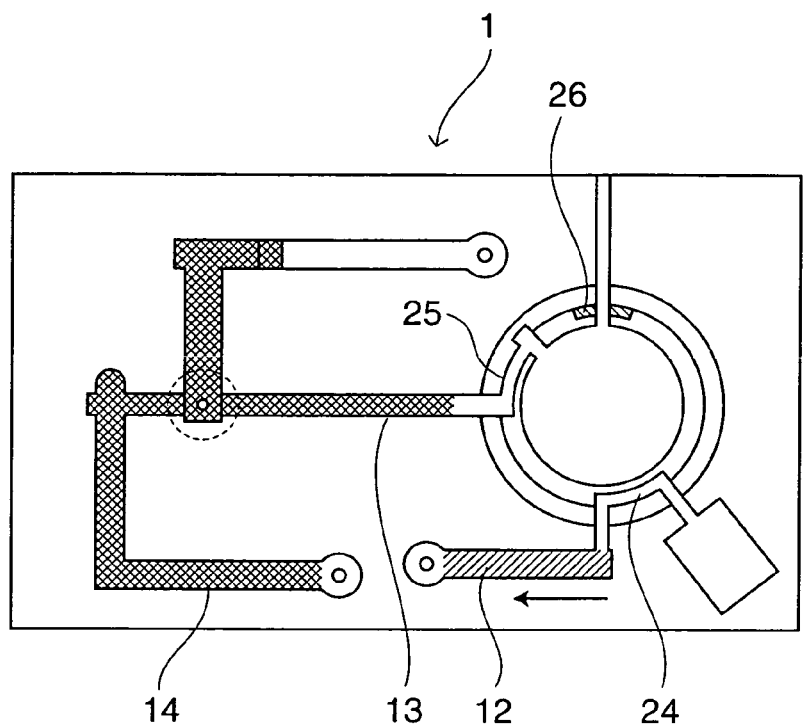

Subsequently, the syringe pump CP performs the sucking operation for a time period t10 with the valves SV1, SV2 being open, and then the valves SV1, SV2 are closed (Steps S37 to S39). Thus, the whole blood sample remaining in the sample receiving section 4 flows into the channel 12 and is retained in the channel 12, and the diluted sample remaining in the diluent container 5 flows into the channels 13, 14 and is retained in the channels 13, 14 as shown in FIGS. 52 and 53.

Figure 38A:
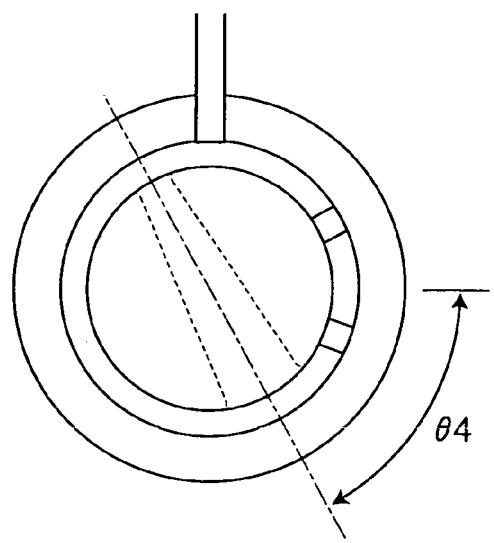
Figure 38B:
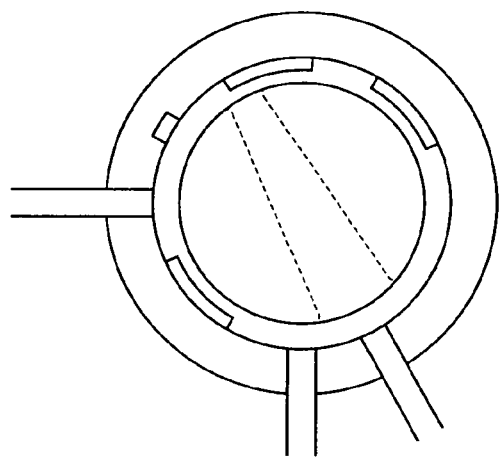
Figure 38C:
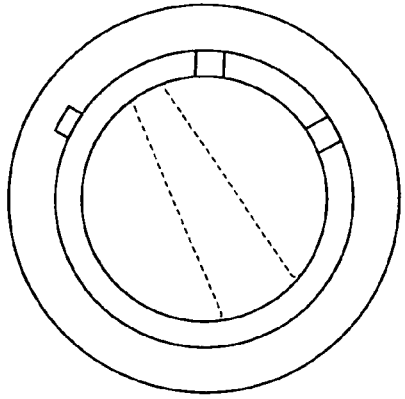
Figure 39:
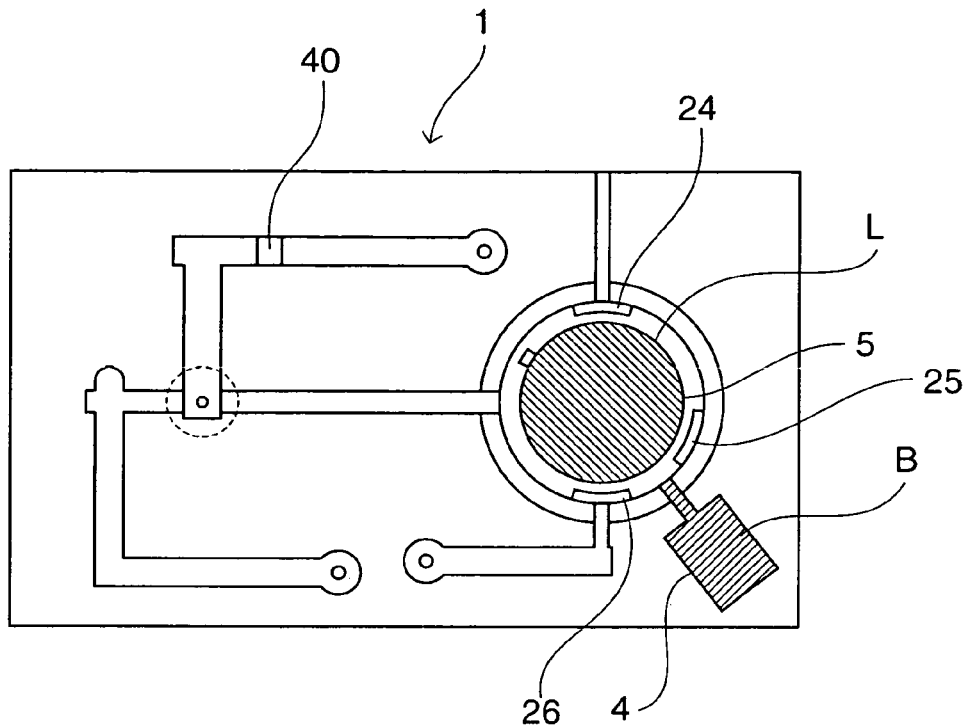
FIGS. 39 to 54 are diagrams for explaining the movement of a sample and a diluent in the first measuring unit.
Figure 54:
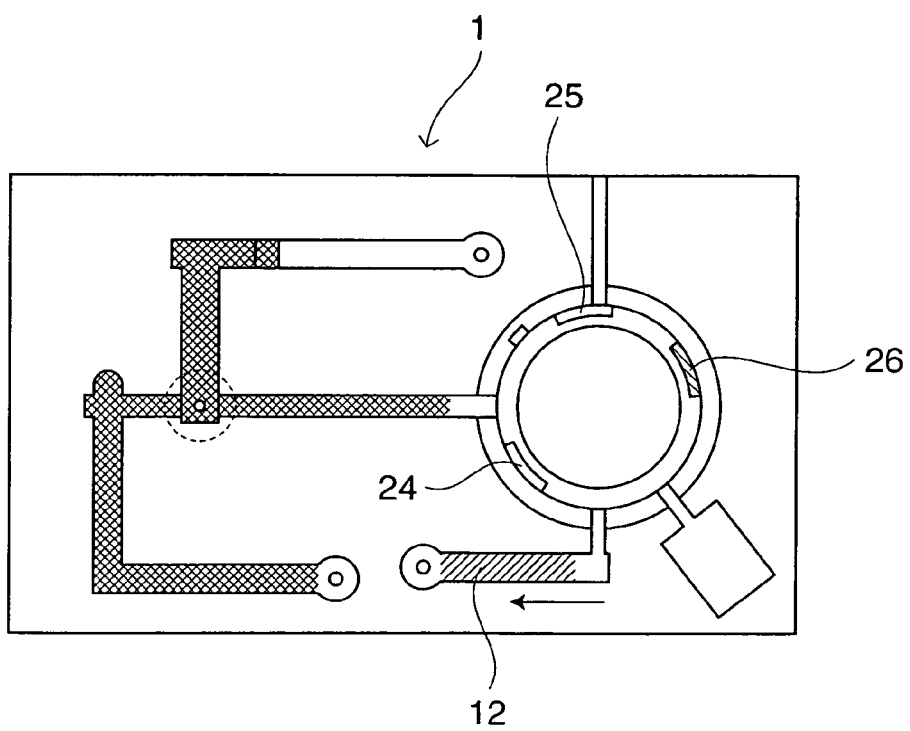

In turn, the stepping motor M1 is driven to rotate the inner cylinder 17 clockwise by an angle θ4 to a position as shown in FIGS. 38(a) to 38(c) (Steps S40 to S42). Thus, the vent hole 37 and the channel 11 are brought out of communication with the diluent container 5 and the channel 12, respectively, as shown in FIG. 54.

The measuring operation is thus completed with the residual whole blood sample retained in the channel 12 and with the diluted sample retained in the channels 13 to 15. Then, the results of the computation performed by the first and second computing sections 106a, 106b are outputted together with an identification code to the display section 108 and the printer 300, and the cover 111 is unlocked (Steps S43, S44). Then, the user opens the cover 111, and removes the first unit 1, which is in turn discarded (Steps S45, S46).

C-3. Measuring Operation with Second Measuring Unit

Figure 28:
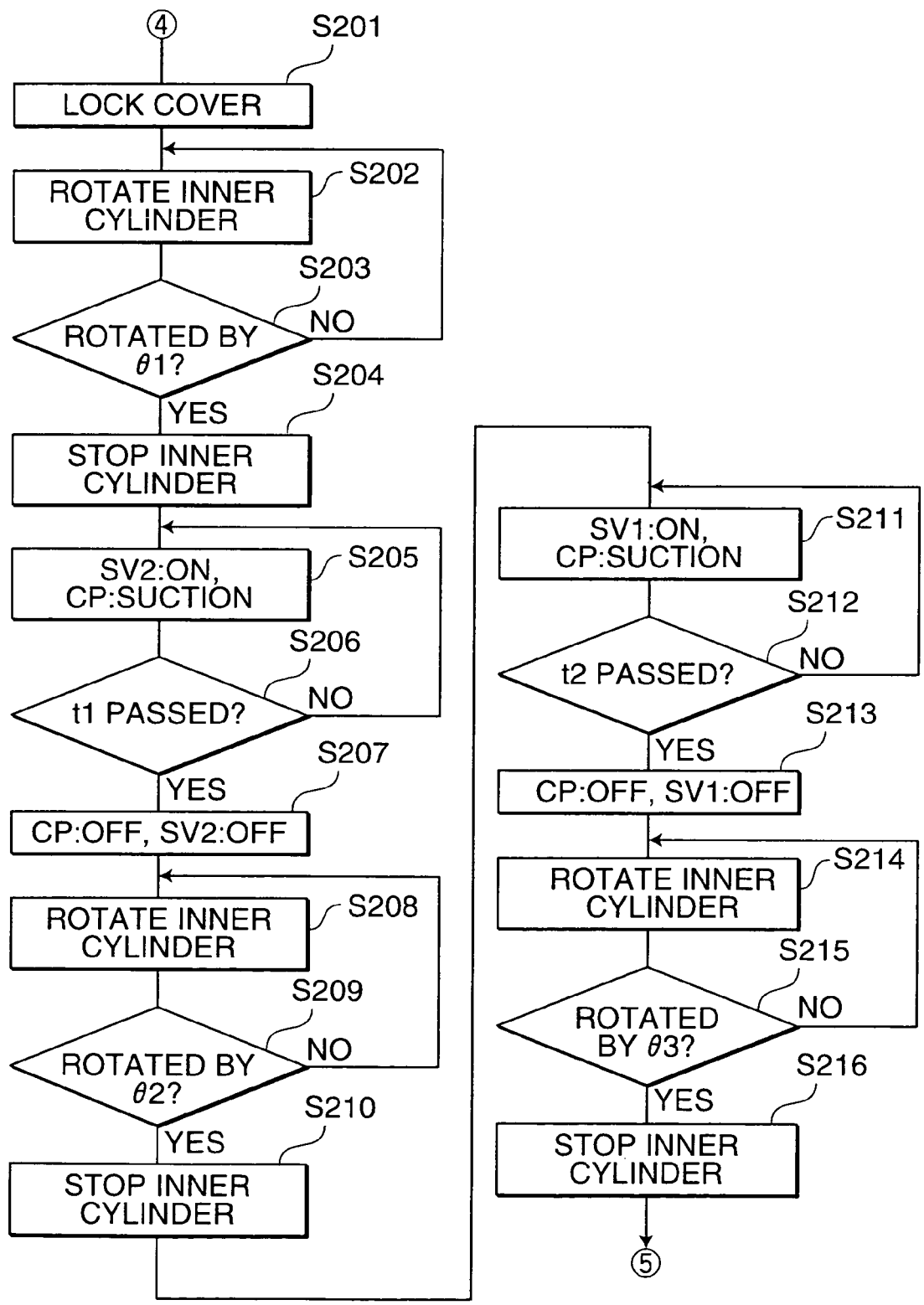
FIGS. 28 to 30 are flow charts for explaining an operation to be performed by the analyzer of FIG. 18 when the second measuring unit is set in the analyzer.
Figure 29:
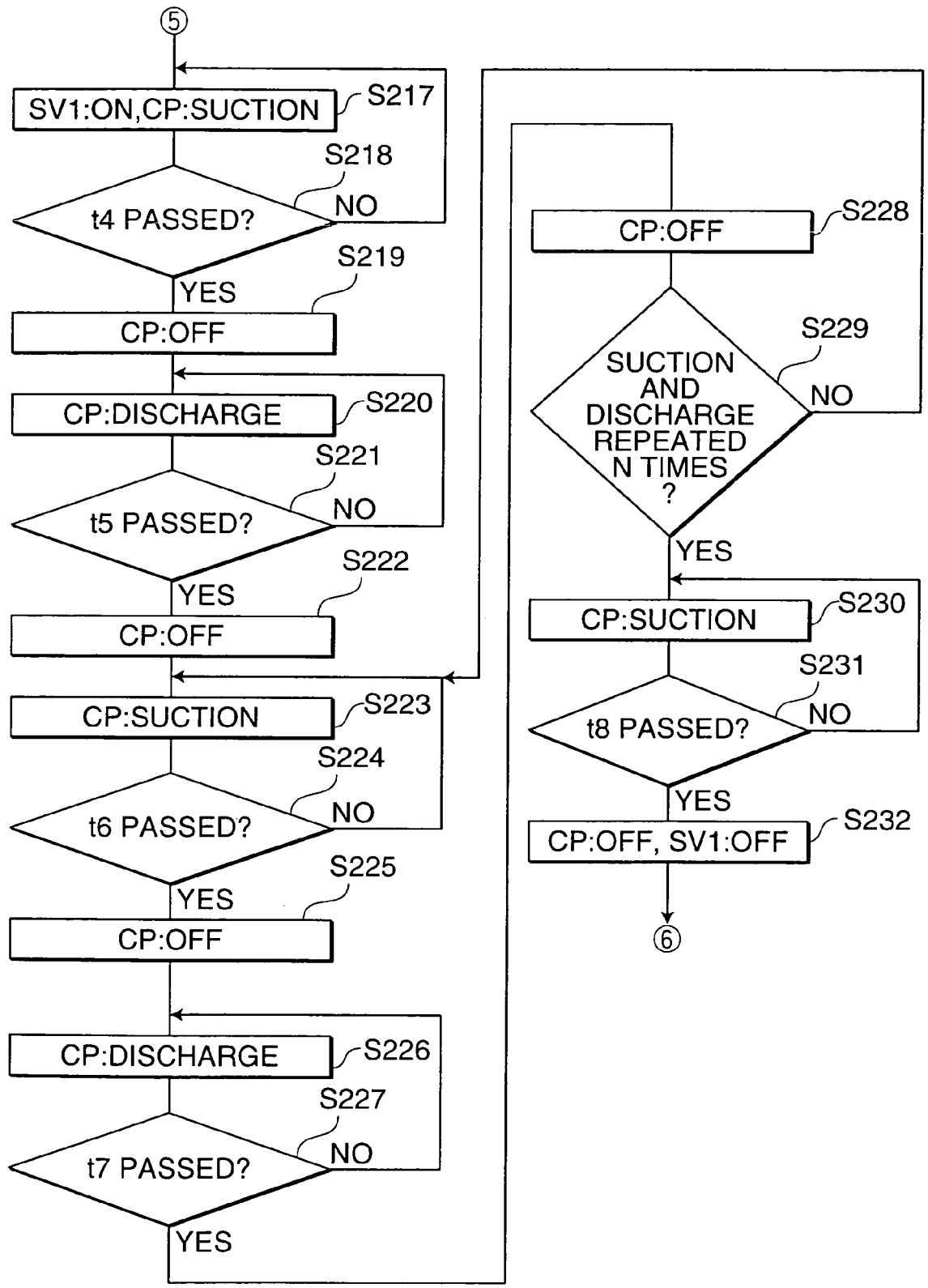
Figure 30:
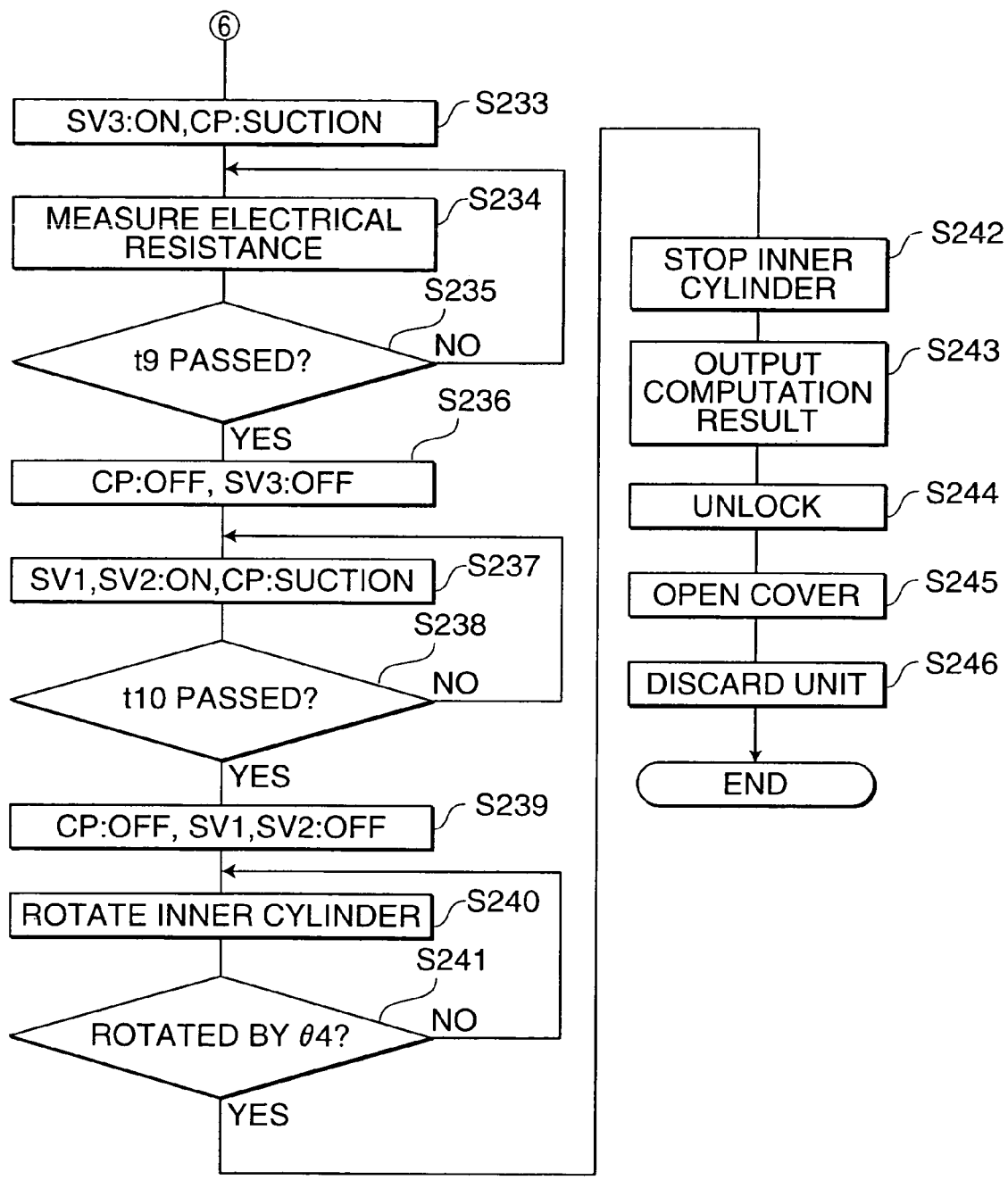

If it is judged in Step S113 of FIG. 24 that the measuring unit set in the measuring section 110 is the second unit 1a, the routine goes to Step S201 of FIG. 28. The solenoid RS is first actuated to lock the cover 111 (Step S201).

Then, the stepping motor M1 is driven to rotate the inner cylinder 17 clockwise by an angle θ1 from the initial position shown in FIGS. 34(a) to 34(c) and 57 to a position as shown in FIGS. 35(a) to 35(c) and 58 (Steps S202 to S204).

Figure 58:
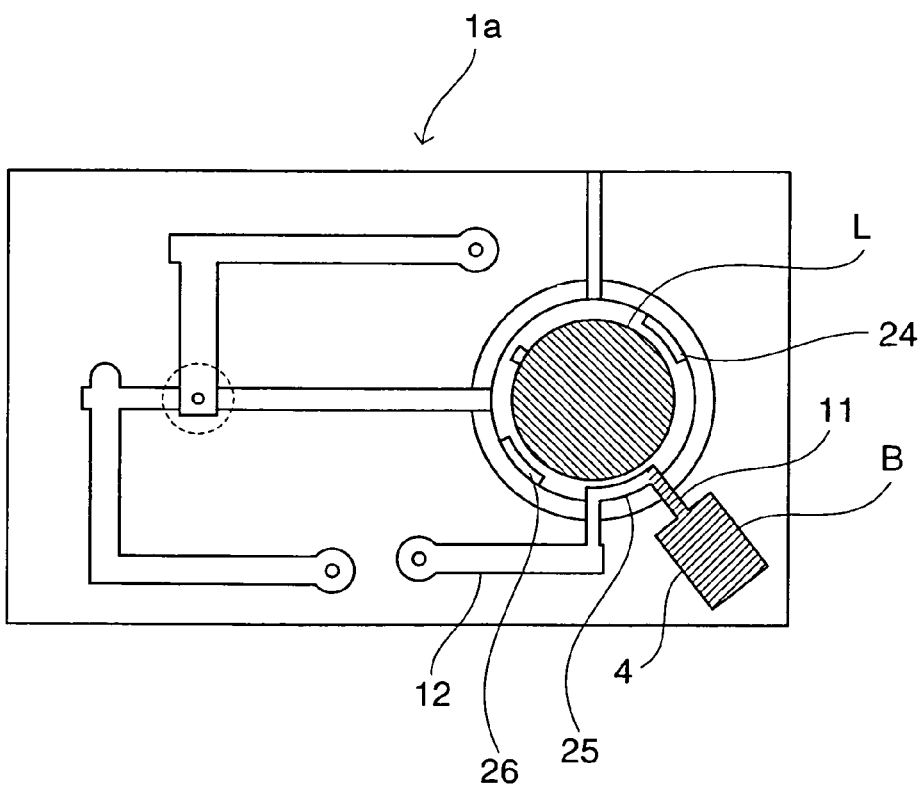
Figure 59:
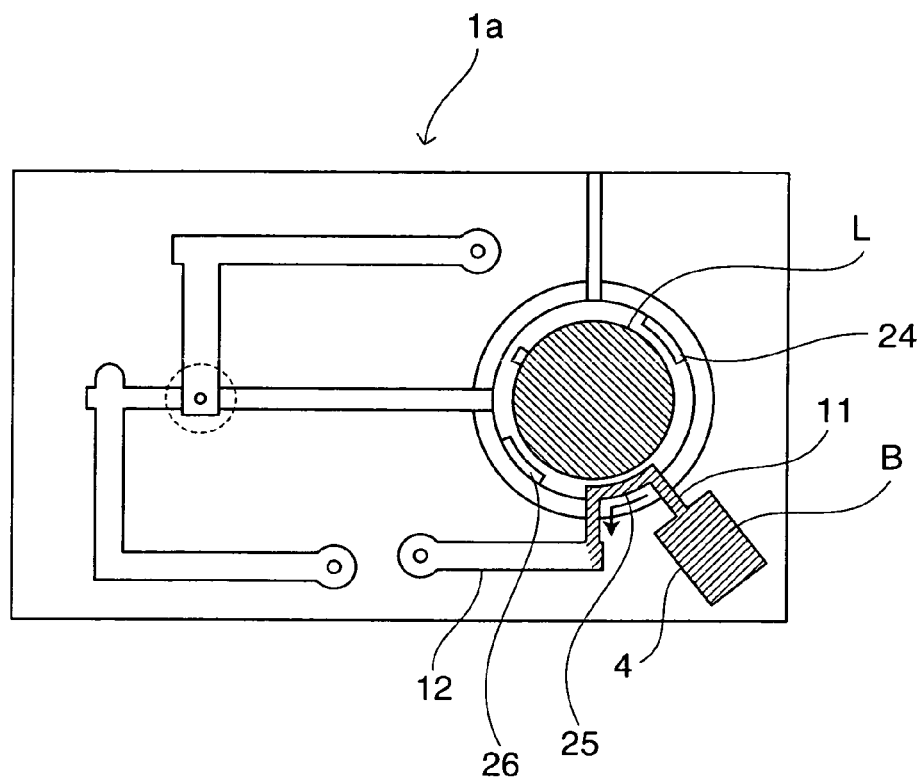

Thus, the channels 11, 12 communicate with each other via the lateral groove 25 to form the metering channel as shown in FIGS. 35(b) and 58. In this state, the syringe pump CP performs the sucking operation for a time period t1 with the valve SV2 being open, and then the valve SV2 is closed (Steps S205 to S207), whereby a whole blood sample B flows into the channel 12 from the sample receiving section 4 via the lateral groove 25 to fill the lateral groove 25 as shown in FIG. 59.

Figure 60:
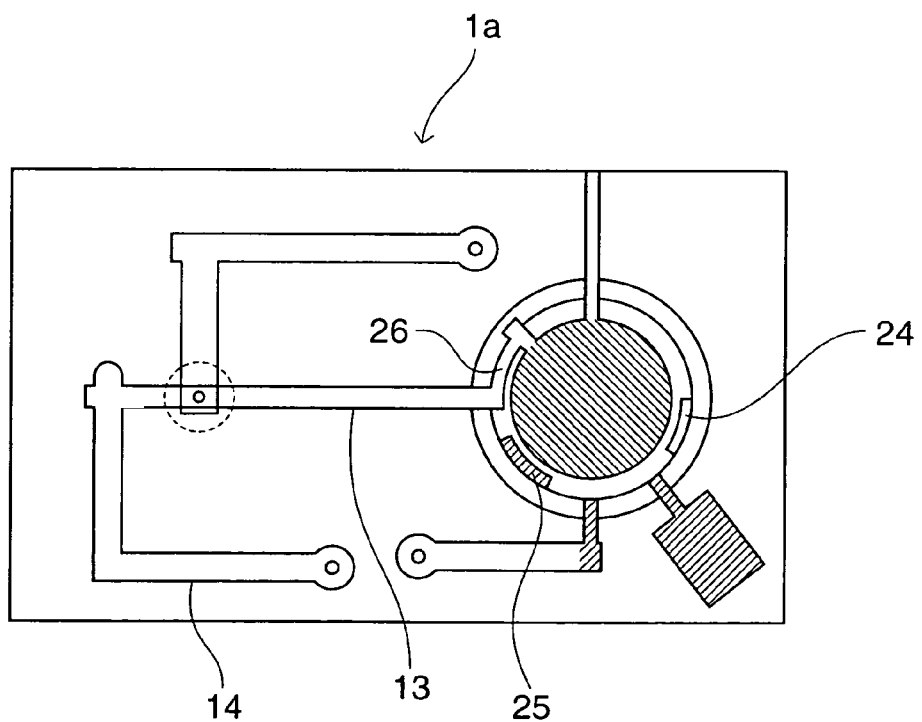

In turn, the stepping motor M1 is driven to rotate the inner cylinder 17 clockwise by an angle θ2 to a position as shown in FIGS. 36(a) to 36(c) and 60 (Steps S208 to S210). Thus, the sample is metered in a volume of 2 μL which is equivalent to the volume of the lateral groove 25, and separated by the inner circumferential surface of the outer cylinder 16 as shown in FIG. 60.

At the same time, the through-hole 22 of the inner cylinder 17 communicates with the vent hole 37 to open the upper portion of the diluent container 5 to the atmosphere as shown in FIG. 36(a), and the channel 13 communicates with the bottom of the diluent container 5 via the lateral groove 26, the vertical groove 32 and the through-hole 31 as shown in FIGS. 36(b) and 36(c).

Figure 61:
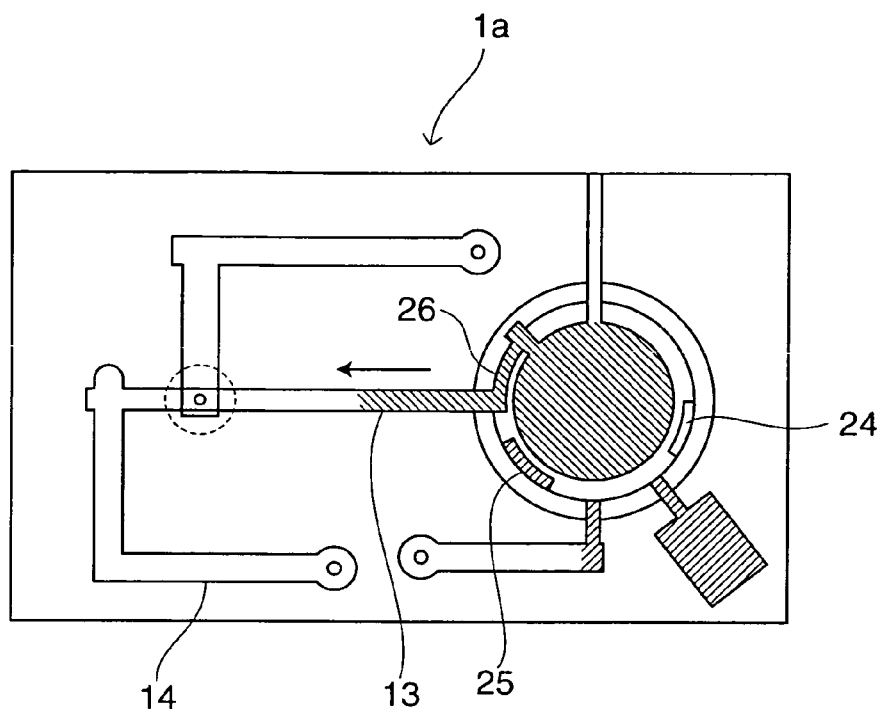

In turn, the syringe pump CP performs the sucking operation for a time period t2 with the valve SV1 being open, and then the valve SV1 is closed (Steps S211 to S213), whereby the diluent L is sucked into the channel 13 from the diluent container 5 as shown in FIG. 61.

Figure 62:
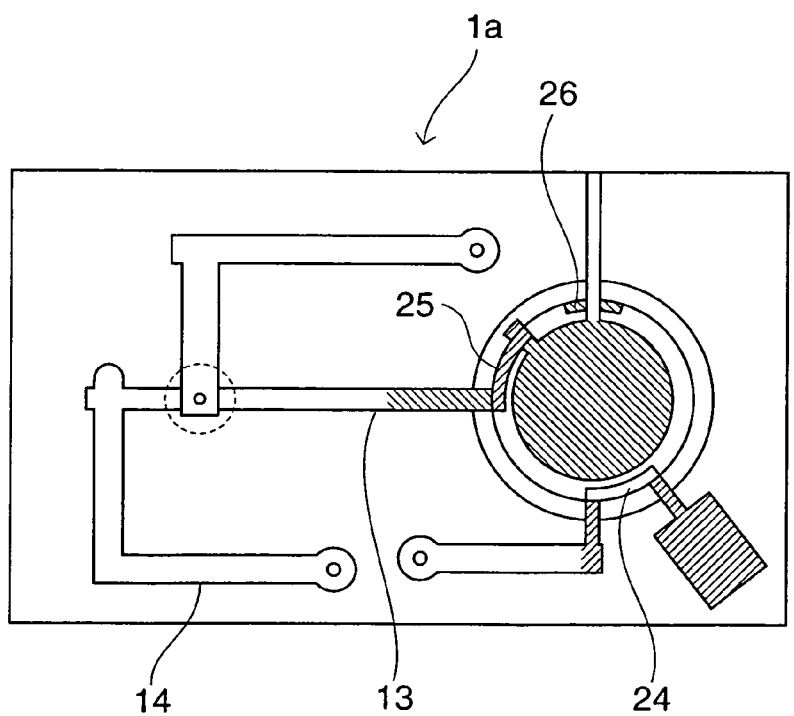

Subsequently, the stepping motor M1 is driven to rotate the inner cylinder 17 clockwise by an angle θ3 to a position as shown in FIG. 62 (Steps S214 to S216).

Thus, the through-hole 23 of the inner cylinder 17 communicates with the vent hole 37 to open the upper portion of the diluent container 5 to the atmosphere as shown in FIG. 37(a), and the channel 13 communicates with the bottom of the diluent container 5 via the lateral groove 25, the vertical groove 32 and the through-hole 30 to form the agitation channel as shown in FIGS. 37(b), 37(c) and 62. At the same time, the channel 11 communicates with the channel 12 via the lateral groove 24 as shown in FIG. 37(b).

Figure 63:
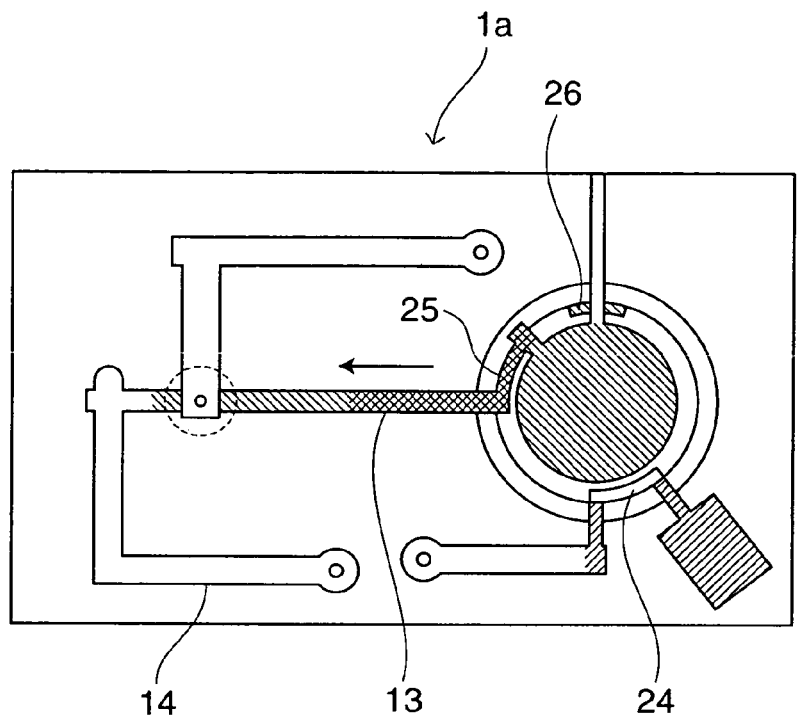

Then, the valve SV1 is opened, and the syringe pump CP further performs the sucking operation for a time period t4 (Steps S217 to S219), whereby the diluent L is sucked into the channel 13 from the diluent container 5 together with the metered sample in the lateral groove 25 as shown in FIG. 63.

Figure 64:
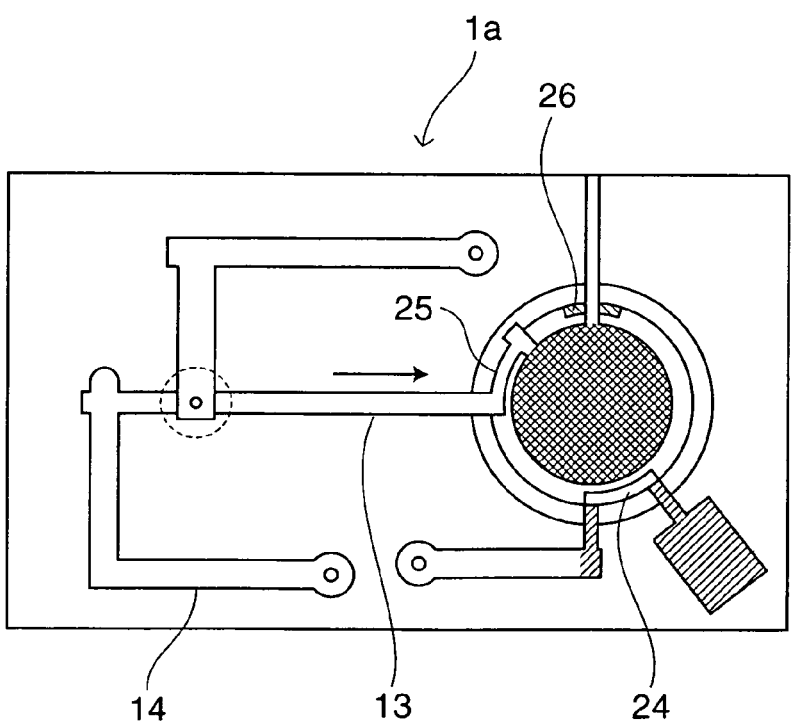

In turn, the syringe pump CP performs the discharging operation for a time period t5 (Steps S220 to S222), whereby the sample and the diluent are fed back into the diluent container 5 as shown in FIG. 64.

Figure 65:
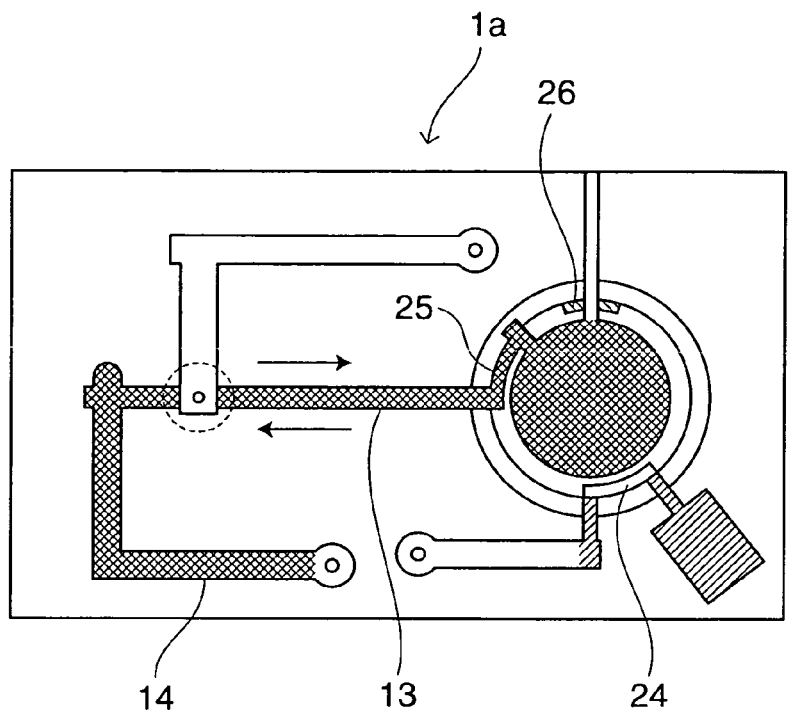
Figure 66:
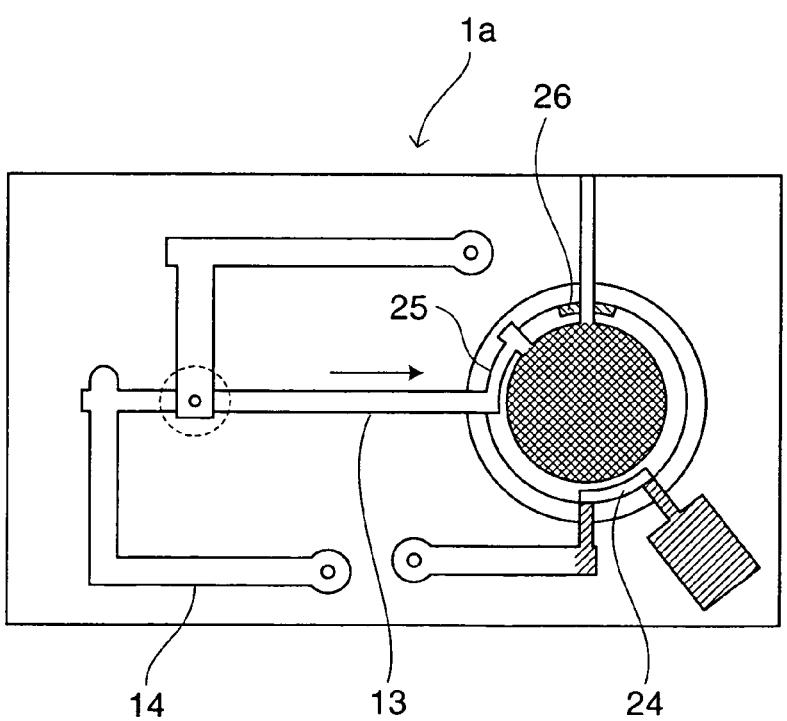

Subsequently, the syringe pump CP repeats a t6-period sucking operation and a t7-period discharging operation N times (Steps S223 to S229), whereby the diluent and the sample flow back and forth between the channels 13, 14 and the diluent container 5 as shown in FIG. 65. Thus, the diluent and the sample are sufficiently mixed and agitated for preparation of a 500-time diluted sample. The diluted sample is retained in the diluent container 5 as shown in FIG. 66.

Figure 67:
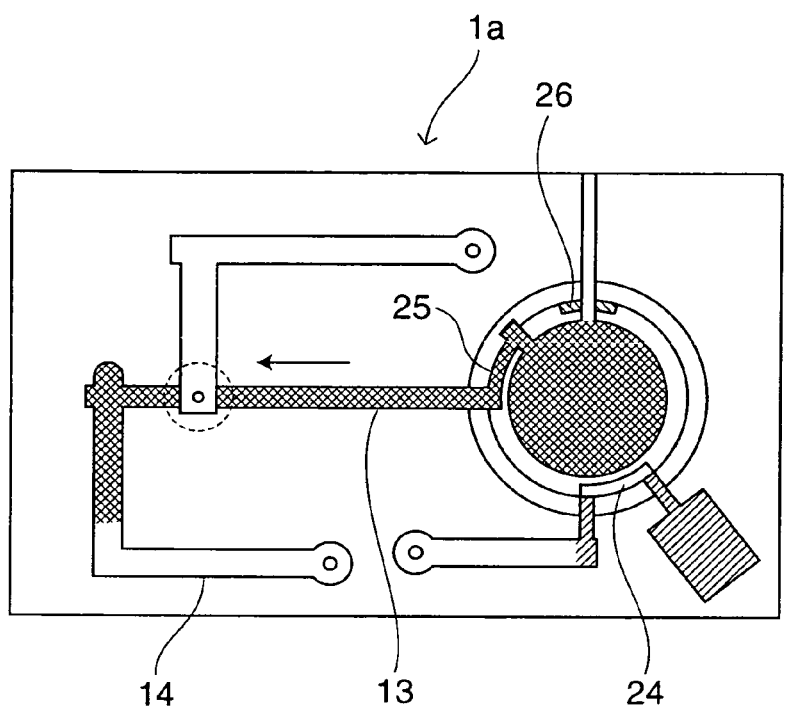

In turn, the syringe pump CP performs the sucking operation for a time period t8, and then the valve SV1 is closed (Steps S230 to S232), whereby the diluted sample is sucked into the channels 13, 14 from the diluent container 5 as shown in FIG. 67.

Figure 68:
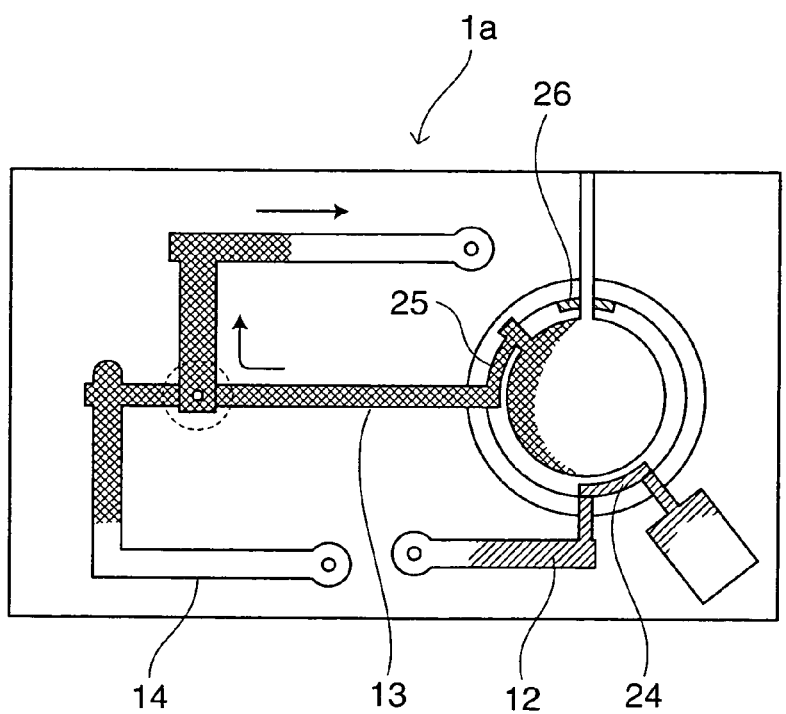

Subsequently, the syringe pump CP performs the sucking operation for a time period t9 with the valve SV3 being open, and then the valve SV3 is closed (Steps S233 to S236), whereby the diluted sample flows through the channel 13, the pellet 33 and the channel 15 from the diluent container 5 by suction as shown in FIG. 68. During this period, the control section 106 measures an electrical resistance between the electrodes 34 and 35 (Step S234).

Figure 69:
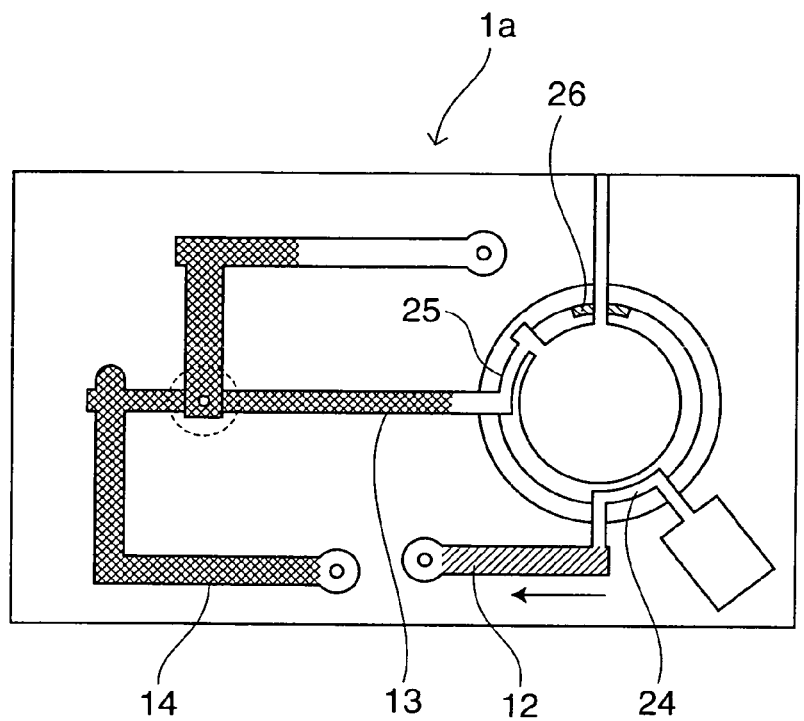

In turn, the syringe pump CP performs the sucking operation for a time period t10 with the valves SV1, SV2 being open, and then the valves SV1, SV2 are closed (Steps S237 to S239). Thus, the whole blood sample remaining in the sample receiving section 4 flows into the channel 12 and is retained in the channel 12, and the diluted sample remaining in the diluent container 5 flows into the channels 13, 14 and is retained in the channels 13, 14 as shown in FIGS. 68 and 69.

Figure 70:
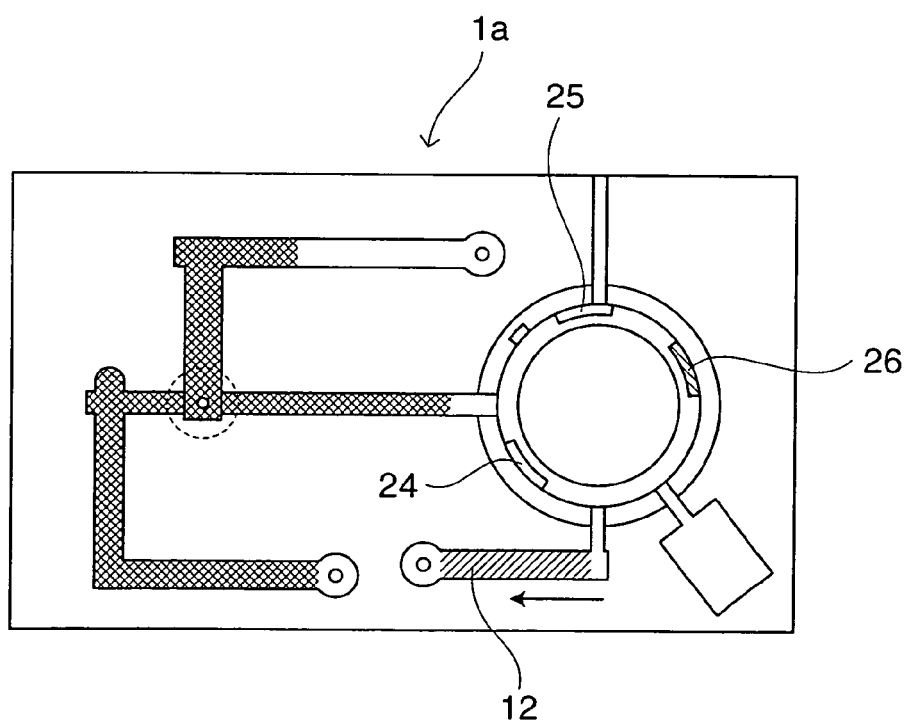
Figure 71:
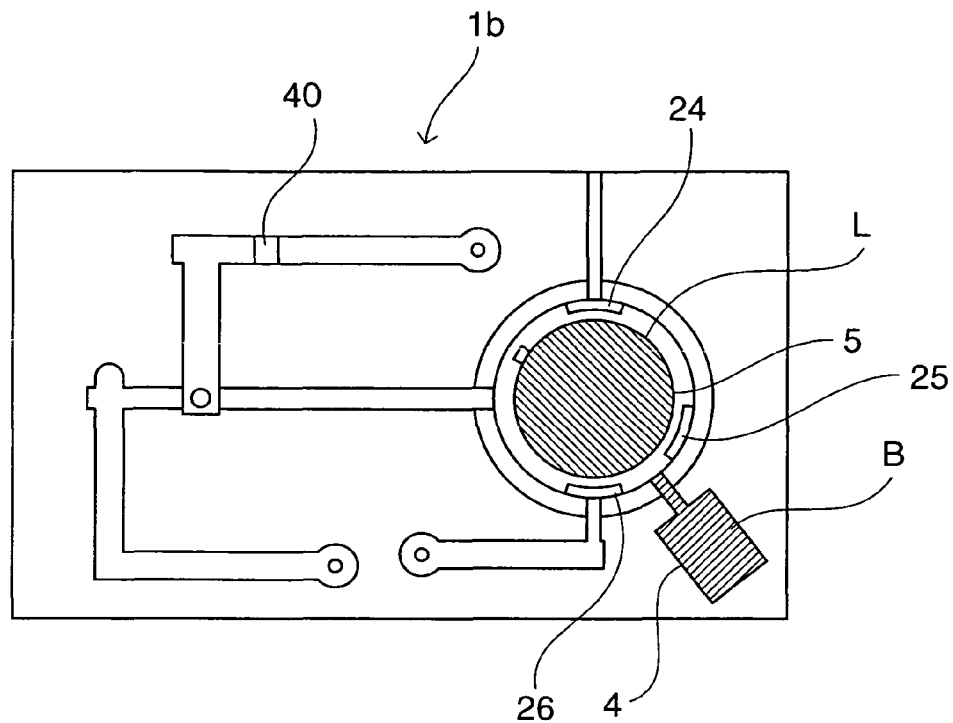
FIGS. 71 to 86 are diagrams for explaining the movement of a sample and a diluent in the third measuring unit.

Then, the stepping motor M1 is driven to rotate the inner cylinder 17 clockwise by an angle θ4 to a position as shown in FIGS. 38(a) to 38(c) (Steps S240 to S242). Thus, the vent hole 37 and the channel 11 are brought out of communication with the diluent container 5 and the channel 12, respectively, as shown in FIG. 70.

The measuring operation is thus completed with the residual whole blood sample retained in the channel 12 and with the diluted sample retained in the channels 13 to 15. Then, the result of the computation performed by the first computing section 106a is outputted together with an identification code to the display section 108 and the printer 300, and the cover 111 is unlocked (Steps S243, S244). Then, the user opens the cover 111, and removes the second unit 1a, which is in turn discarded (Steps S245, S246).

C-4. Measuring Operation with Third Measurement Unit

Figure 31:
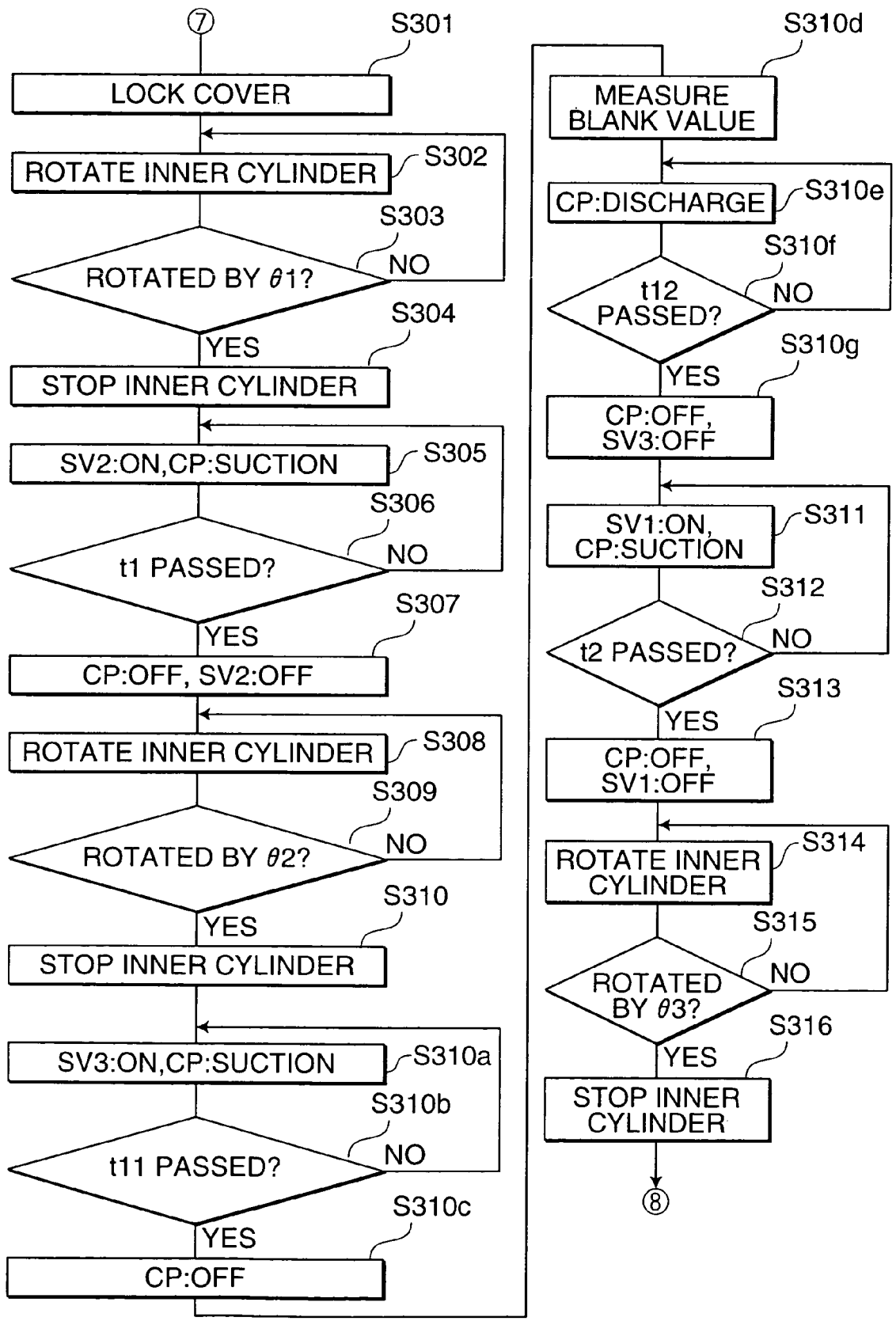
FIGS. 31 to 33 are flow charts for explaining an operation to be performed by the analyzer of FIG. 18 when the third measuring unit is set in the analyzer.
Figure 32:
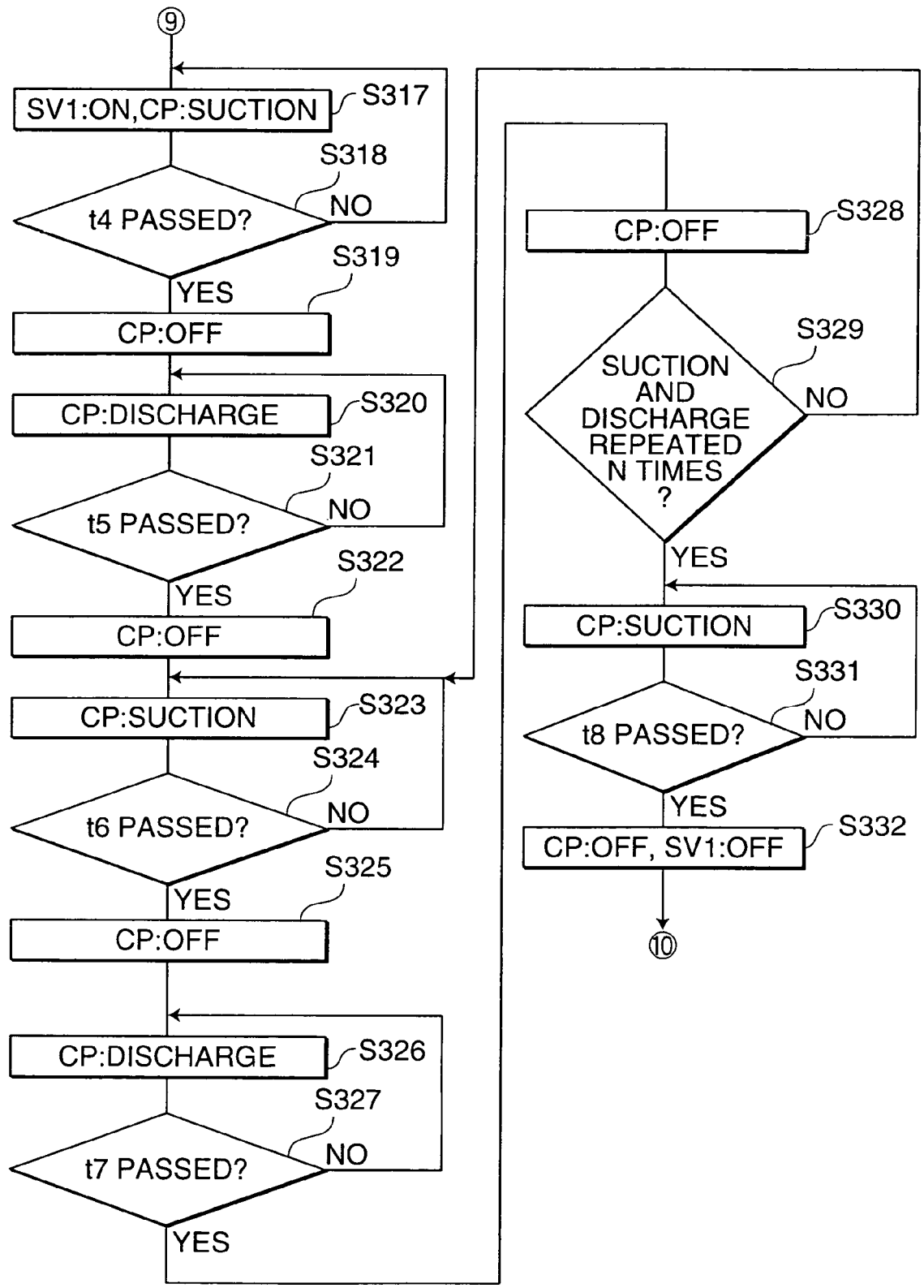
Figure 33:
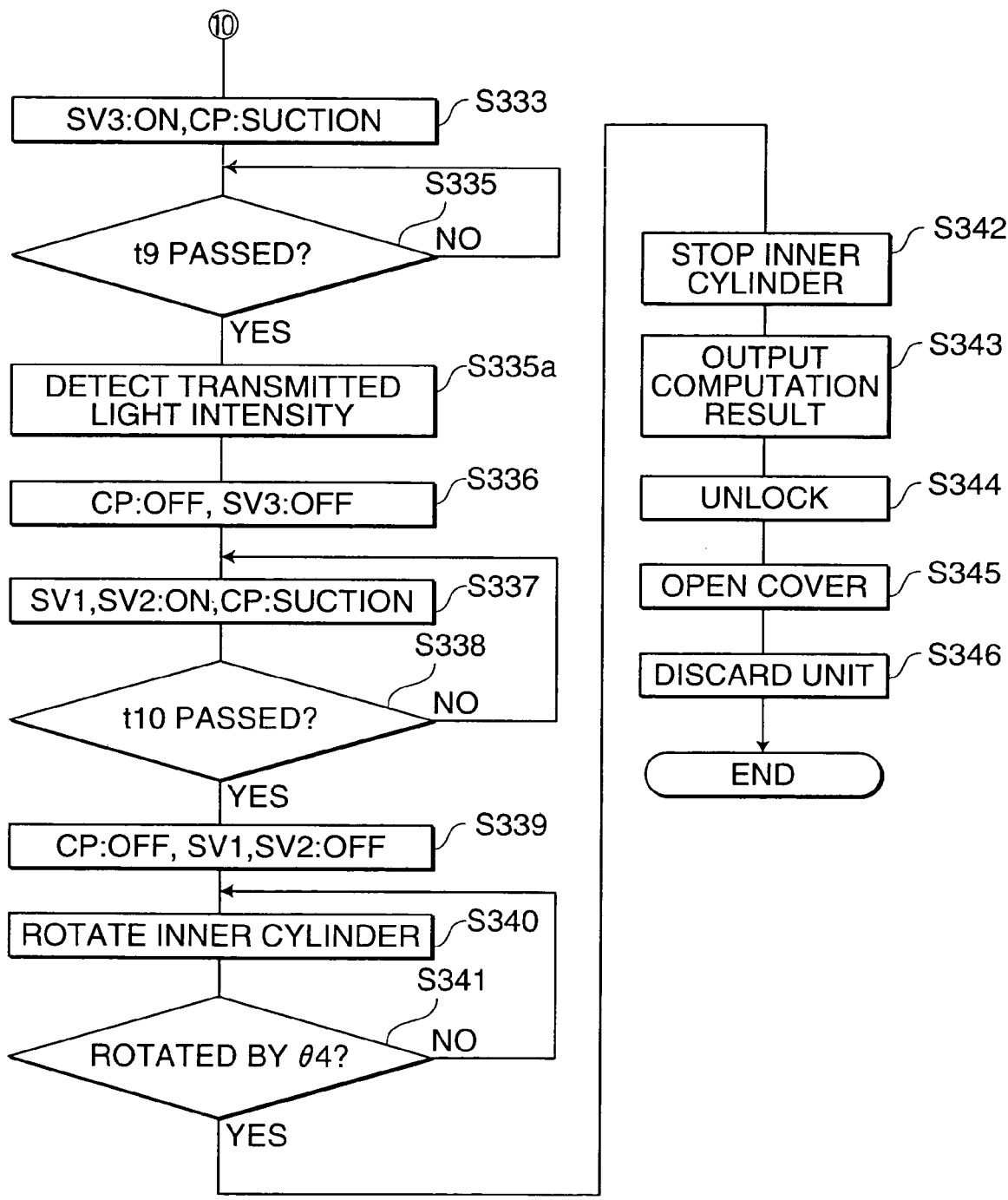
Figure 34A:
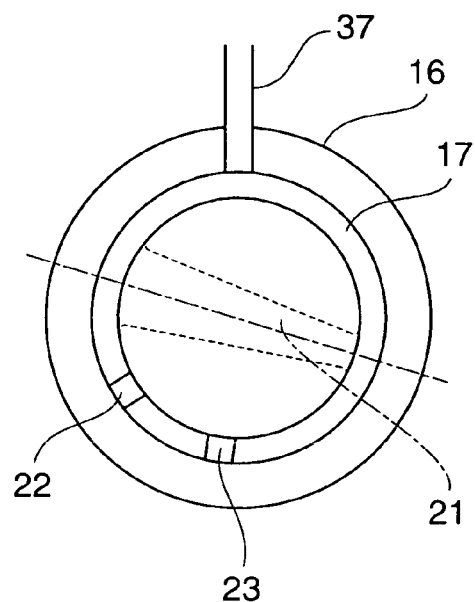
FIGS. 34(a) to 34(c), FIGS. 35(a) to 35(c), FIGS. 36(a) to 36(c), FIGS. 37(a) to 37(c) and FIGS. 38(a) to 38(c) are diagrams for explaining the operation of the rotary valve in each of the first to third measuring units.
Figure 34B:
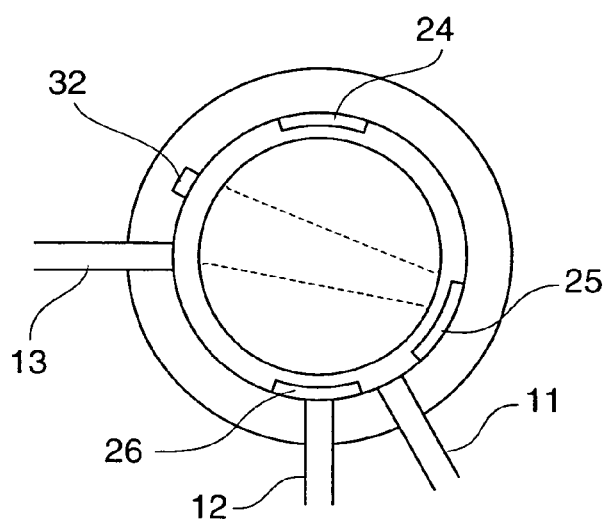
Figure 34C:
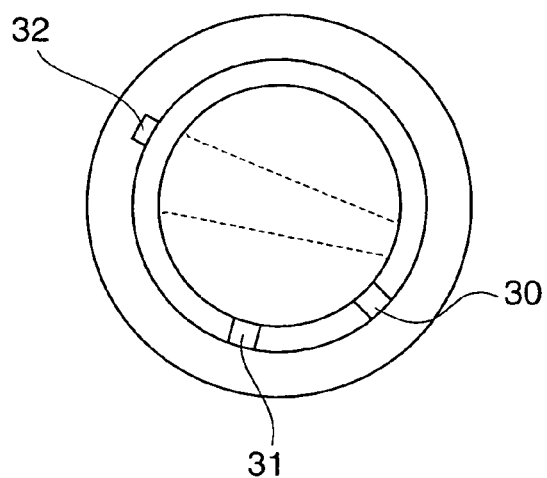

If it is judged in Step S114 of FIG. 24 that the measuring unit set in the measuring section 110 is the third unit 1b, the routine goes to Step S301 of FIG. 31. The solenoid RS is first actuated to lock the cover 111 (Step S301). Then, the stepping motor M1 is driven to rotate the inner cylinder 17 clockwise by an angle θ1 from the initial position shown in FIGS. 34(a) to 34(c) and 71 to a position as shown in FIGS. 35(a) to 35(c) and 72 (Steps S302 to S304).

Figure 72:
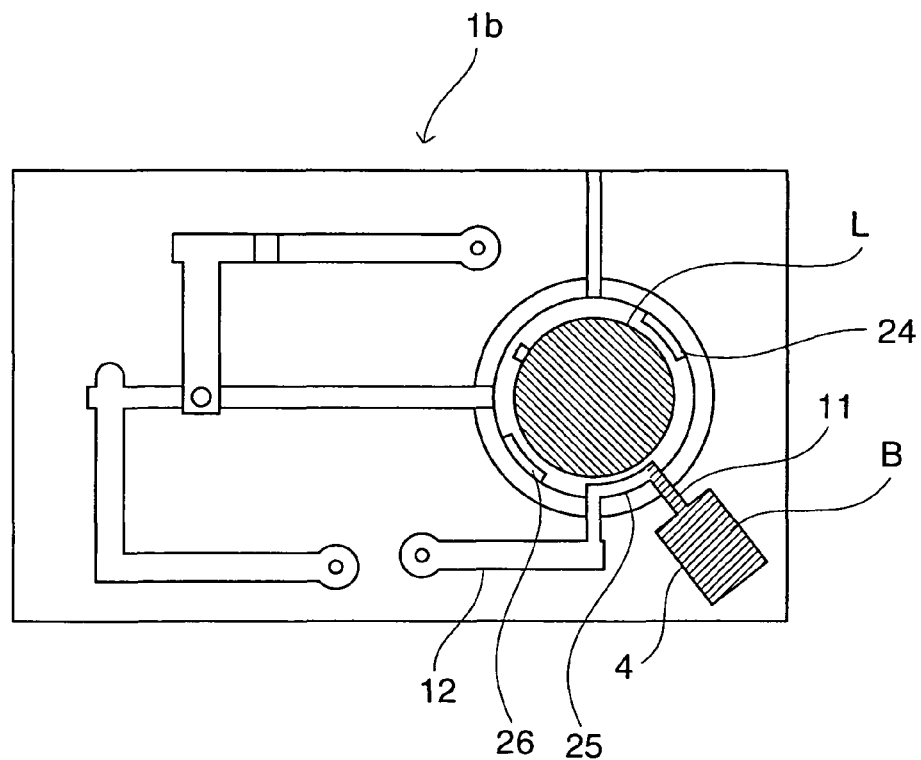
Figure 73:
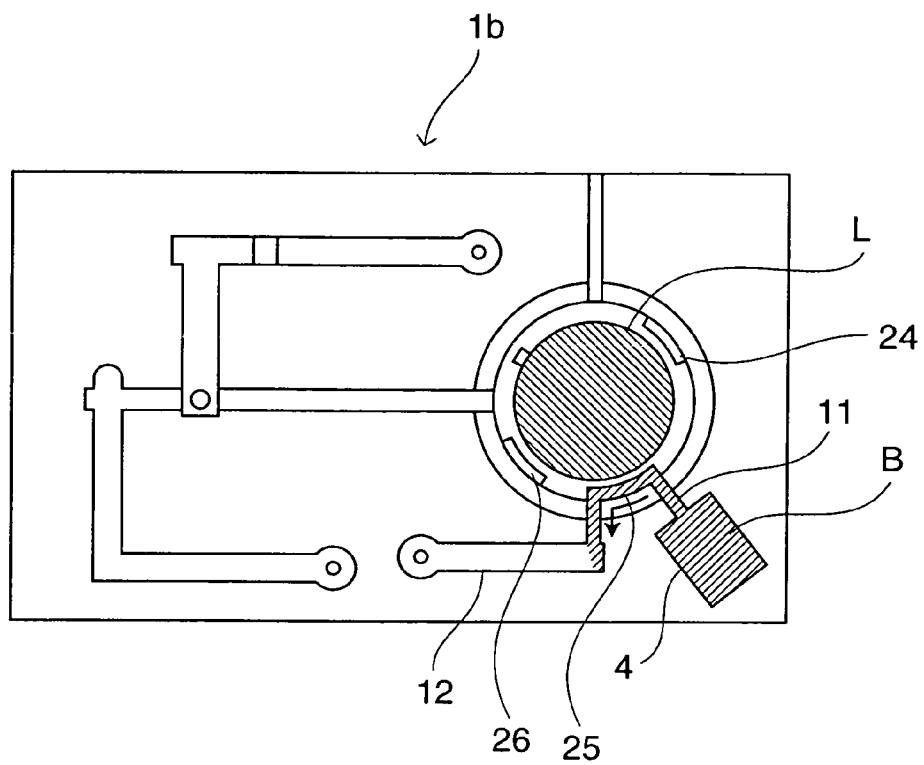

Thus, the channels 11, 12 communicate with each other via the lateral groove 25 to form the metering channel as shown in FIGS. 35(b) and 72. In this state, the syringe pump CP performs the sucking operation for a time period t1 with the valve SV2 being open, and then the valve SV2 is closed (Steps S305 to S307), whereby a whole blood sample B flows into the channel 12 from the sample receiving section 4 via the lateral groove 25 to fill the lateral groove 25 as shown in FIG. 73.

Figure 74:
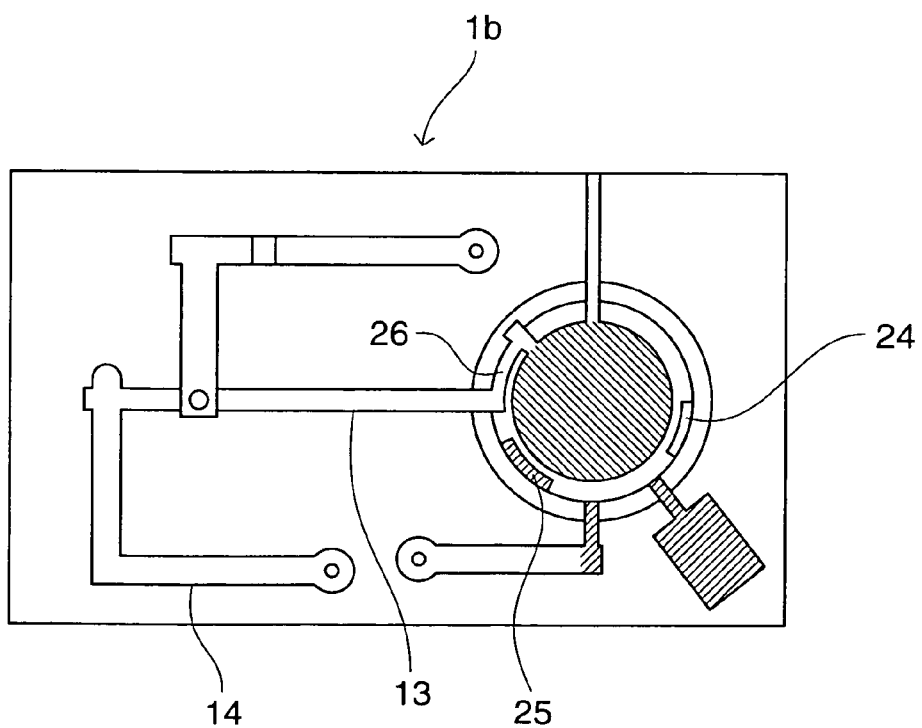

In turn, the stepping motor M1 is driven to rotate the inner cylinder 17 clockwise by an angle θ2 to a position as shown in FIGS. 36(a) to 36(c) and 74 (Steps S308 to S310). Thus, the sample is metered in a volume of 2 μL which is equivalent to the volume of the lateral groove 25, and separated by the inner circumferential surface of the outer cylinder 16 as shown in FIG. 74.

At the same time, the through-hole 22 of the inner cylinder 17 communicates with the vent hole 37 to open the upper portion of the diluent container 5 to the atmosphere as shown in FIG. 36(a), and the channel 13 communicates with the bottom of the diluent container 5 via the lateral groove 26, the vertical groove 32 and the through-hole 31 as shown in FIGS. 36(b) and 36(c).

Figure 75:
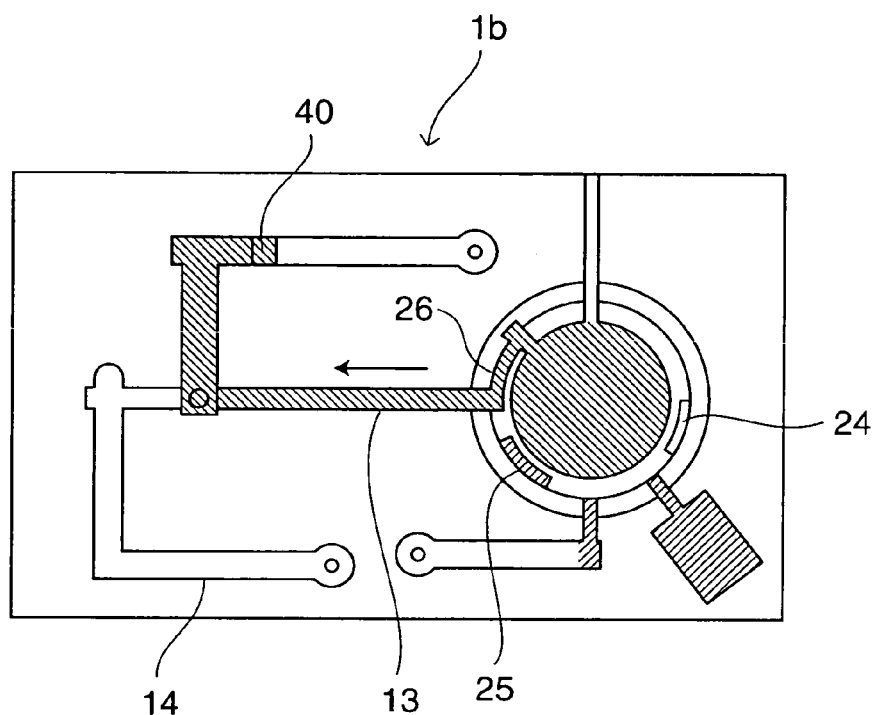
Figure 76:
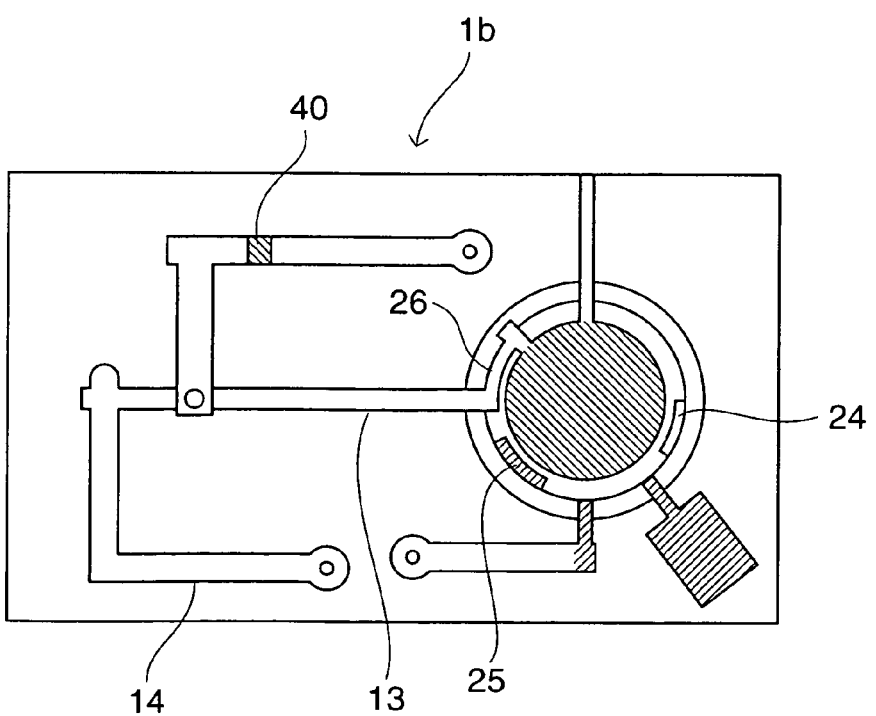

Then, the valve SV3 is opened, and the syringe pump CP performs the sucking operation for a time period t11 (Steps S310a to S310c), whereby the diluent L is introduced into the channel 15 from the diluent container 5 through the channel 13 as shown in FIG. 75. Thus, 50 μL of the diluent L is retained in the absorbance measuring chamber 40. Then, the laser diode 125 emits light toward the absorbance measuring chamber 40, and the photodiode 126 detects the intensity of light transmitted through the absorbance measuring chamber 40. A detection value (blank value) is stored in the control section 106 (Step S310d). Then, the syringe pump CP performs the discharging operation for a time period t12, and the valve SV3 is closed (Steps S310e to S310g). Thus, the diluent L in the channels 15, 13 is fed back into the diluent container 5 as shown in FIG. 76.

Figure 77:
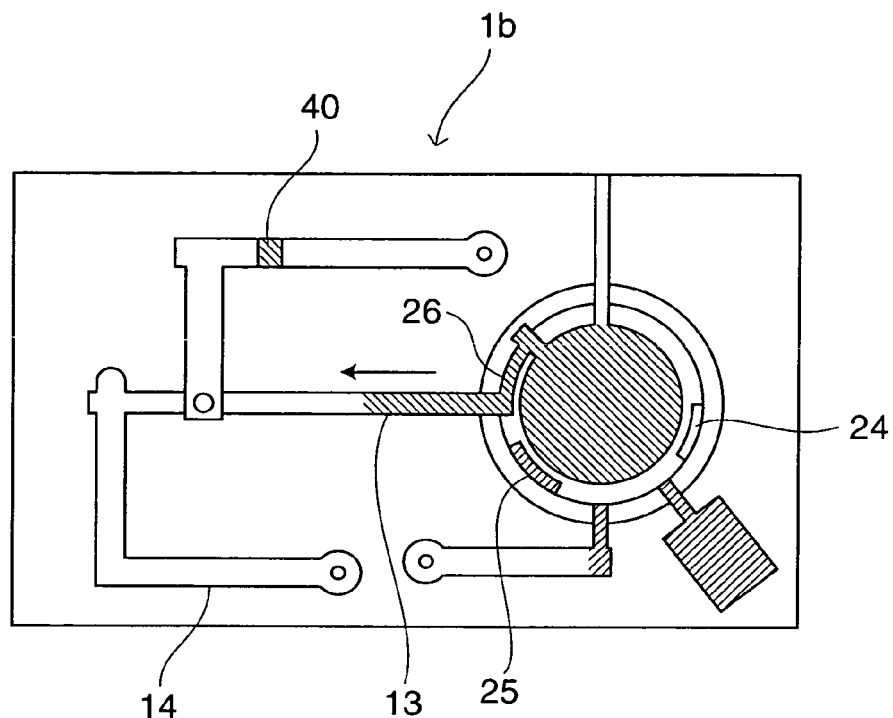

In turn, the syringe pump CP performs the sucking operation for a time period t2 with the valve SV1 being open, and then the valve SV1 is closed (Steps S311 to S313), whereby the diluent L is sucked into the channel 13 from the diluent container 5 as shown in FIG. 77.

Figure 78:
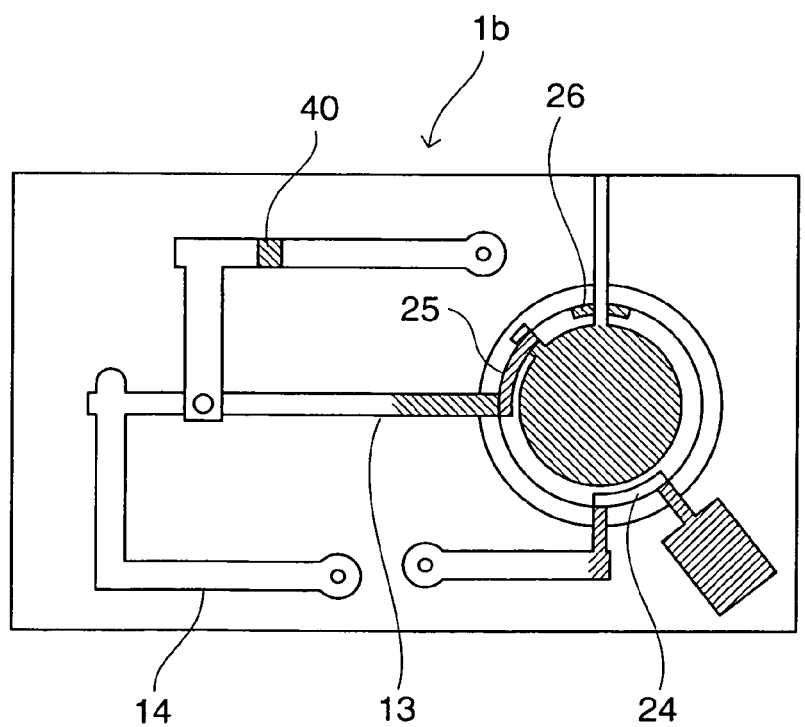

Subsequently, the stepping motor M1 is driven to rotate the inner cylinder 17 clockwise by an angle θ3 to a position as shown in FIG. 78 (Steps S314 to S316).

Thus, the through-hole 23 of the inner cylinder 17 communicates with the vent hole 37 to open the upper portion of the diluent container 5 to the atmosphere as shown in FIG. 37(a), and the channel 13 communicates with the bottom of the diluent container 5 via the lateral groove 25, the vertical groove 32 and the through-hole 30 to form the agitation channel as shown in FIGS. 37(b), 37(c) and 78. At the same time, the channel 11 communicates with the channel 12 via the lateral groove 24 as shown in FIG. 37(b).

Figure 79:
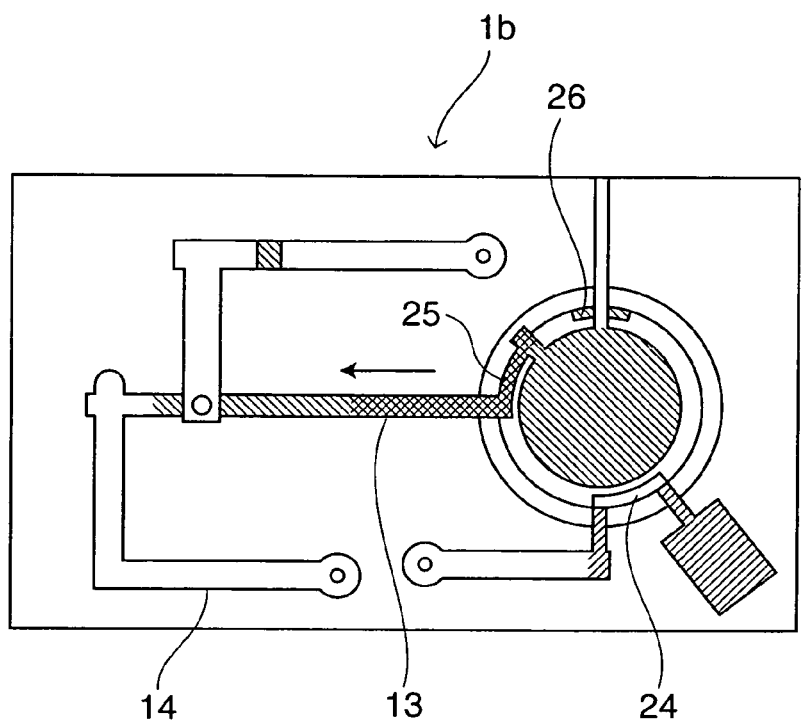

Then, the valve SV1 is opened, and the syringe pump CP further performs the sucking operation for a time period t4 (Steps S317 to S319), whereby the diluent L is sucked into the channel 13 from the diluent container 5 together with the metered sample in the lateral groove 25 as shown in FIG. 79.

Figure 80:
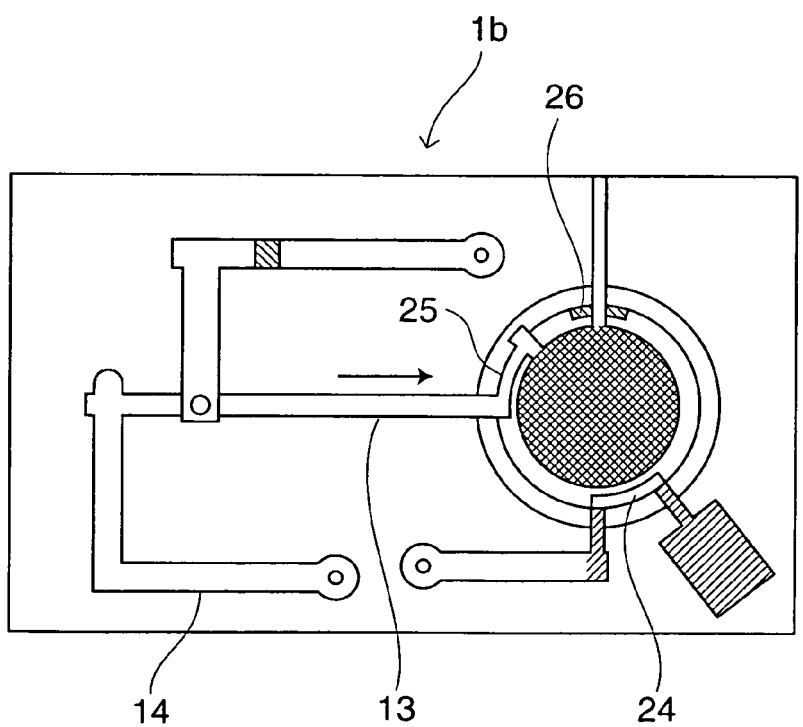

In turn, the syringe pump CP performs the discharging operation for a time period t5 (Steps S320 to S322), whereby the sample and the diluent are fed back into the diluent container 5 as shown in FIG. 80.

Figure 81:
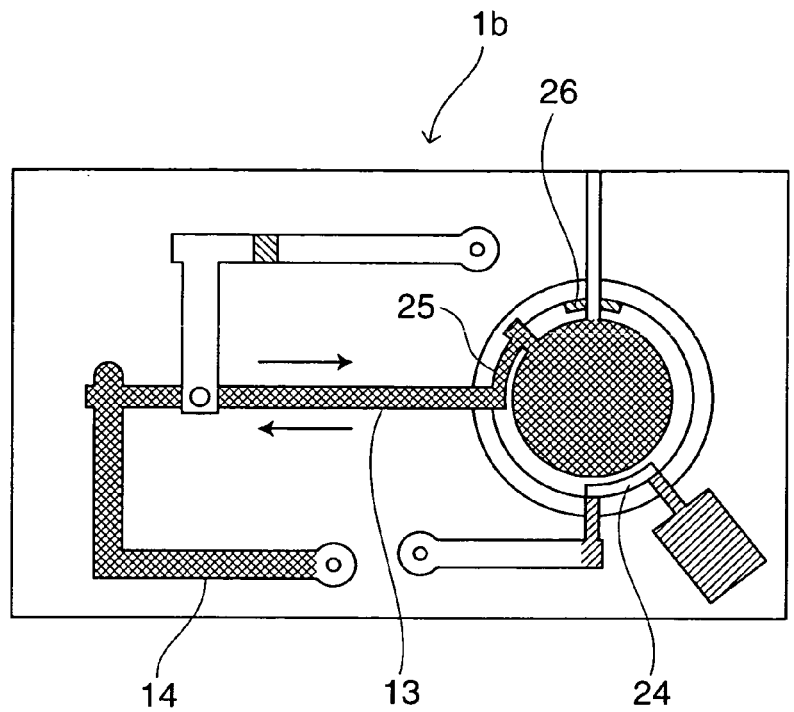
Figure 82:
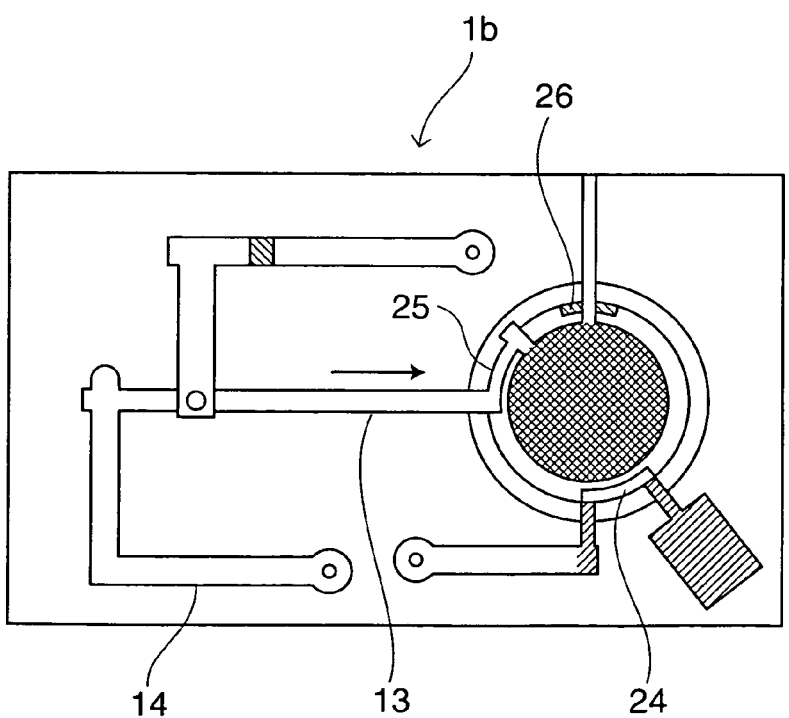

Subsequently, the syringe pump CP repeats a t6-period sucking operation and a t7-period discharging operation N times (Steps S323 to S329), whereby the diluent and the sample flow back and forth between the channels 13, 14 and the diluent container 5 as shown in FIG. 81. Thus, the diluent and the sample are sufficiently mixed and agitated for preparation of a 500-time diluted sample. The diluted sample is retained in the diluent container 5 as shown in FIG. 82.

Figure 83:
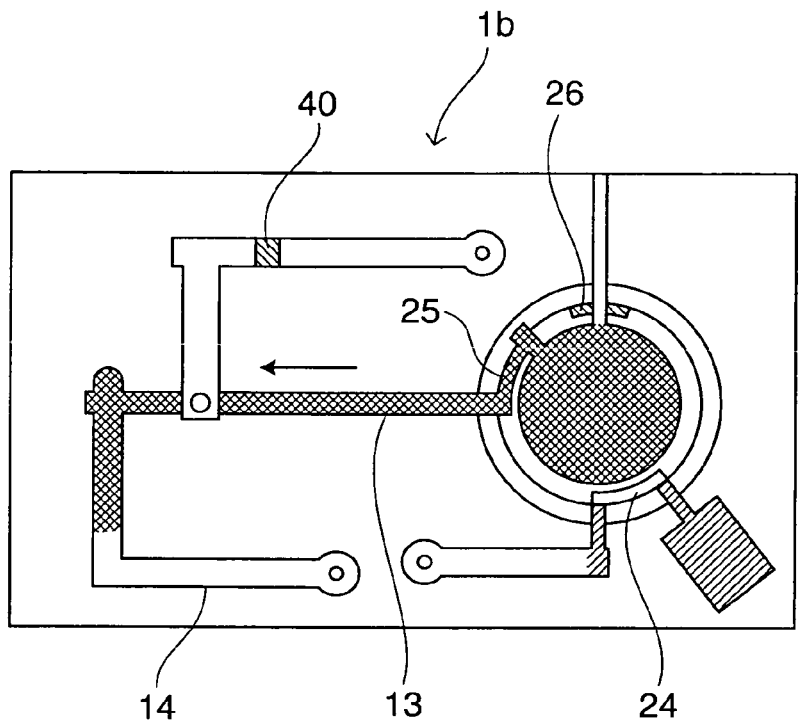

In turn, the syringe pump CP performs the sucking operation for a time period t8, and then the valve SV1 is closed (Steps S330 to S332), whereby the diluted sample is sucked into the channels 13, 14 from the diluent container 5 as shown in FIG. 83.

Figure 84:
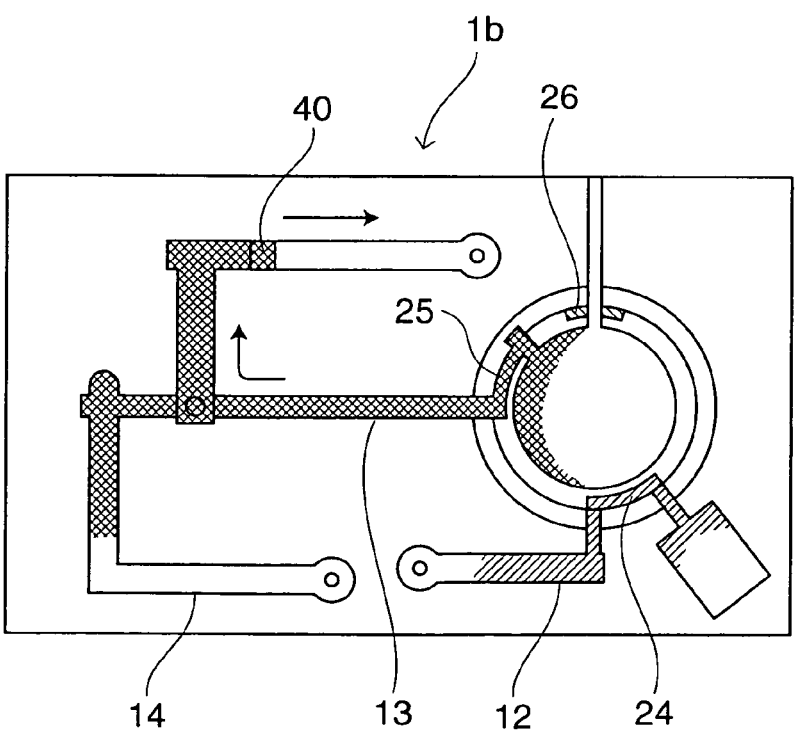

Subsequently, the syringe pump CP performs the sucking operation for a time period t9 with the valve SV3 being open, and then the valve SV3 is closed (Steps S333 to S336), whereby the diluted sample flows through the channel 13, the pellet 33 and the channel 15 from the diluent container 5 by suction as shown in FIG. 84, and 200 μL of the diluted sample is supplied into the absorbance measuring chamber 40.

The 200 μL diluted sample supplied into the absorbance measuring chamber 40 is further diluted by the 50 μL diluent preliminarily retained in the absorbance measuring chamber 40. As a result, a 625-time diluted sample is prepared. The diluted sample is irradiated with light from the laser diode 125, and the intensity of the transmitted light is detected by the photodiode 126. A detection value is stored in the control section 106 (Step S335a).

Figure 85:
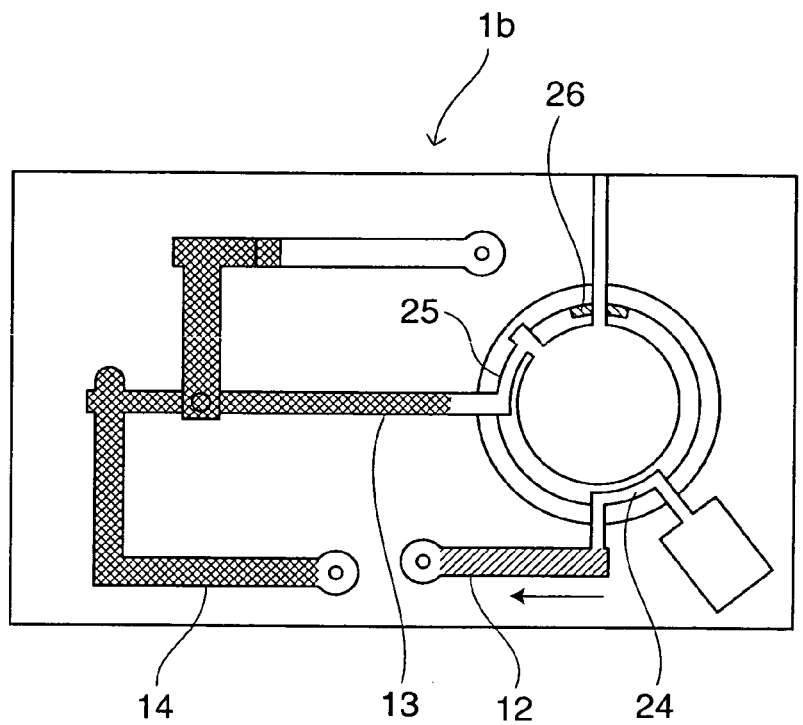

Subsequently, the syringe pump CP performs the sucking operation for a time period t10 with the valves SV1, SV2 being open, and then the valves SV1, SV2 are closed (Steps S337 to S339). Thus, the whole blood sample remaining in the sample receiving section 4 flows into the channel 12 and is retained in the channel 12, and the diluted sample remaining in the diluent container 5 flows into the channels 13, 14 and is retained in the channels 13, 14 as shown in FIGS. 84 and 85.

Figure 86:
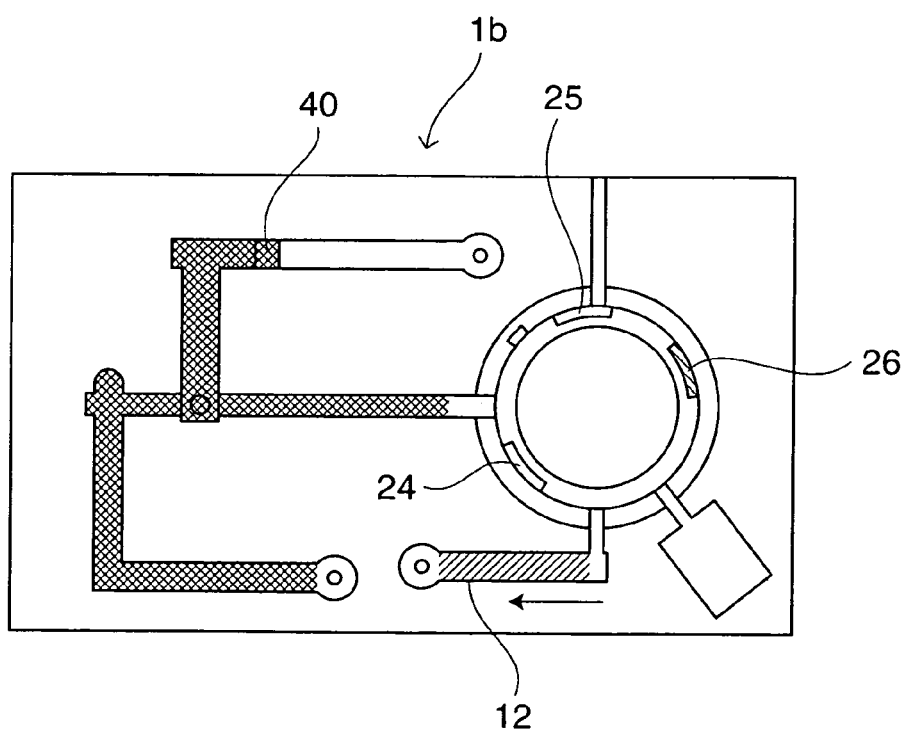

In turn, the stepping motor M1 is driven to rotate the inner cylinder 17 clockwise by an angle θ4 to a position as shown in FIGS. 38(a) to 38(c) (Steps S340 to S342). Thus, the vent hole 37 and the channel 11 are brought out of communication with the diluent container 5 and the channel 12, respectively, as shown in FIG. 86.

The measuring operation is thus completed with the residual whole blood sample retained in the channel 12 and with the diluted sample retained in the channels 13 to 15. Then, the result of the computation performed by the second computing section 106b is outputted together with an identification code to the display section 108 and the printer 300, and the cover 111 is unlocked (Steps S343, S344). Then, the user opens the cover 111, and removes the third unit 1b, which is in turn discarded (Steps S345, S346).

The third unit 1b may further include an electrically conductive member, which is connected to the electrode contacts 118, 119 when the unit 1b is set in the measuring section 110 as shown in FIG. 23. In this case, the control section 106 can detect the type of the measuring unit set in the measuring section 110 by checking the electrical continuity between the electrode contacts 118 and 119.

D. Determination of Number and Diameters of White Blood Cells and Determination of Amount of Hemoglobin When the constant current from the constant direct current source 101 (FIG. 21) is supplied to the diluted sample via the electrodes 34a and 35a in a space separated by the pellet 33b having the minute through-hole 33a as shown in FIG. 11, the electrical resistance between the electrodes 34 and 35 generally depends on the specific resistivity of a liquid component of the diluted sample. Particularly, the electrical resistance is determined by the electrical resistance of the liquid component present in and around the minute through-hole (orifice) 33a, mainly depending on the diameter of the minute through-hole 33a and the thickness of the pellet 33.

When a white blood cell passes through the minute through-hole 33a, the liquid component is removed by the volume of the white blood cell, so that the electrical resistance between the electrodes 34 and 35 correspondingly changes. A change in the electrical resistance is detected as a pulse voltage generated between the electrodes 34 and 35.

When the first unit 1 or the second unit 1a is set in the measuring section 110, the first computing section 106a determines the number of white blood cells on the basis of the number of pulses of the pulse voltage. Since the amplitude of the pulse is proportional to the volume of the white blood cell, the first computing section 106a detects the amplitude of each pulse, and calculates the spherical equivalent diameter of each white blood cell for preparation of a particle size distribution diagram.

When the first unit 1 or the third unit 1b is set in the measuring section 110, the second computing section 106b determines the absorbance of the diluted sample by a known method on the basis of the transmitted light intensity (blank value) of the diluent in the absorbance measuring chamber 40 and the transmitted light intensity of the diluted sample in the absorbance measuring chamber 40. The amount of hemoglobin is calculated on the basis of the absorbance thus determined.

In the preferred embodiment of the present invention, there has been described the first measuring unit for measurement of white blood cells and hemoglobin, the second measuring unit for measurement of white blood cells, and the third measuring unit for measurement of hemoglobin. However, it should be understood that the present invention be not limited to this embodiment, and that a measuring unit for measurement of sizes and numbers of red blood cells, platelets, and toner particles may also be used.

According to the embodiment of the present invention, the second computing section 106b acquires the intensity of transmitted light. However, the present invention is not limited to this embodiment, and the second computing section 106b may be constructed so as to acquire the intensity of scattered light or fluorescent light, or the intensity of light emitted from the sample retained in the absorbance measuring chamber 40. The second computing section 106b may also be constructed so as obtain the activity level of an enzyme such as ALP or peroxidase, the blood coagulation period, the amount of bilirubin, and CRP as an analysis result by analyzing the acquired information.

Further, the present embodiment uses whole blood as the samples for the first, second and third measuring units. However, the type of the samples used in the first, second and third measuring units may be different from one another. The samples for the first, second and third measuring units may be, for example, whole blood, urine and serum, respectively.

According to the present embodiment, it is checked whether or not the detection of a signal from a sample is properly achieved, before the sample is supplied into the receiving section. Therefore, the sample to be analyzed can efficiently be used without waste for improvement of the efficiency of the analysis.

What is claimed is:
1. A blood cell counter system comprising:
a measuring unit configured to receive a blood sample, the measuring unit including a pellet having a through-hole through which the blood sample passes, a first electrode disposed at one side of the pellet, a second electrode disposed at another side of the pellet, and a pump connection port; and
a blood analyzer that includes,
a main body having a cover and an accommodation section that removably receives a measuring unit, the cover and main body being attached together to enclose the measuring unit in the accommodation section, a power source that supplies an electric current to the first and second electrodes of the measuring unit set in the accommodation section, a first electrode contact that removably receives the first electrode and electrically connects the power source and the first electrode when the measuring unit is set in the accommodation section by the user, a second electrode contact that removably receives the second electrode and electrically connects the power source and the second electrode when the measuring unit is set in the accommodation section by the user, a pump which supplies a pressure for transporting the blood sample in the measuring unit, a connector which removably connects the pump connection port of the measuring unit and the pump, when the measuring unit is set in the accommodation section by the user, such that the pressure is supplied to the blood sample through the connector and the connecting port, an air chamber provided in a channel including the connector at an end thereof and which communicates with the pump and the measuring unit;

a pressure sensor provided in the air chamber for measuring an inside pressure of the air chamber, and a control section which, every time the measuring unit starts a measurement, compares the detected pressure in the air chamber with a predetermined pressure level and judges whether or not the measuring unit is properly set in the accommodation section by the user on the basis of a result of the comparison, the control section counts blood cells in the blood sample passing through the through-hole of the pellet by supplying the pressure while the power source is supplying the electric current to the first and second electrodes of the measuring unit set in the accommodation section.

2. The blood cell counter system of claim 1, wherein the blood analyzer further includes,
   a display which, if the control section judges that the measuring unit is properly set in the accommodation section by the user of the blood cell counter, outputs a message urging the blood sample to be introduced to the measuring unit.

3. The blood cell counter system of claim 1, wherein the blood analyzer further includes,
   a display which, if the control section judges that the measuring unit is properly set in the accommodation section by the user of the blood cell counter, outputs a result of judgment.

4. The blood cell counter system of claim 1, wherein the blood analyzer further includes,
   a channel including the connector at an end thereof and which communicates with the pump and the measuring unit; and
   a valve which opens and closes the channel,
   wherein the control section judges whether or not the measuring unit is properly set in the accommodation section by the user, on the basis of the detected pressure with the channel being opened by the valve of the blood cell counter.

5. The blood cell counter system of claim 1, wherein the pump connection port is a first pipe and the connector is a second pipe that removably receives the first pipe.

* * * * *